(12) United States Patent
Coenen et al.

(10) Patent No.: US 9,132,982 B2
(45) Date of Patent: *Sep. 15, 2015

(54) FOLDING APPARATUS AND METHOD OF FOLDING A PRODUCT

(75) Inventors: Joseph Daniel Coenen, Kaukauna, WI (US); Gregory J. Rajala, Neenah, WI (US); John Soosai Alphonse, Tamil Nadu (IN); Mohammed Shafi Khurieshi, Andhra Pradesh (IN); Mahendra Mittapalli, Andhra Pradesh (IN)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 1128 days.

This patent is subject to a terminal disclaimer.

(21) Appl. No.: 12/972,012

(22) Filed: Dec. 17, 2010

(65) Prior Publication Data

US 2012/0157284 A1 Jun. 21, 2012

(51) Int. Cl.
*B31B 1/26* (2006.01)
*B65H 45/16* (2006.01)
*A61F 13/496* (2006.01)
*A61F 13/15* (2006.01)

(52) U.S. Cl.
CPC .......... *B65H 45/16* (2013.01); *A61F 13/15747* (2013.01); *A61F 13/496* (2013.01); *B65H 2406/332* (2013.01); *B65H 2801/57* (2013.01)

(58) Field of Classification Search
CPC ...... B65H 45/165; B65H 45/22; B65H 45/00; B65H 45/168; B65H 45/04; B65H 2220/01; B65H 2513/10; B65H 2801/57; B65H 2406/33

USPC ......... 493/405, 408, 416, 418, 424, 442, 445, 493/450, 415, 419, 434, 435, 454
See application file for complete search history.

(56) References Cited

U.S. PATENT DOCUMENTS

| | | |
|---|---|---|
| 4,053,150 A | 10/1977 | Lane |
| 4,519,596 A | 5/1985 | Johnson et al. |
| 4,650,173 A | 3/1987 | Johnson et al. |
| 6,630,096 B2 | 10/2003 | Venturino et al. |
| 7,399,266 B2 | 7/2008 | Aiolfi et al. |
| 7,846,082 B2 | 12/2010 | Burns, Jr. et al. |
| 2003/0042660 A1 | 3/2003 | Venturino et al. |

(Continued)

FOREIGN PATENT DOCUMENTS

WO 2009083788 A1 7/2009

OTHER PUBLICATIONS

International Search Report and Written Opinion for PCT/IB2011/055055 dated Jun. 18, 2012, 10 pages.

*Primary Examiner* — Stephen F Gerrity
*Assistant Examiner* — Joy N Sanders
(74) *Attorney, Agent, or Firm* — Armstrong Teasdale LLP

(57) ABSTRACT

An apparatus for folding a product includes a receiving roll having a first direction of rotation. The receiving roll is adapted to selectively hold first and second portions of the product. A folding roll of the apparatus has a second direction of rotation that is opposite from the first direction of rotation. The folding roll is adapted to selectively hold the first portion of the product thereto. An oscillating member is adapted to transfer the first portion of the product from the receiving roll to the folding roll. The oscillating member is configured to move in both the first direction and the second direction.

18 Claims, 55 Drawing Sheets

(56) References Cited

U.S. PATENT DOCUMENTS

| | | |
|---|---|---|
| 2003/0226862 A1 | 12/2003 | Vogt et al. |
| 2005/0073090 A1 | 4/2005 | White |
| 2006/0266465 A1* | 11/2006 | Meyer .......................... 156/250 |
| 2007/0238596 A1* | 10/2007 | Terhaag et al. ............... 493/433 |
| 2008/0176729 A1 | 7/2008 | Anelli et al. |
| 2009/0098995 A1* | 4/2009 | Burns et al. ................... 493/440 |

* cited by examiner

FOLDING APPARATUS AND METHOD OF FOLDING A PRODUCT

BACKGROUND

The field of the present invention relates generally to apparatus and methods for folding products and more particularly, to apparatus and methods for folding products with increased alignment control at relatively high line speeds.

One known technology used to fold products as they proceed through a product manufacturing system is "blade folding". Blade folding involves striking a discrete, moving product at a desired location with a blade to form a "bite" in the product. The bite is directed into a set of in-running conveyor belts to fold portions of the product. Examples of such blade folding apparatus and methods of their use are described in U.S. Pat. No. 4,053,150 to Lane; U.S. Pat. No. 4,519,596 to Johnson et al.; and U.S. Pat. No. 4,650,173 to Johnson et al. Various products can be folded using blade folding apparatus including disposable personal care products. Disposable personal care products are well known and include diapers, training pants, adult incontinence garments, feminine pads, bed liners, pet-care mats, dinner napkins, toweling, chair liners, etc.

One disadvantage of known blade folding technology is that the precision and repeatability of the folds in the products is dependent upon the timing of when the blade strikes the moving product as well as the traction of the in-running belts to the product bite. Plus, blade folding requires that the product is "free" when it is struck by the blade. Thus, there is a period of time in the folding process when a leading portion of the product is not held in place, and as a result, is not under direct positioning control. These features of blade folding are undesirable when precise fold positioning is needed, particularly at high speeds, such as speeds ranging from 400 products per minute to 4000 products per minute, depending on the product being folded.

Another disadvantage of blade folding is the "cudgeling effect". That is, the bludgeoning force of the blade striking the product can result in deformed products, damaged products, poor folding alignment, poor folding repeatability, as well as other undesirable results.

Thus, there is a need for a folding apparatus and method of folding products at high speeds where the products can be folded in repeatable alignment at high speeds. There is a further need for apparatus and methods for folding products without the resulting deformation, damage and/or other undesirable effects inherent in current blade folding apparatus and methods.

BRIEF DESCRIPTION

In one aspect, an apparatus for folding a product having a first portion and a second portion generally comprises a receiving roll having a first direction of rotation. The receiving roll is adapted to selectively hold the first and second portions of the product thereto. A folding roll has a second direction of rotation that is opposite from the first direction of rotation. The folding roll is adapted to selectively hold the first portion of the product thereto. An oscillating member is adapted to transfer the first portion of the product from the receiving roll to the folding roll. The oscillating member is configured to move in both the first direction and the second direction.

In another aspect, an apparatus for folding products having a first portion, a second portion, and a transverse fold axis generally comprises a receiving roll configured to hold the first portion and the second portion of the product thereto and to release the first portion while continuing to hold the second portion of the product. The receiving roll is configured to rotate in a first direction. An oscillating member is positioned adjacent the receiving roll. The oscillating member is capable of movement in the first direction and in a second direction. The oscillating member is configured to receive the first portion of the product from the receiving roll while moving in the second direction. A folding roll is positioned adjacent to the receiving roll and the oscillating member. The folding roll is rotatable in the second direction and configured to receive the first portion of the product from the oscillating member while the oscillating member is moving in the first direction and to transfer the first portion of the product to the receiving roll such that the product is folded generally along the transverse fold axis and the first portion is generally overlying the second portion.

In yet another aspect, a method of folding a product generally comprises directing a product to a receiving roll. The product has a first portion, a second portion, and a transverse fold axis separating the first portion and the second portion. The first and second portions of the product are held on the receiving roll while the receiving roll rotates in a first direction. The first portion of the product is transferred from the receiving roll to an oscillating member while the oscillating member is moving in a second direction. The direction of the oscillating member is changed from the second direction to the first direction. The first portion of the product is transferred from the oscillating member to a folding roll while the oscillating member is moving in the first direction and the folding roll is rotating in the second direction. The first portion of the product is transferred from the folding roll to the receiving roll such that the first portion of the product is in overlying relationship with the second portion and the product is folded generally along the transverse fold axis.

BRIEF DESCRIPTION OF THE DRAWINGS

Corresponding reference characters indicate corresponding parts throughout the drawings.

DETAILED DESCRIPTION OF THE DRAWINGS

Figure 1:
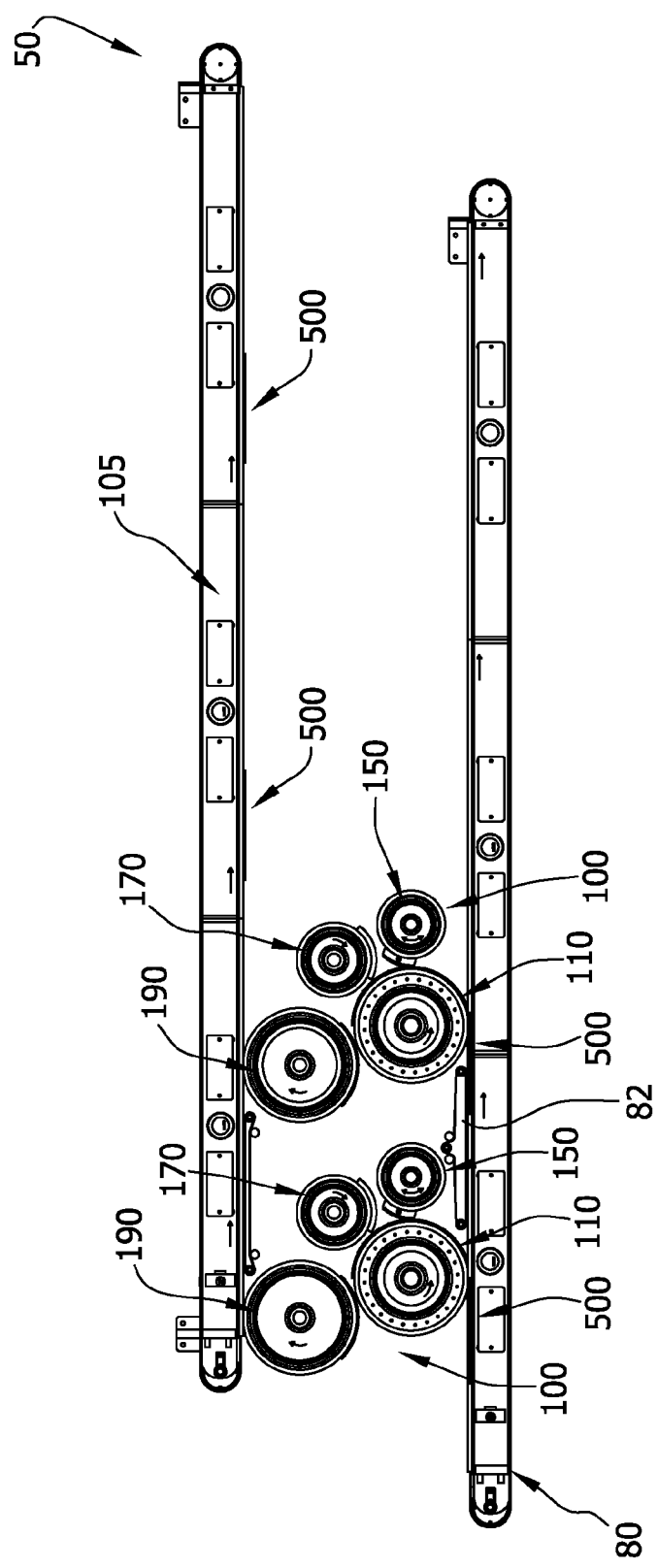
FIG. 1 is a schematic of a portion of a manufacturing system for manufacturing products, the manufacturing system having two folding apparatus of one suitable embodiment.

FIG. 1 is a schematic of a portion of a manufacturing system, indicated generally at 50, for manufacturing products (such as personal care products) having one embodiment of a folding apparatus, indicated generally at 100. The illustrated configuration of the manufacturing system 50 has two folding apparatus 100 but it is contemplated that the system could have fewer (i.e., one) or more folding apparatus. The folding apparatus 100 is capable of maintaining accurate control of the product while it is being folded at high line speeds. As a result, the products being manufactured by the illustrated system 50 are folded more precisely, with greater repeatability, and with less force (and thus less product damage and deformation) than prior art folding apparatus, such as blade folding apparatus. As used herein, the term "high line speed" refers to product manufacturing rates of 400 products per minute (ppm) or greater, such as 400 ppm to 4000 ppm, or 600 ppm to 3000 ppm, or 900 ppm to 1500 ppm. However, it is understood that the product manufacturing rate is directly dependent on the product being manufactured. Thus, the term "high line speed" is relative and can differ from one product to another.

For exemplary purposes only, the illustrated manufacturing system 50 and thus, the folding apparatus 100 will be described herein as a disposable training pant manufacturing system and folding apparatus. It is understood, however, that the manufacturing system and folding apparatus 100 can be configured to manufacture and fold numerous other products, including but not limited to, other types of personal care products, foil products, film products, woven products, packaging products, industrial products, food products, etc., whether disposable or non-disposable, and whether absorbent or non-absorbent, without departing from the scope of the invention. Other suitable personal care products that could be manufactured by the system 50 and folded by the folding apparatus 100 include, but are not limited to, diapers, adult incontinence garments, panty liners, and feminine pads.

As illustrated in FIG. 1, a plurality of discrete training pants 500 are fed along a first conveying member, indicated generally at 80. The first conveying member 80 delivers each of the training pants 500 in a pre-folded configuration to one of the two folding apparatus 100 for folding the training pants from the pre-folded configuration to a folded configuration. The folded training pants 500 are conveyed from the respective folding apparatus 100 by a second conveying member, indicated generally at 105, to other components (not shown) of the system 50. Since both of the folding apparatus 100 illustrated in FIG. 1 are substantially the same, the detailed description of only one is provided herein.

Figure 2:
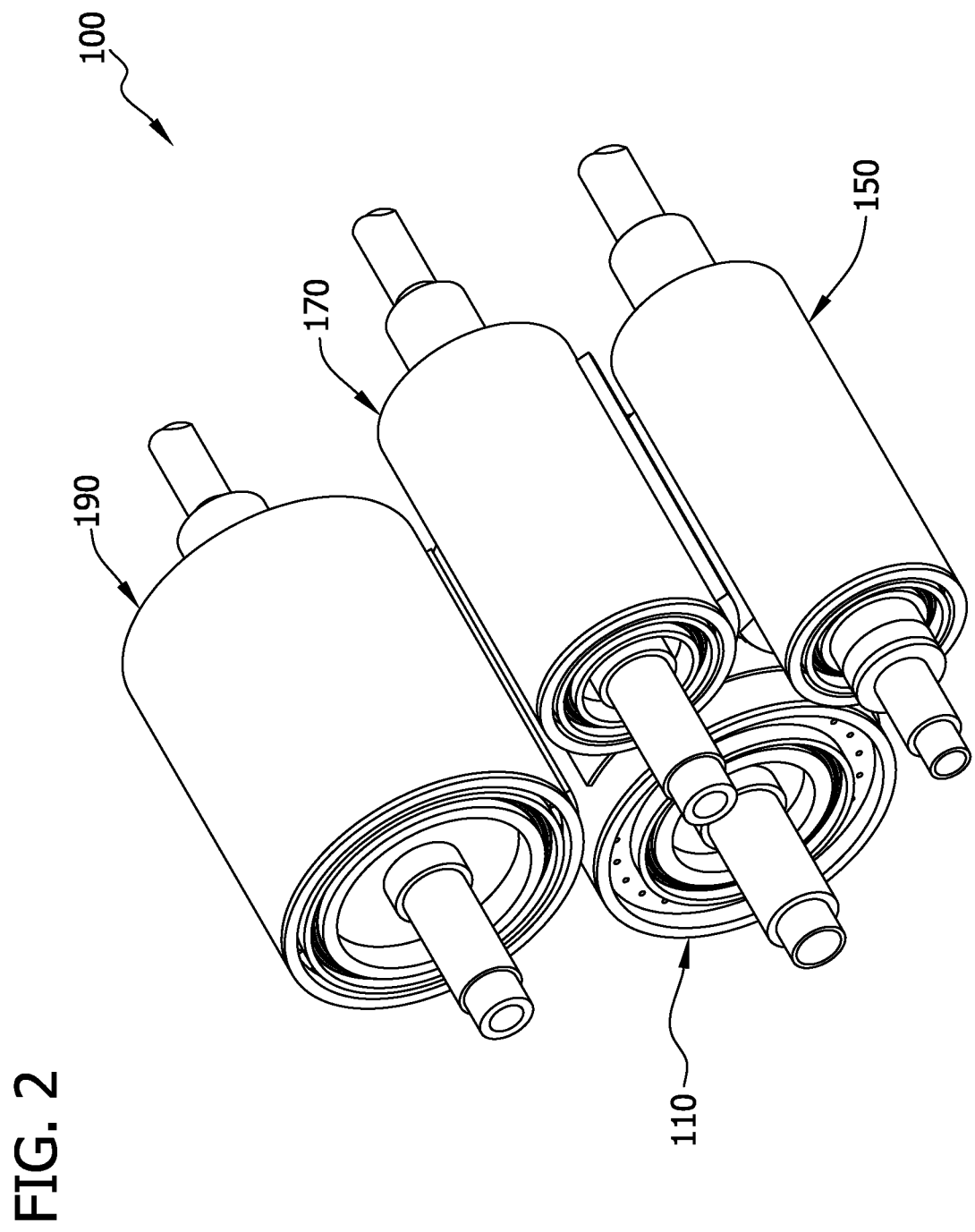
FIG. 2 is a perspective of one of the folding apparatus removed from the manufacturing system, the folding apparatus having a receiving roll, an oscillating member, a folding roll, and a transferring roll.
Figure 3:
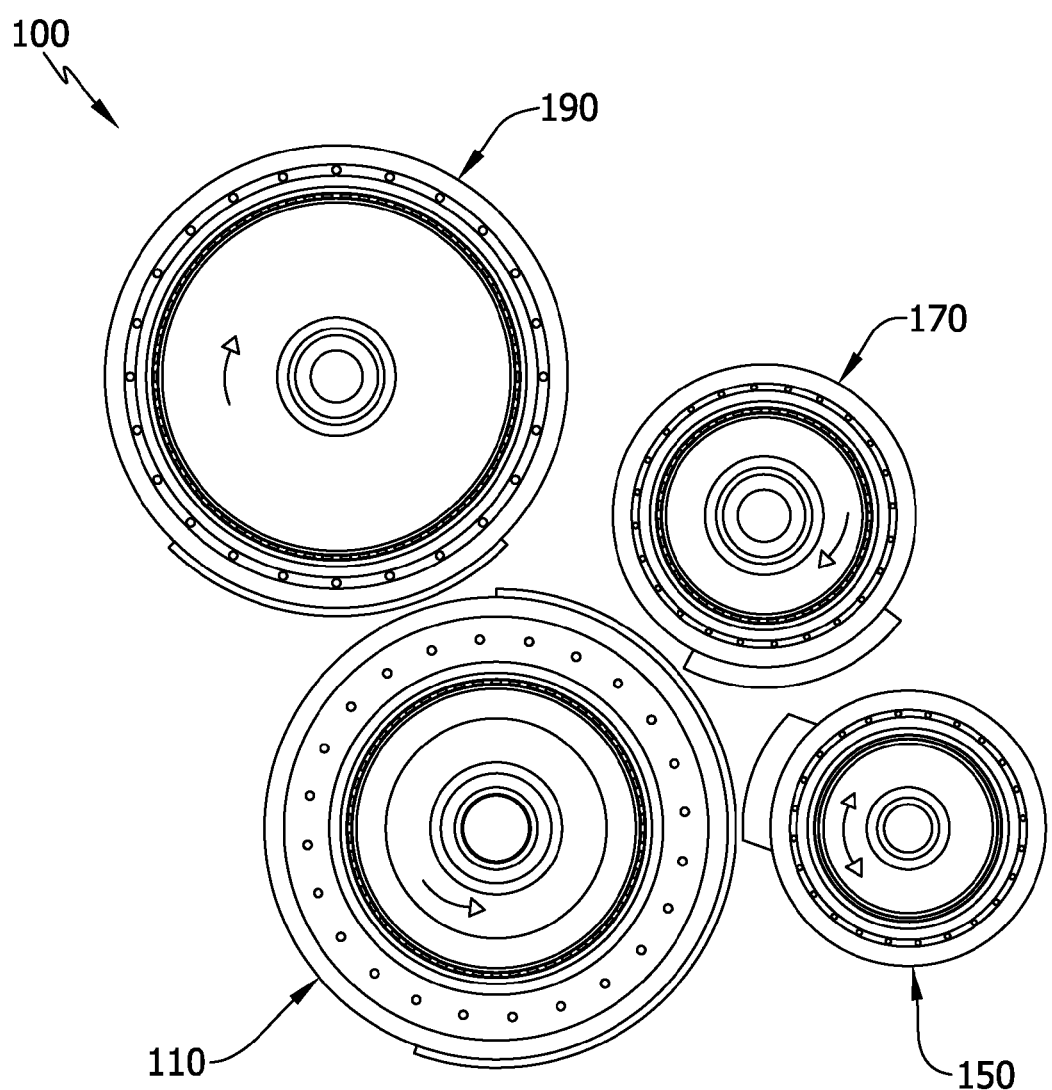
FIG. 3 is an end view of the folding apparatus of FIG. 2.
Figure 4:
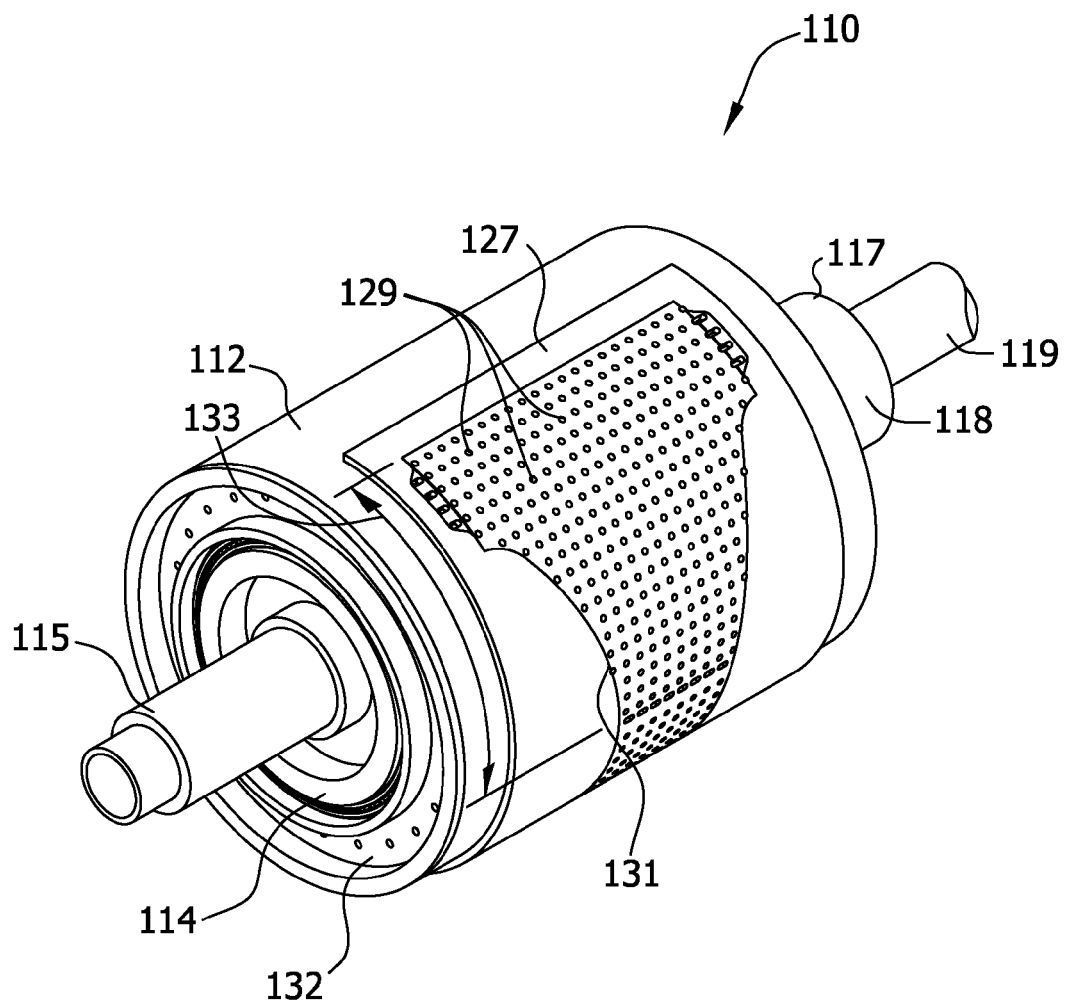
FIG. 4 is a perspective of the receiving roll of the folding apparatus.

As illustrated in FIGS. 2 and 3, the folding apparatus 100 comprises a receiving roll 110, an oscillating member 150, a folding roll 170, and a transferring roll 190. Each of the receiving roll 110, the oscillating member 150, the folding roll 170, and the transferring roll 190 is indicated generally by their respective reference number.

Figure 5:
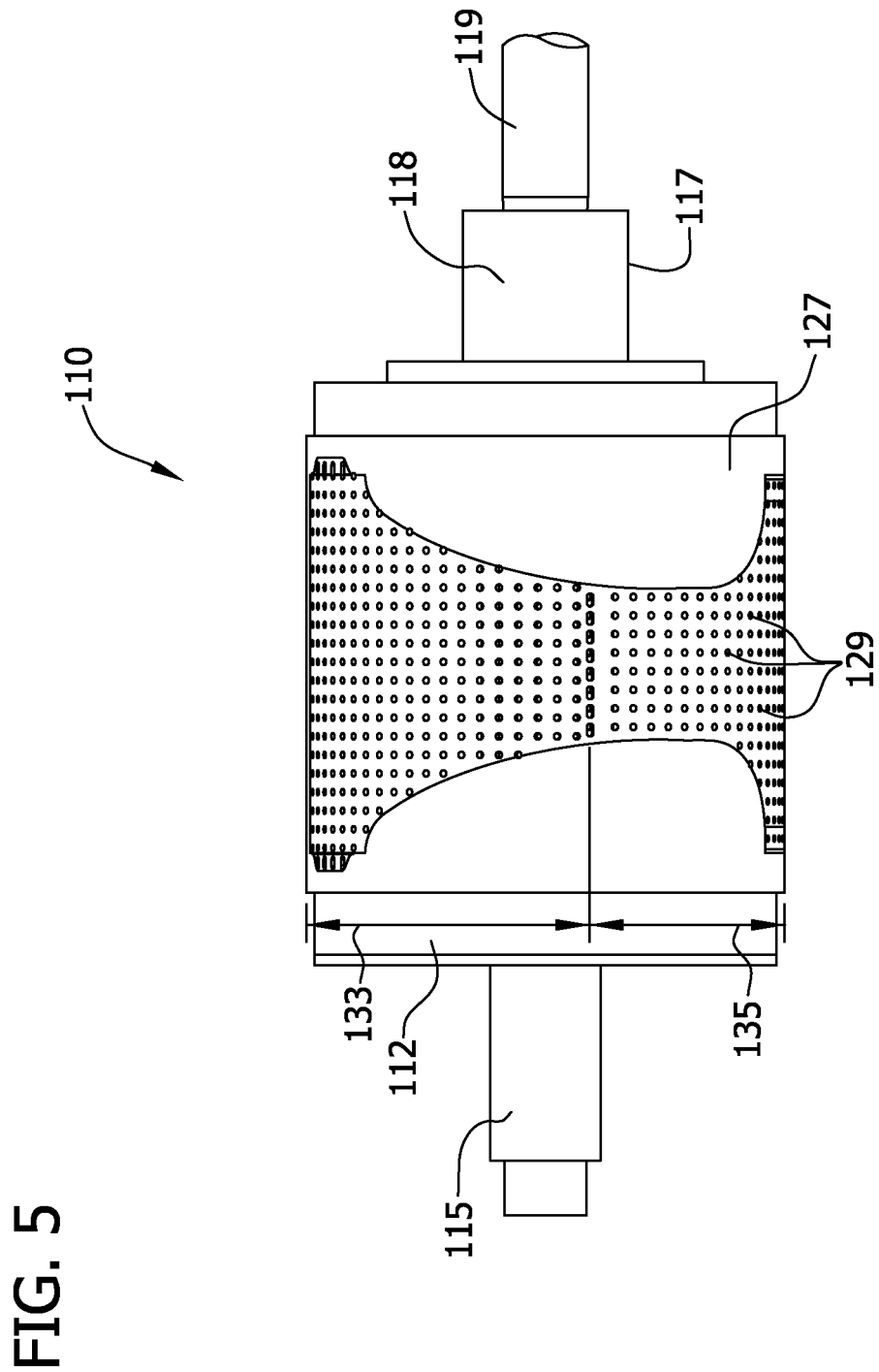
FIG. 5 is a right side view of the receiving roll as seen in FIG. 4.
Figure 6:
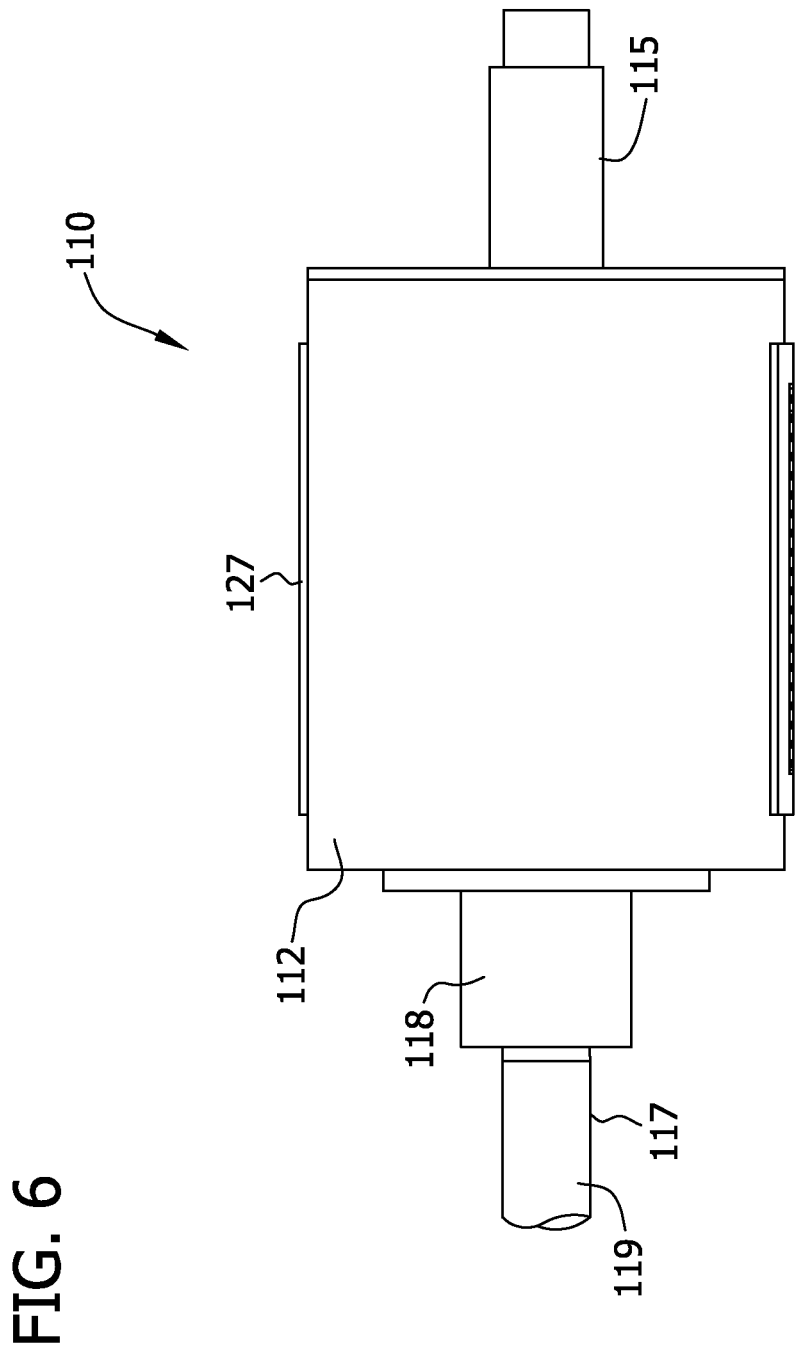
FIG. 6 is a left side view of the receiving roll.
Figure 7:
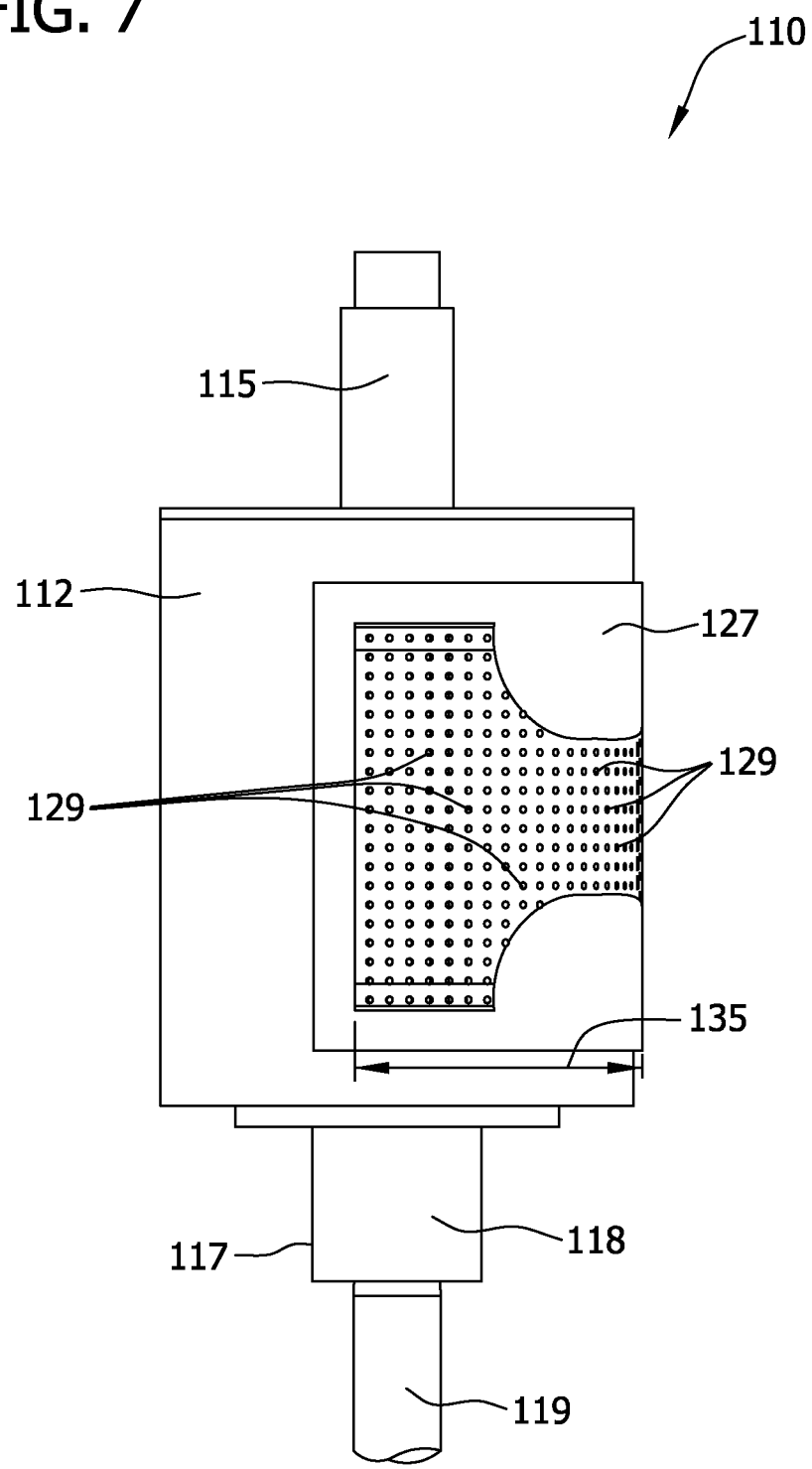
FIG. 7 is a bottom view of the receiving roll.
Figure 8:
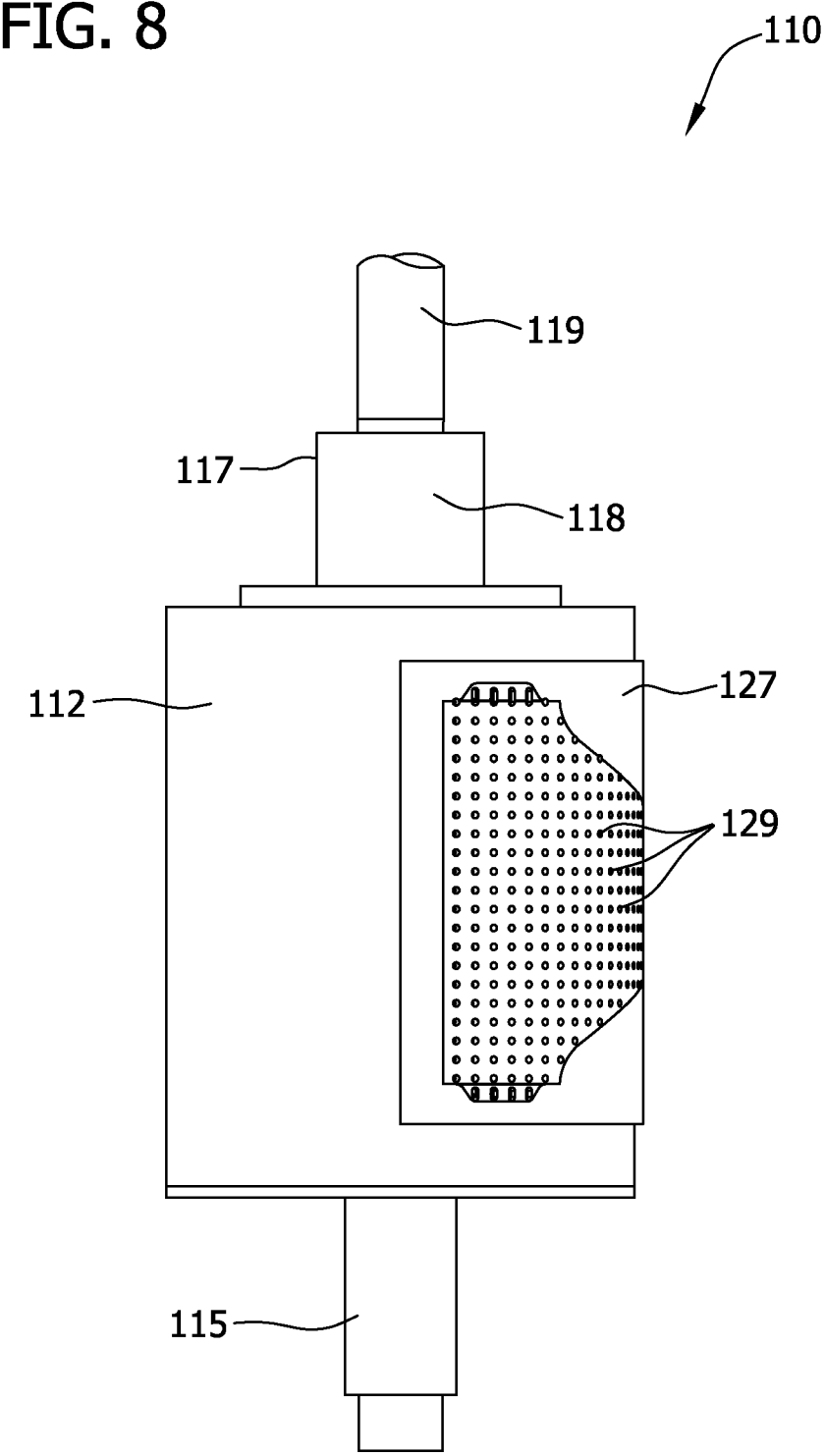
FIG. 8 is a top view of the receiving roll.

The receiving roll 110 comprises an inner cylinder 111 (FIGS. 9-11) and an outer cylinder 112 (FIGS. 4-9) that is rotatable about the inner cylinder. With reference to FIGS. 4-8, the outer cylinder 112 comprises a raised engagement member 127 adapted to receive, hold, and feed the training pant 500 through the folding apparatus 100. The raised engagement member 127 includes a plurality of circular apertures 129 arranged to generally match the profile of the pre-folded configuration of the training pant 500. The engagement member 127 includes a first zone 133 and a second zone 135. The apertures 129 in the second zone 135 are offset from the apertures in the first zone 133. More specifically, the apertures 129 in the first and second zones 133, 135 are generally aligned in columns about the circumference of the receiving roll 110 and in rows, which extend in the cross-direction of the receiving roll. As seen in FIG. 5, the apertures 129 defining the columns in the second zone 135 are laterally off-set from the apertures defining the columns in the first zone 133. The outer cylinder 112 is closed by a pair of end plates 132 (FIG. 9).

The illustrated receiving roll 110 is adapted to receive and hold one training pant 500 per revolution. It is understood, however, that the receiving roll 110 can be adapted to receive and hold a plurality of training pants 500 per revolution. It is also understood that the raised engagement member 127 can be flush with the remainder of the outer cylinder 112 (i.e., not raised). It is further understood that the apertures 129 in the engagement member 127 of the outer cylinder 112 can be arranged differently, that there can be more or fewer apertures than illustrated in the accompanying drawings, and that the apertures can have different shapes and sizes than those illustrated. It is also understood that the inner and outer cylinders could be other shapes that provide concentric surfaces such as partial spheres, cones or a stepped series of cylinders.

Figure 9:
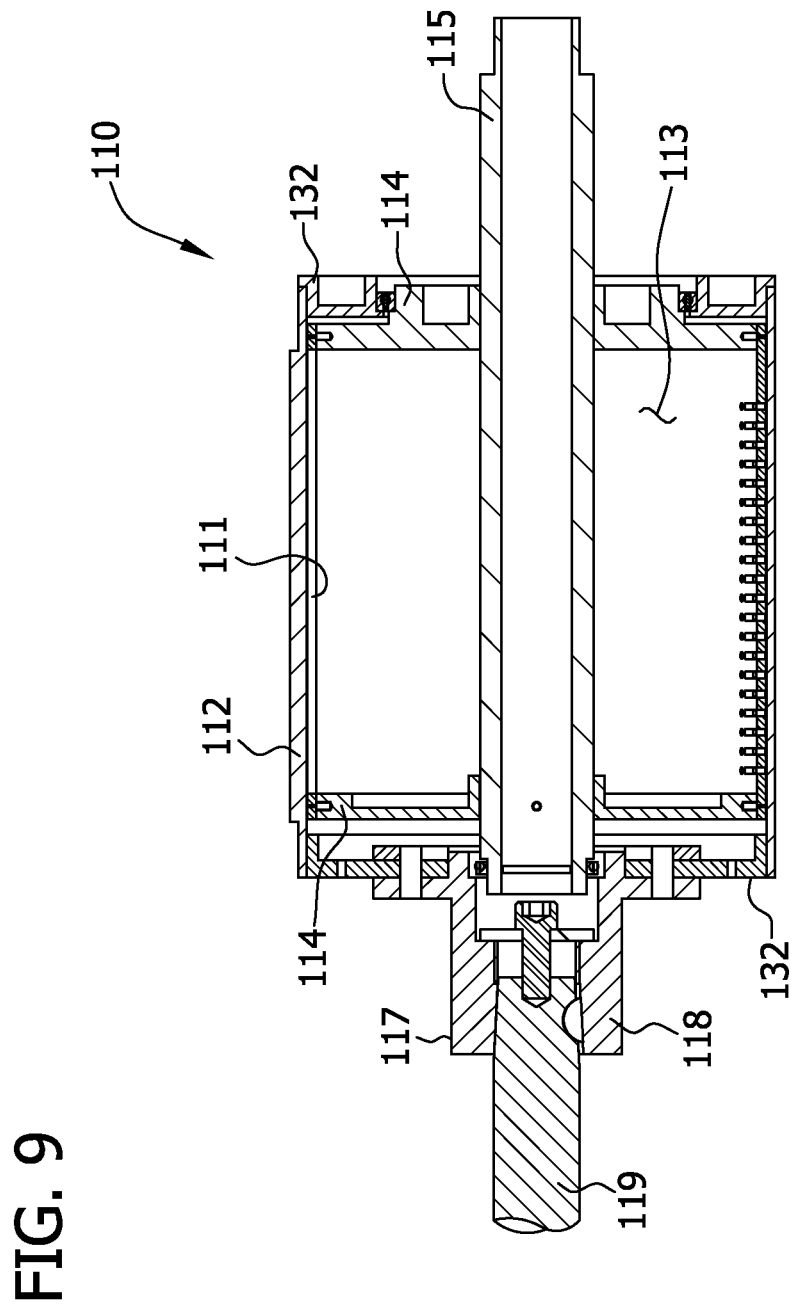
FIG. 9 is a vertical cross-section of the receiving roll.
Figure 10:
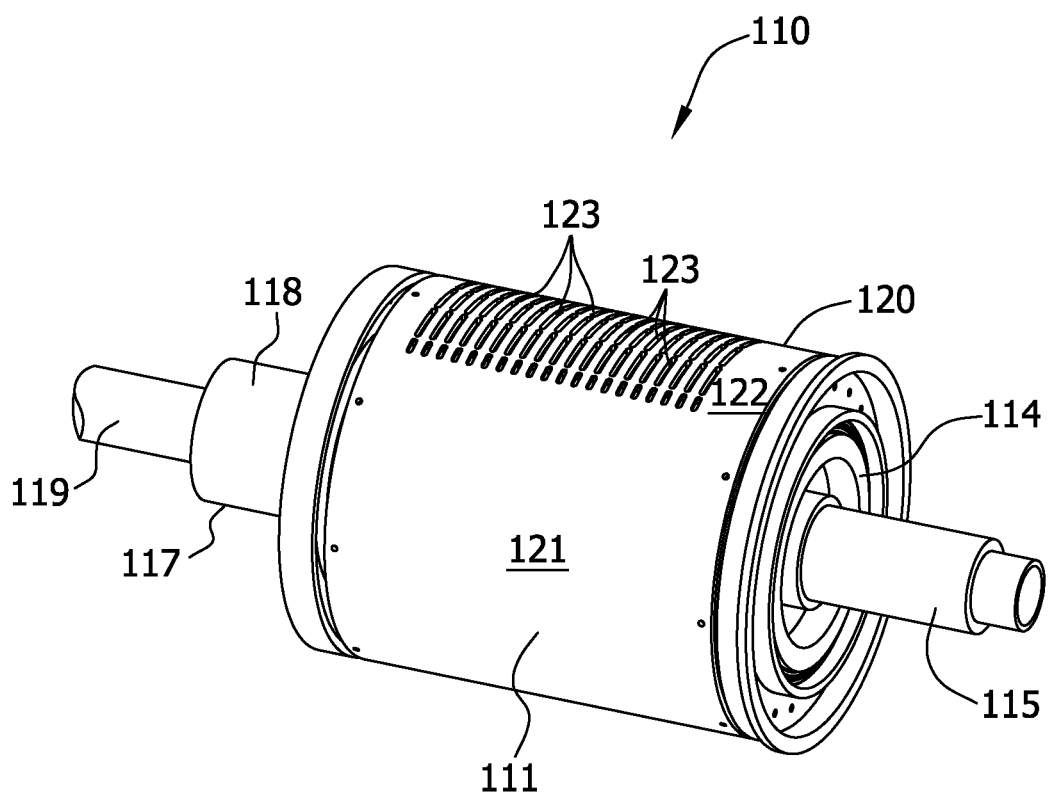
FIGS. 10 and 11 are perspectives of the receiving roll with an outer cylinder of the receiving roll removed.
Figure 11:
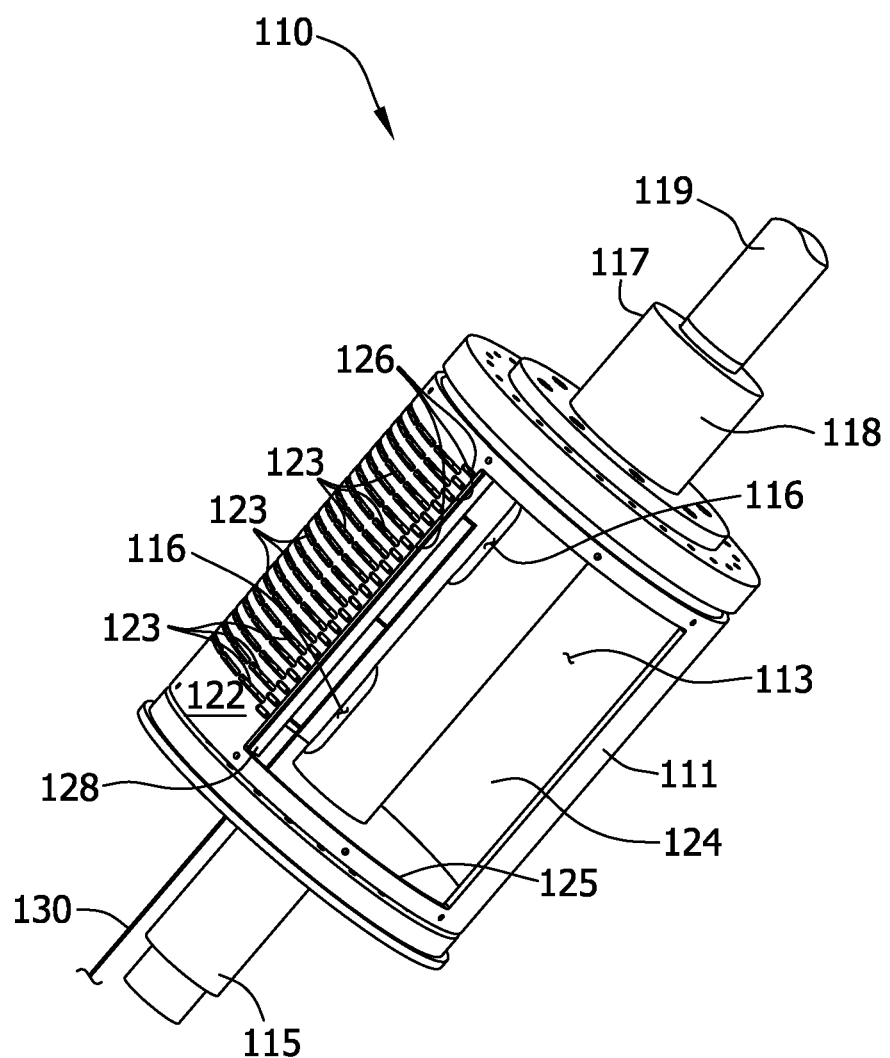

In the illustrated embodiment, the inner cylinder 111 is stationary and defines an interior chamber 113 (FIGS. 9 and 11). A conduit 115 extends into and is in fluid communication with the interior chamber 113 for allowing a suitable vacuum source (not shown) to apply a vacuum to the interior chamber. As seen in FIGS. 10 and 11, the inner cylinder 111 comprises a wall 120 with three discrete segments about its circumference: a solid segment 121; a slotted segment 122 having a plurality of slots 123 and a row of oval apertures 126; and an opened segment 124 having a generally rectangular opening 125. Each of the oval apertures 126 in the slotted segment 122 are transversely offset from the slots 123 and in fluid communication with an elongate enclosure 128. A pressurized air conduit 130 is provided to fluidly connect the elongate enclosure 128 to a suitable source of pressurized air (not shown). A pair of end plates 114 disposed adjacent the ends of the inner cylinder 111 closes the interior chamber 113.

As seen in FIGS. 4-9, a drive assembly 117 is operatively connected to the outer cylinder 112 for rotating the outer cylinder with respect to the inner cylinder 111. The drive assembly 117 includes a hub 118, a shaft 119 coupled to the hub, and a suitable drive mechanism (not shown) capable of rotating the shaft and hub.

Figure 12:
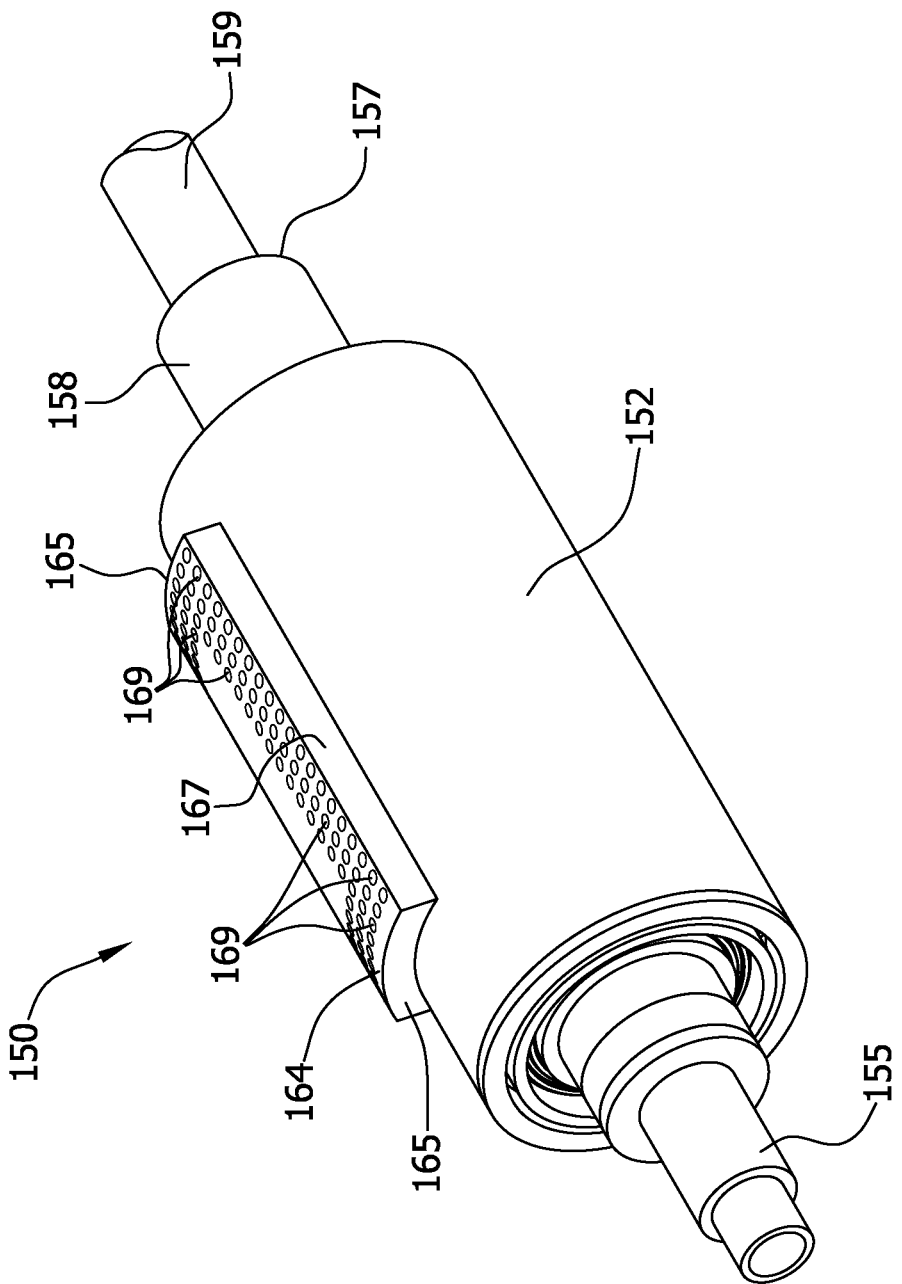
FIG. 12 is a perspective of the oscillating member of the folding apparatus.
Figure 13:
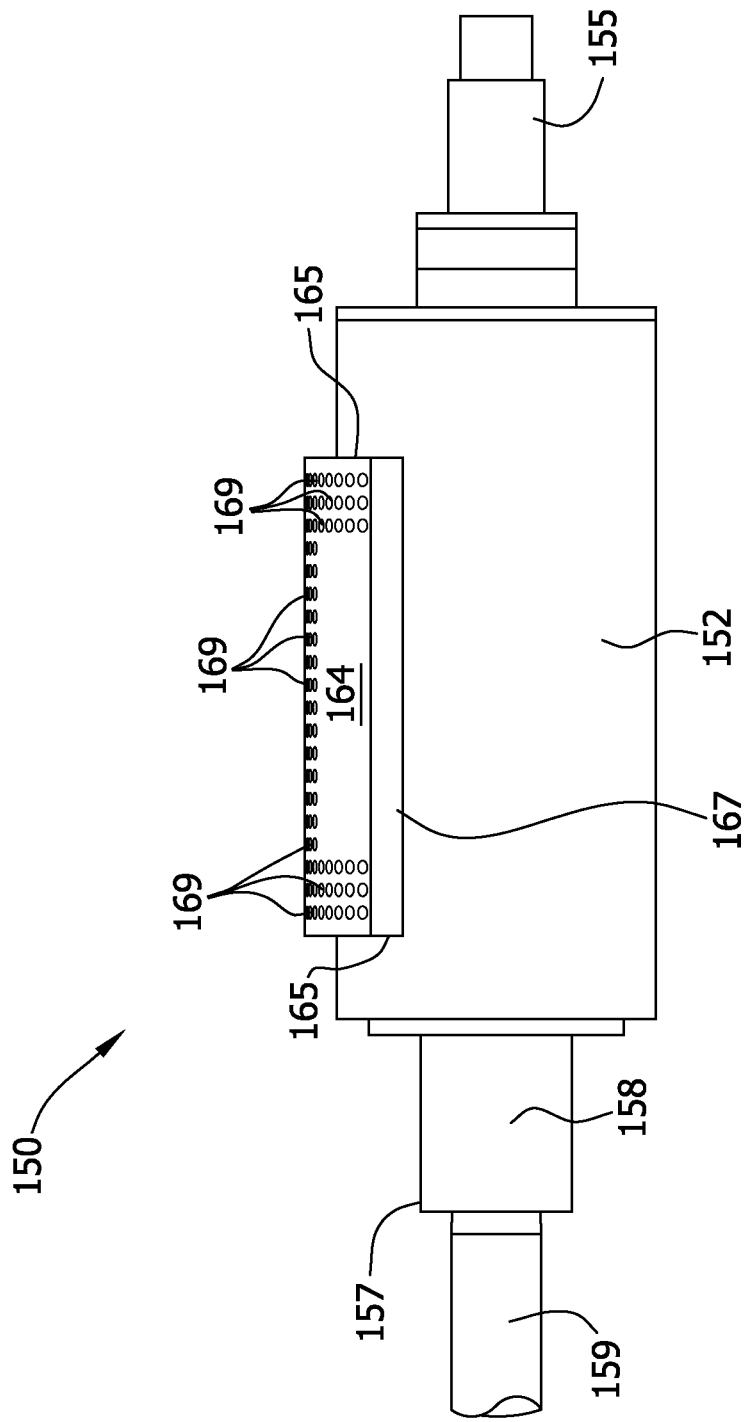
FIG. 13 is a left side view of the oscillating member as seen in FIG. 12.
Figure 14:
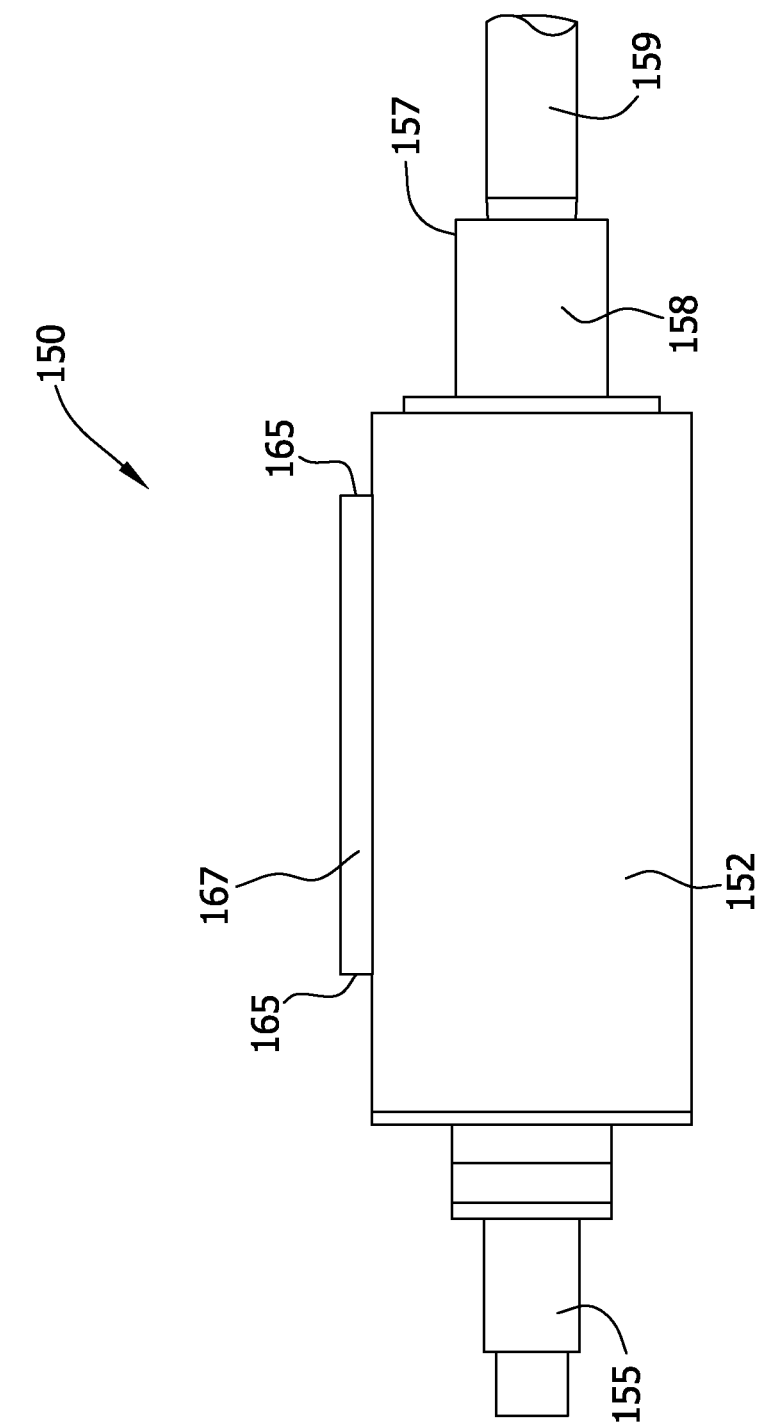
FIG. 14 is a right side view of the oscillating member.
Figure 15:
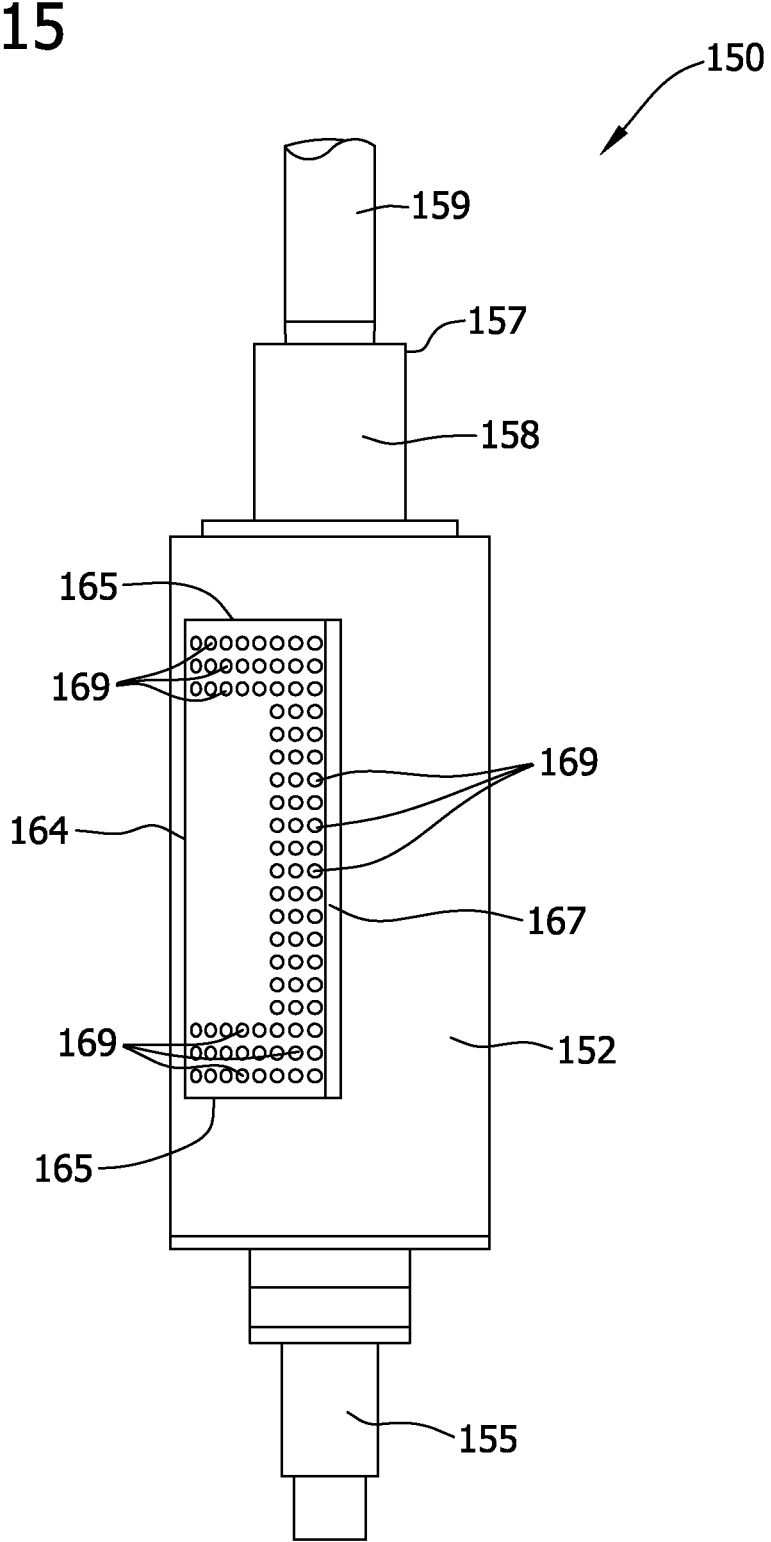
FIG. 15 is a top view of the oscillating member.
Figure 16:
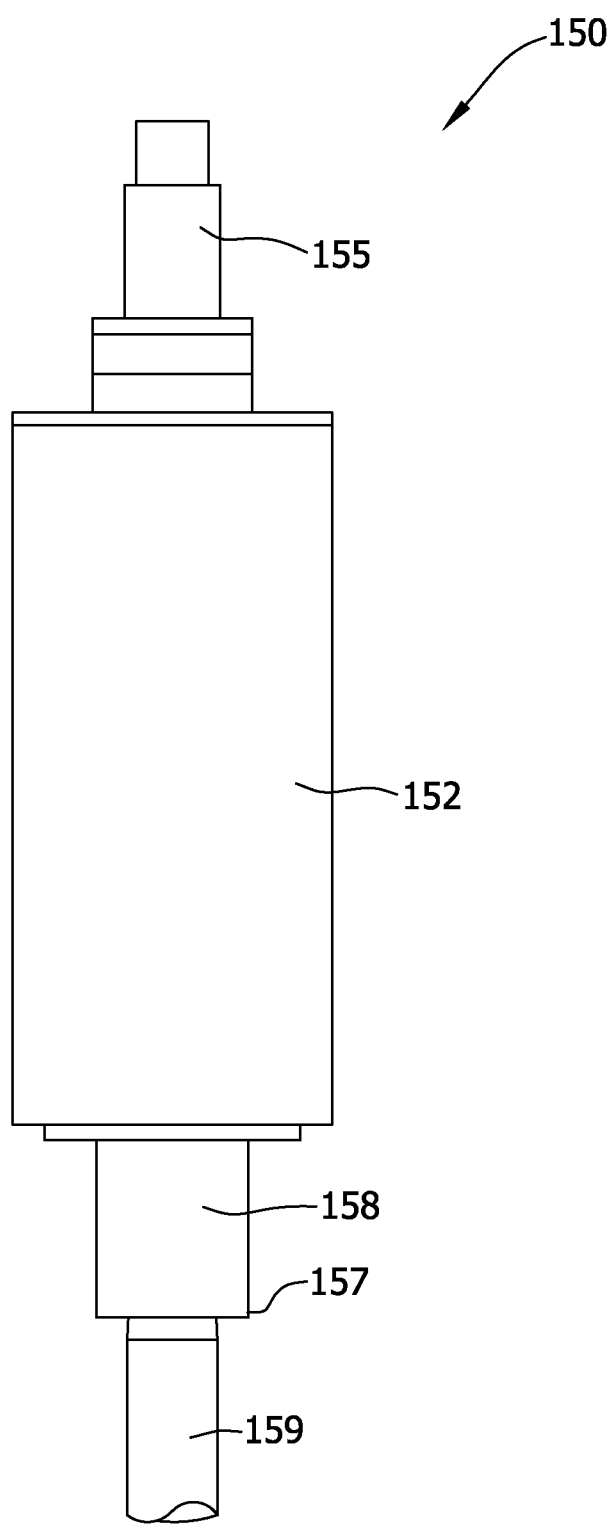
FIG. 16 is a bottom view of the oscillating member.
Figure 17:
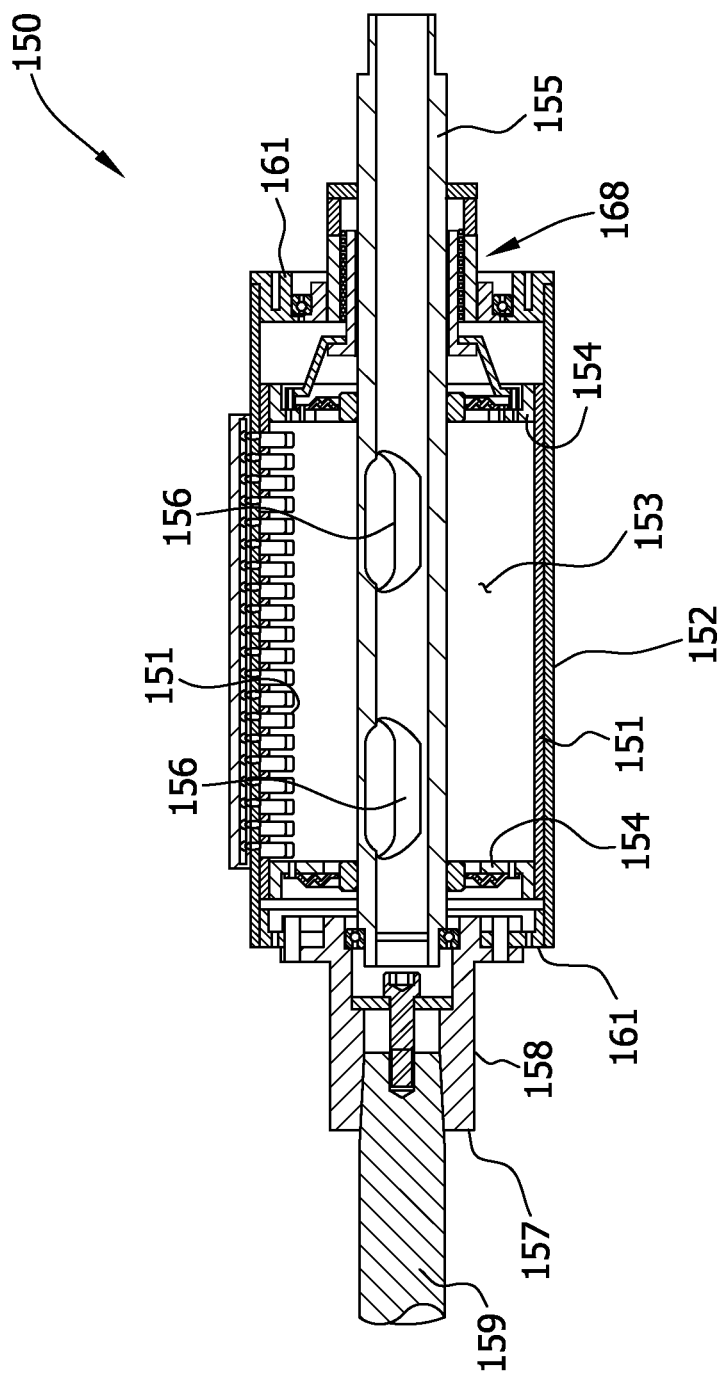
FIG. 17 is a vertical cross-section of the oscillating member.

With reference now to FIGS. 12-22, the oscillating member 150 comprises an inner cylinder 151 and an outer cylinder 152 that is rotatable about the inner cylinder. As seen in FIGS. 12 and 13, the outer cylinder 152 comprises a raised puck 164 adapted to receive a portion of the training pant from the receiving roll 110 and to transfer the portion to the folding roll 170. The puck 164 includes a pair of lateral sides 165, a pair of longitudinal sides 167, and a plurality of circular apertures 169 arranged generally adjacent the lateral sides and one of the longitudinal sides. As a result, a portion of the puck 164 is free of apertures 169. The outer cylinder 152 is closed by a pair of end plates 161 (FIG. 17).

It is understood that the puck 164 can be flush with the remainder of the outer cylinder 152 of the oscillating member 150 (i.e., not raised). It is further understood that the apertures 169 in the puck 164 of the outer cylinder 152 can be arranged differently, that there could be more or fewer apertures than illustrated in the accompanying drawings, and that the apertures can have different shapes and sizes than those illustrated. It is also understood that the inner and outer cylinders could be other shapes that provide concentric surfaces such as partial spheres, cones, a stepped series of cylinders, or partials of the above since the oscillating member does not need to rotate 360 degrees.

Figure 18:
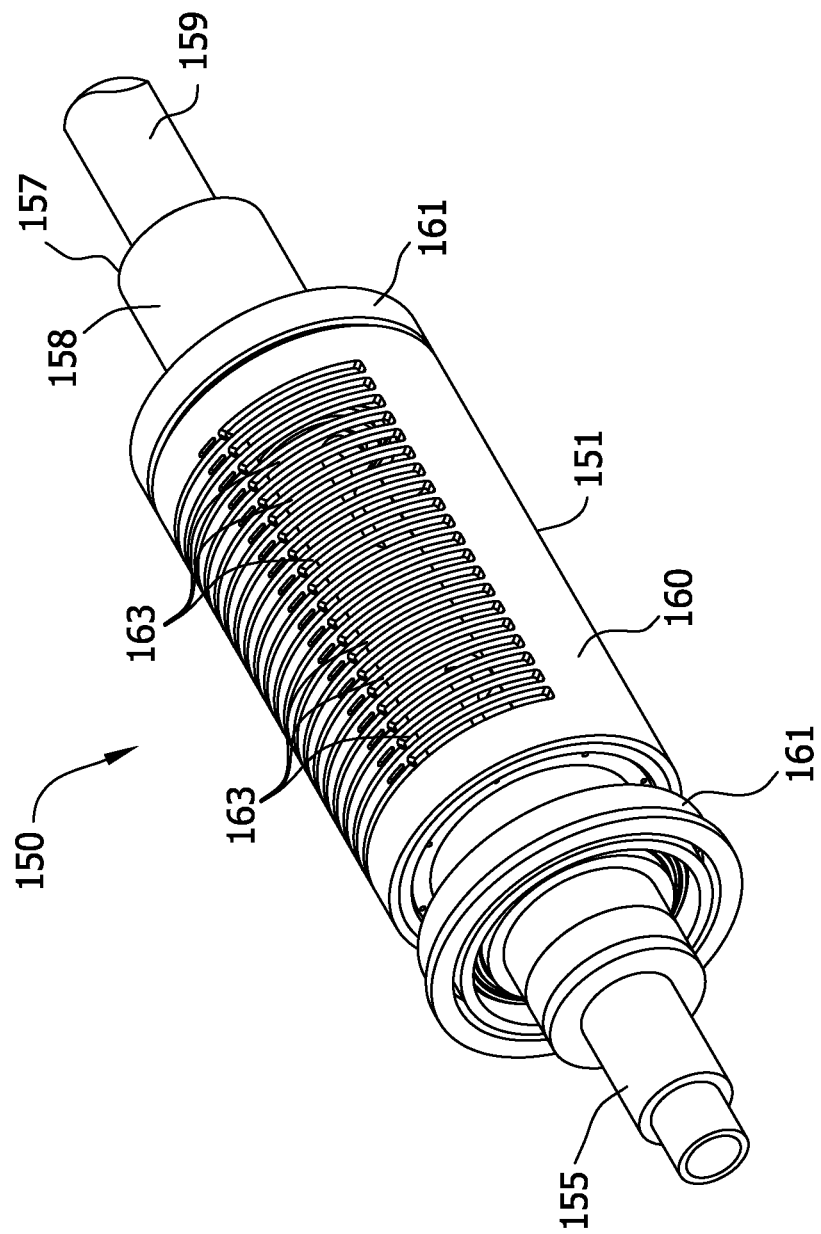
FIG. 18 is a perspective of the oscillating member with an outer cylinder of the oscillating member removed.
Figure 19:
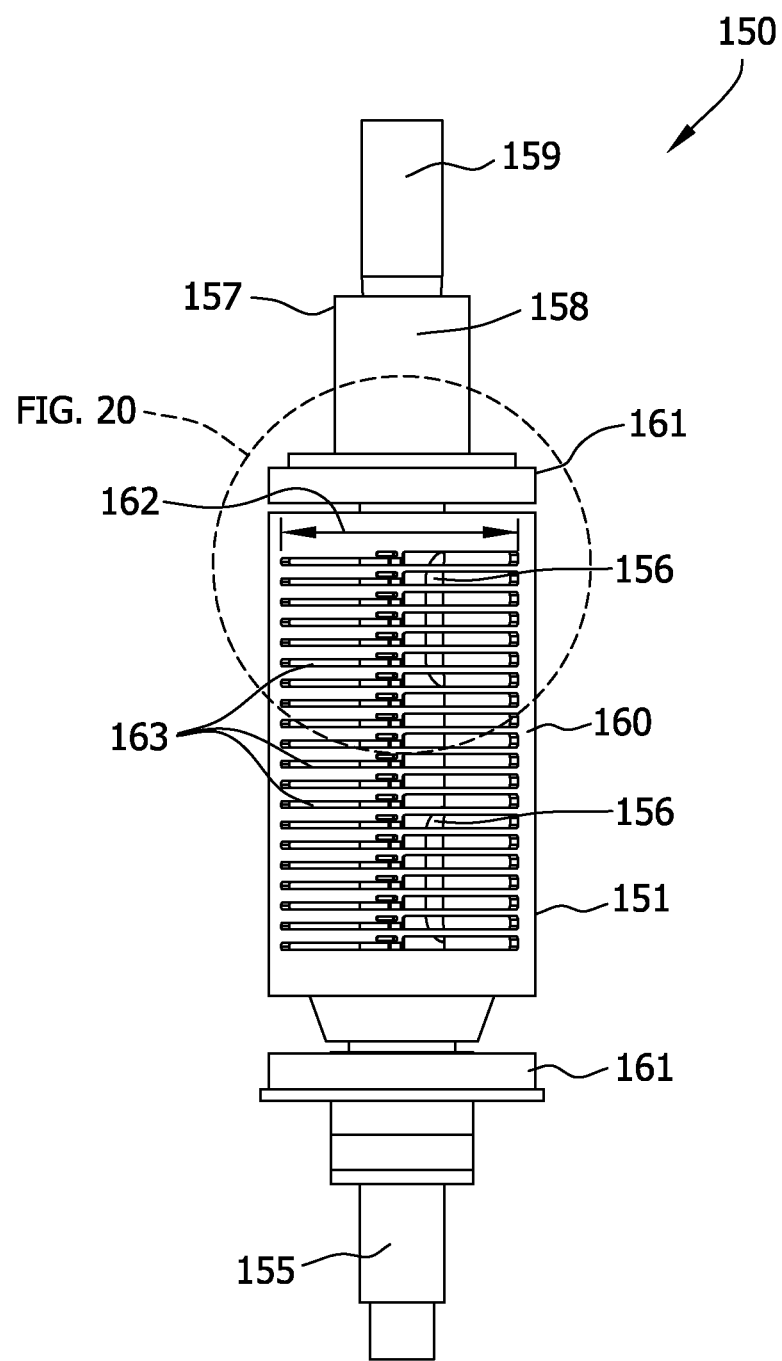
FIG. 19 is a top view of the oscillating member with the outer cylinder removed as seen in FIG. 18.
Figure 20:
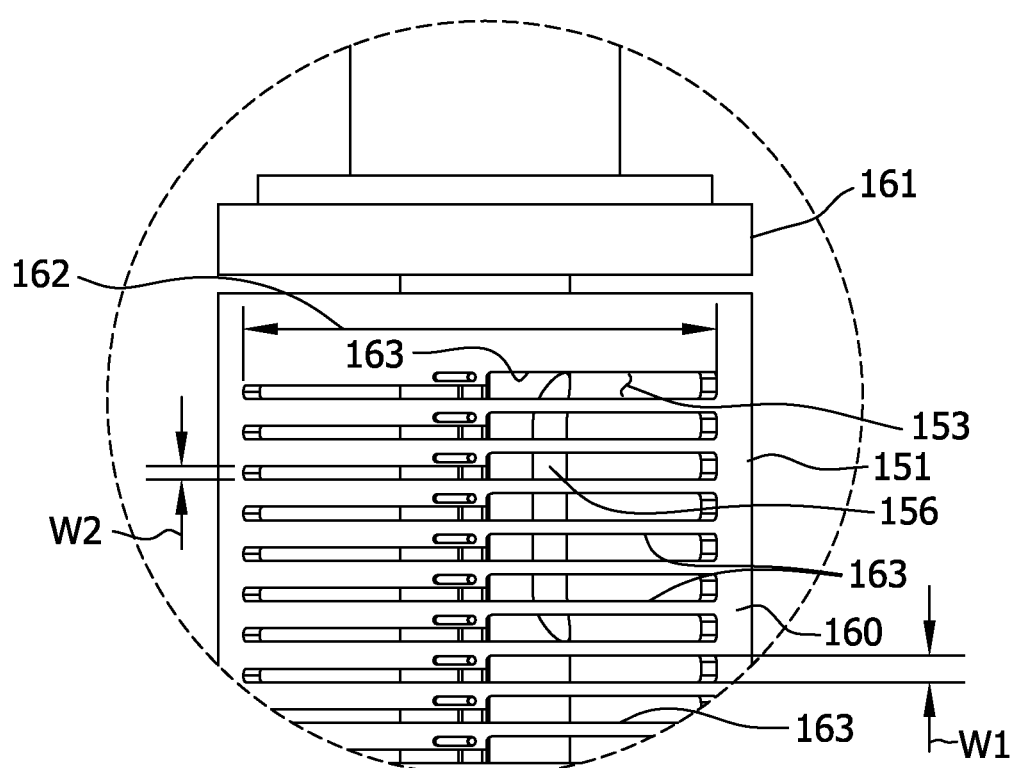
FIG. 20 is an enlarged view of a portion of the oscillating member of FIG. 19.

In the illustrated embodiment, the inner cylinder 151 does not rotate and defines an interior chamber 153 (FIGS. 17 and 20). With reference to FIGS. 18-20, the inner cylinder 151 comprises a wall 160 having a slotted segment 162 with a plurality of slots 163. Each of the slots 163 varies along its length from a first width W1 to a narrower second width W2 (FIG. 20). A pair of end plates 154 is disposed adjacent the ends of the inner cylinder 151 and closes the interior chamber 153 (FIG. 17). A conduit 155 extends into and is in fluid communication with the interior chamber 153 for allowing a suitable vacuum source (not shown) to apply a vacuum thereto. In one suitable embodiment, the conduit 155 extends through the interior chamber 153 and has a pair of oval openings 156 that open within the interior chamber (FIG. 17). It is understood that the conduit 155 may extend only partially into the interior chamber 153 and that the openings 156 in the conduit can vary in shape, size and number.

A drive assembly 157 is operatively connected to the outer cylinder 152 for rotating the outer cylinder with respect to the inner cylinder 151. The drive assembly 157 includes a hub 158, a shaft 159 coupled to the hub and a suitable drive mechanism (not shown) capable of rotating the shaft and the hub.

Figure 21:
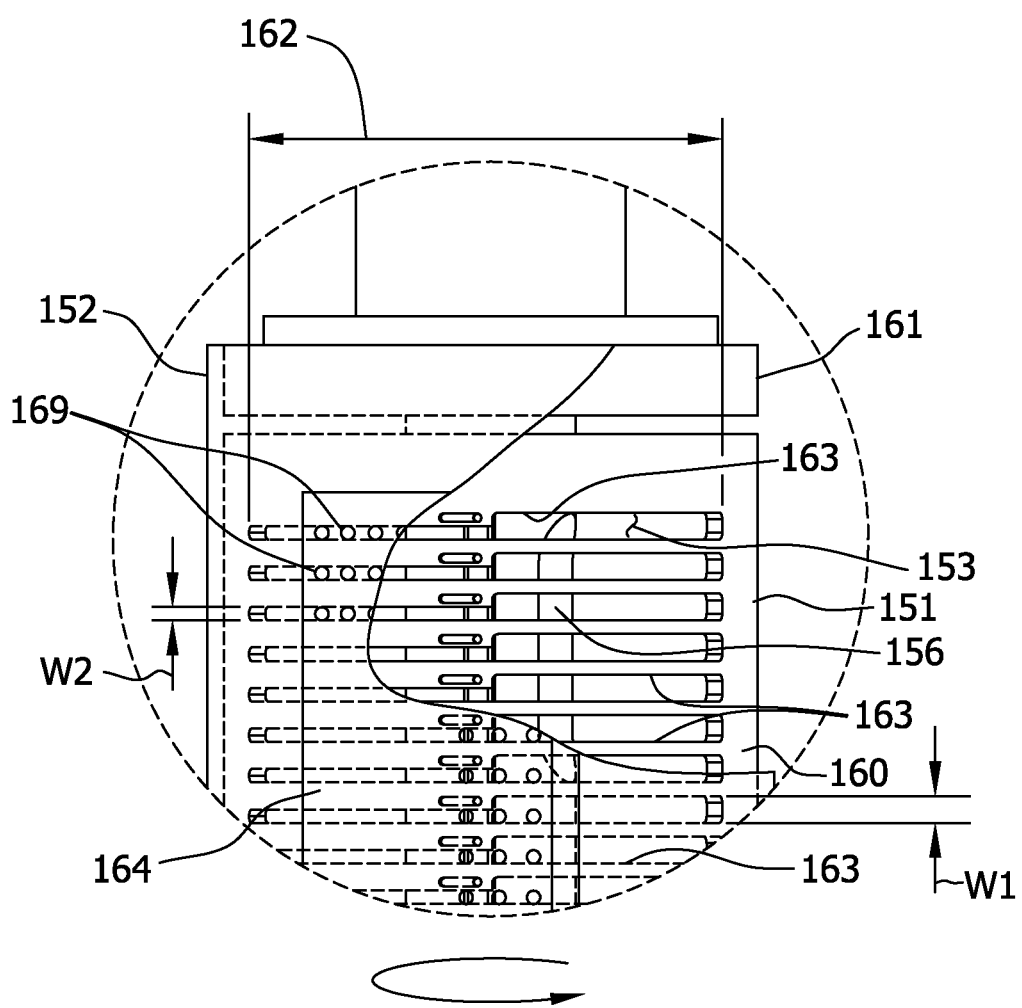
FIG. 21 is a view similar to FIG. 20 but showing the outer cylinder overlying the inner cylinder, the inner cylinder being in a first position and a portion of the outer cylinder being cut away.
Figure 22:
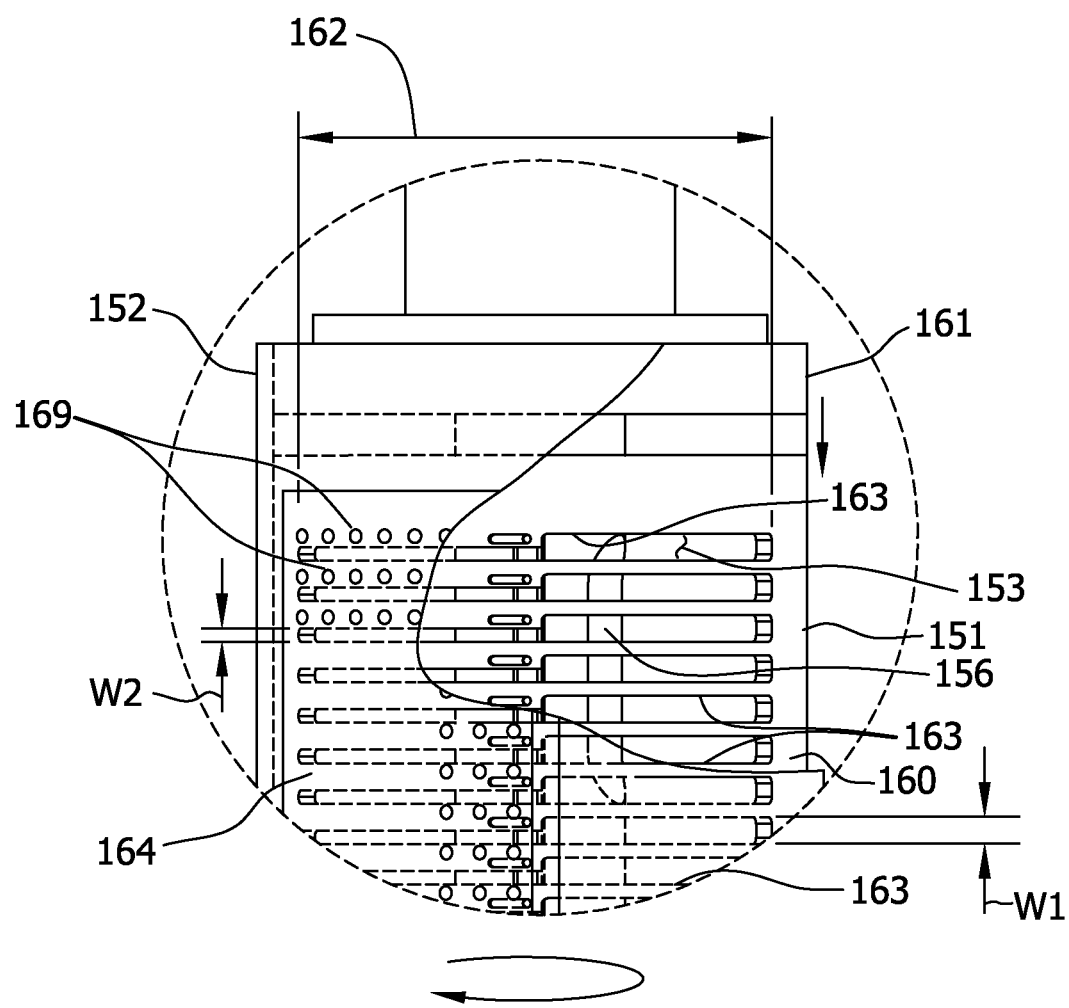
FIG. 22 is a view similar to FIG. 21 but showing the inner cylinder moved relative to the outer cylinder to a second position.
Figure 23:
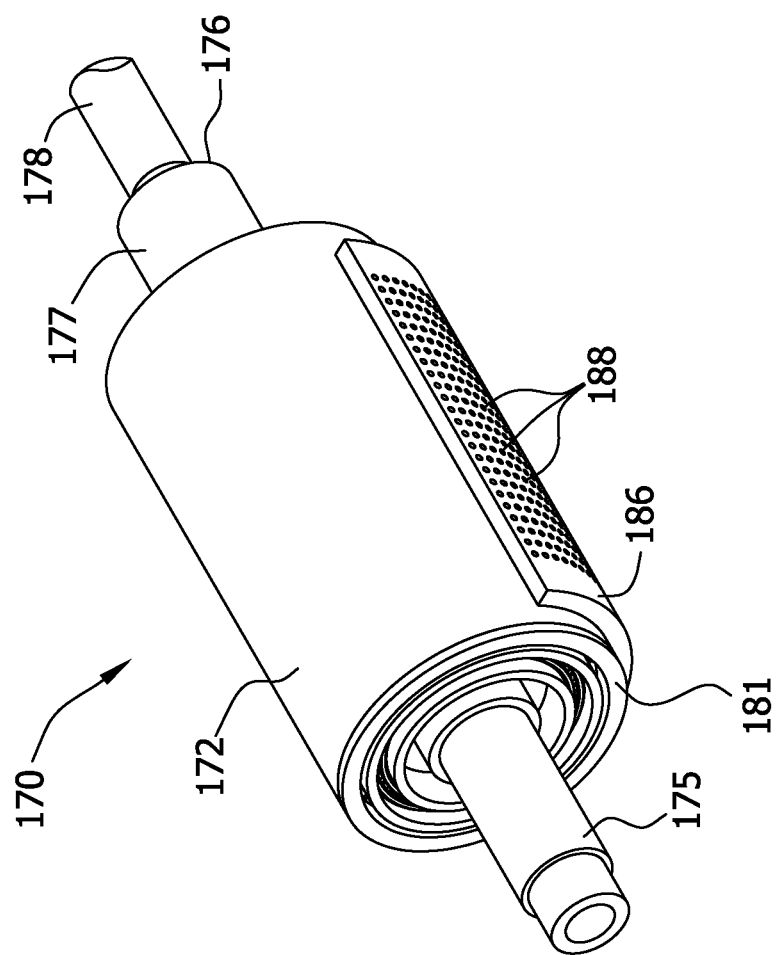
FIG. 23 is a perspective of the folding roll of the folding apparatus.

With reference now to FIGS. 17, 21 and 22, an actuator 168 is provided within the interior chamber 153 of the inner cylinder 151 of the oscillating member for translating the inner cylinder axially with respect to the outer cylinder 152 from a first position to a second position. In the illustrated embodiment, the actuator is adapted to translate the inner cylinder 151 axially (downward as viewed in FIGS. 21 and 22) with respect to the outer cylinder 152.

In the first position, which is illustrated in FIG. 21, the apertures 169 in the puck 164 of the oscillating member 150 are aligned with the slots 163 in the slotted segment 162 of the inner cylinder 151 along their entire length. That is, the apertures 169 in the puck 164 align with both the narrower and wider portions of the slots 163 in the inner cylinder 151. In the second position, however, the apertures 169 in the puck 164 of the oscillating member 150 only align with the wider portion of slots 163 (FIG. 22). Thus, the apertures 169 in the puck 164 of the oscillating member 150 do not align with the narrower portions of the slots 163 when the inner cylinder is in the second position.

As a result, the oscillating member 150 has a first vacuum profile with the inner cylinder 151 in the first position, and a second vacuum profile with the inner cylinder in the second position. That is, the vacuum is turned on and off at different points by the oscillating member when the inner cylinder is in the first position as compared to the inner cylinder being in the second position.

In the illustrated embodiment, the actuator 168 comprises a voice coil motor (FIG. 17). The voice coil motor is capable of developing force in either direction depending upon the polarity of the current applied thereto. Thus, the voice coil motor is capable of braking, damping, and holding forces. In one suitable embodiment, the voice coil motor is capable of displacing more than 15 mm at frequencies up to 40 or 50 Hz. In the illustrated embodiment, for example, the input current is preset so that the voice coil motor displaces the inner cylinder 151 approximately 5 millimeters (mm). More specifically, the voice coil motor is illustrated in its normal position in FIG. 21, which corresponds to the first position of the inner cylinder 151. When the preset input current is applied to the voice coil motor, the voice coil motor acts on the inner cylinder 151 to translate the inner cylinder approximately 5 mm with respect to the outer cylinder 152. In other words, the voice coil motor moves the inner cylinder 151 to the second position. It is contemplated that the inner cylinder 151 can move more or less than 5 mm with respect to the outer cylinder 152. It is understood that other types of suitable actuators besides voice coil motors can be used to move the inner cylinder 151 relative to the outer cylinder 152.

Figure 24:
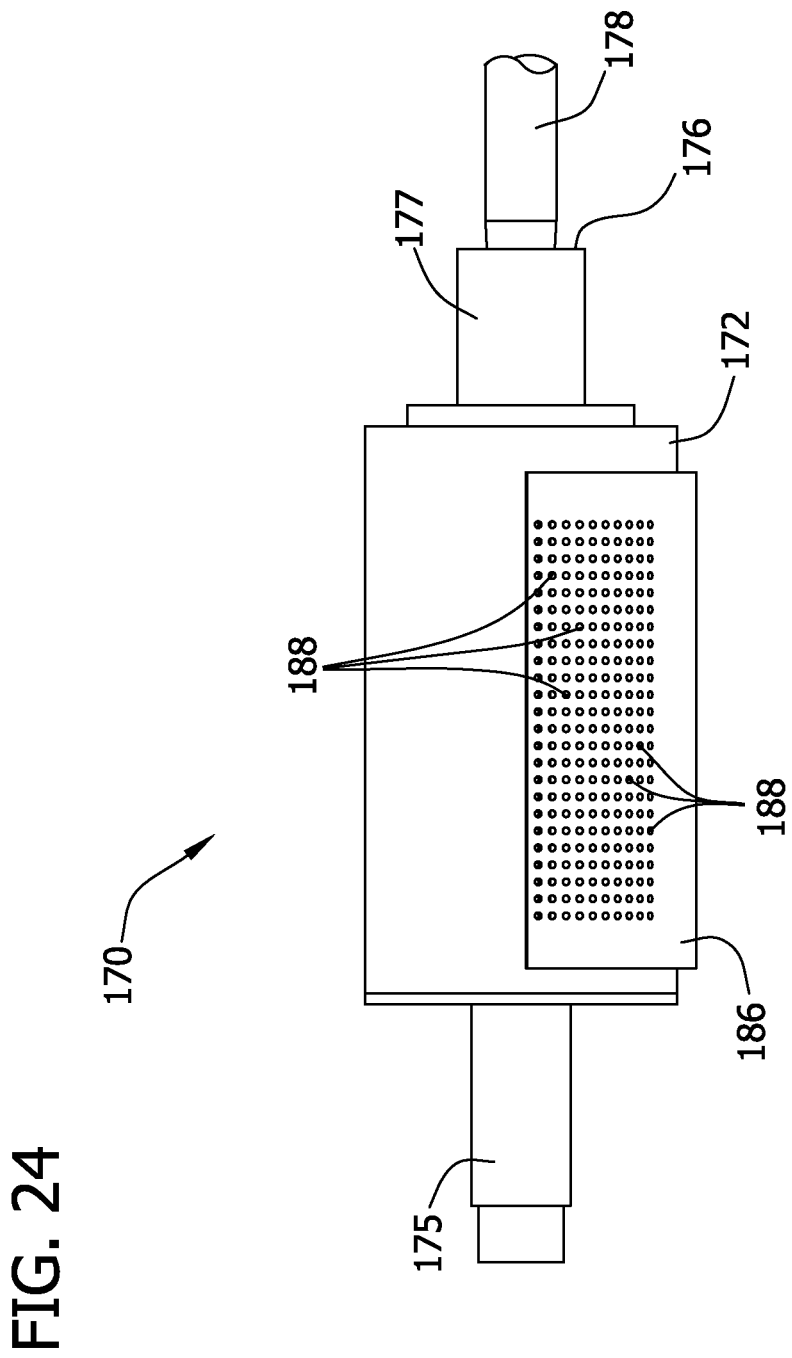
FIG. 24 is a right side view of the folding roll as seen in FIG. 23.
Figure 25:
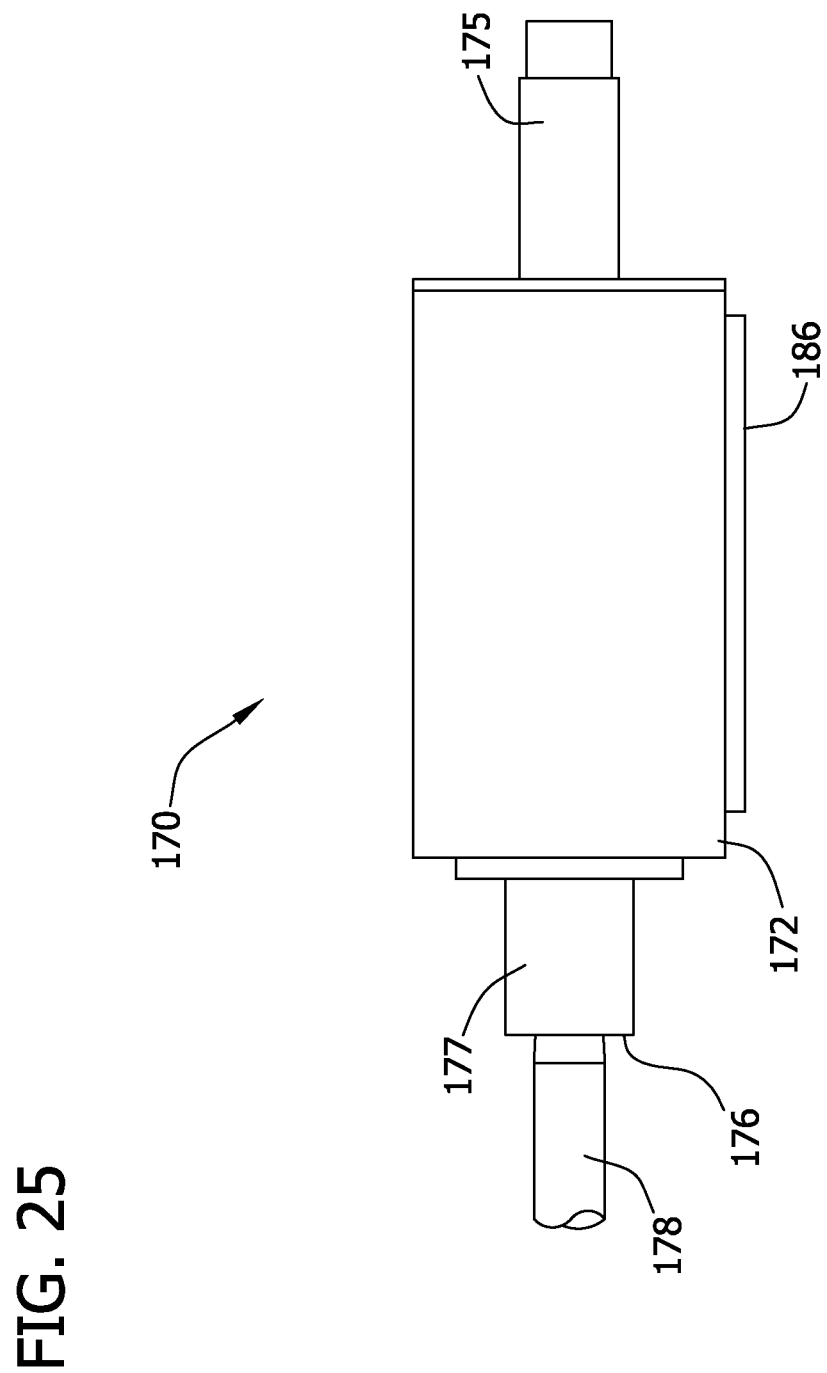
FIG. 25 is a left side view of the folding roll.
Figure 26:
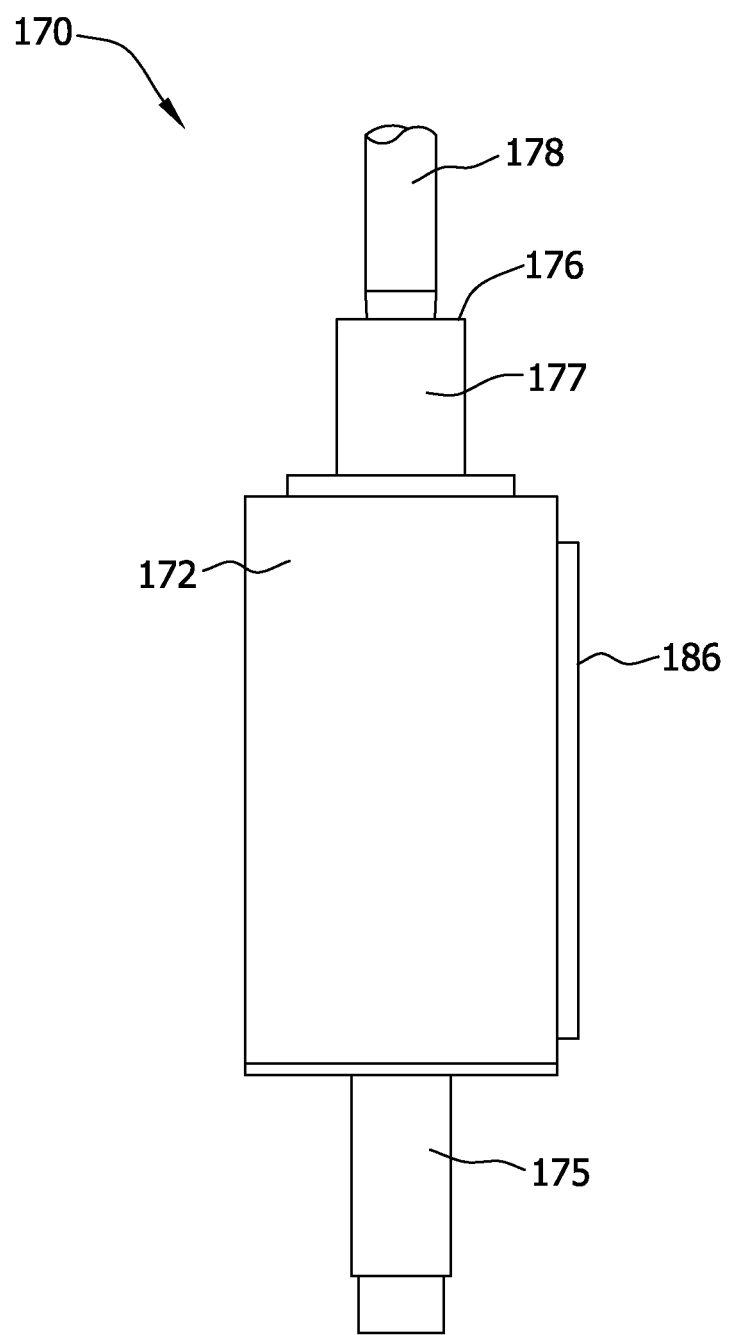
FIG. 26 is a bottom view of the folding roll.
Figure 27:
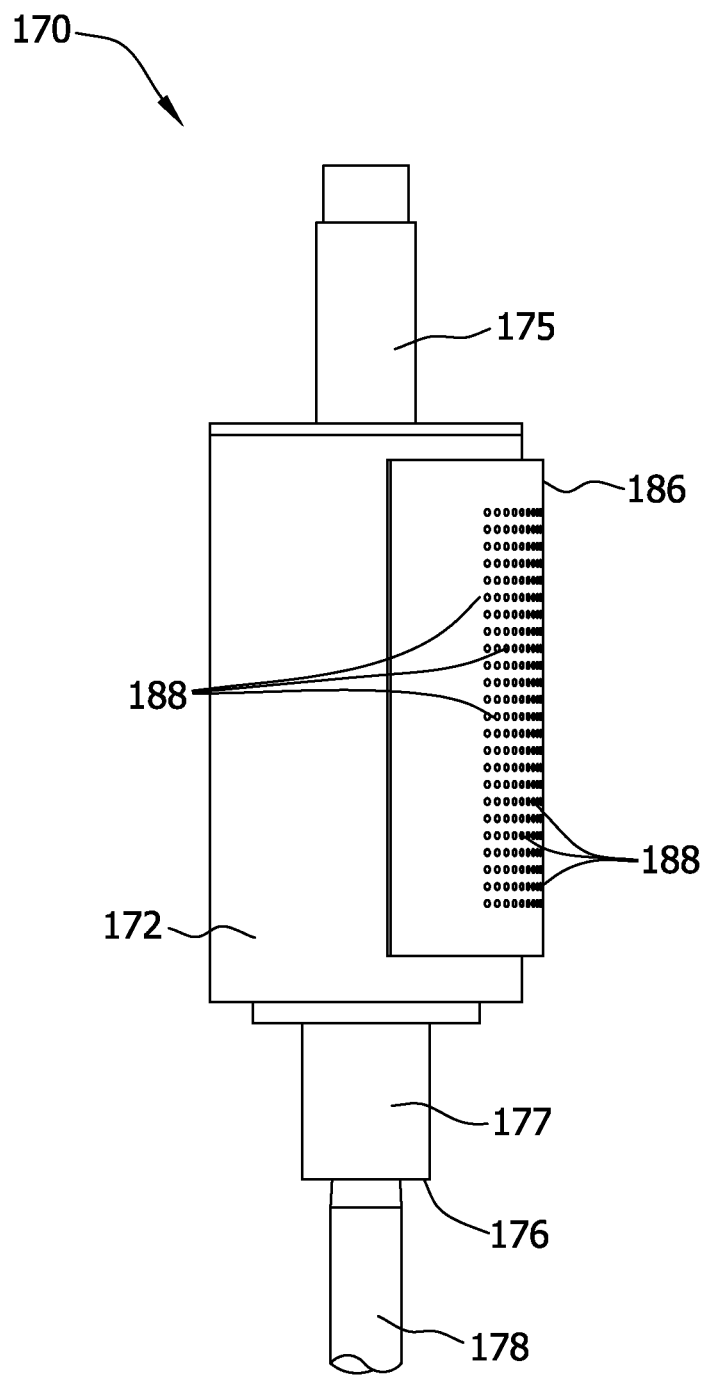
FIG. 27 is a top view of the folding roll.
Figure 28:
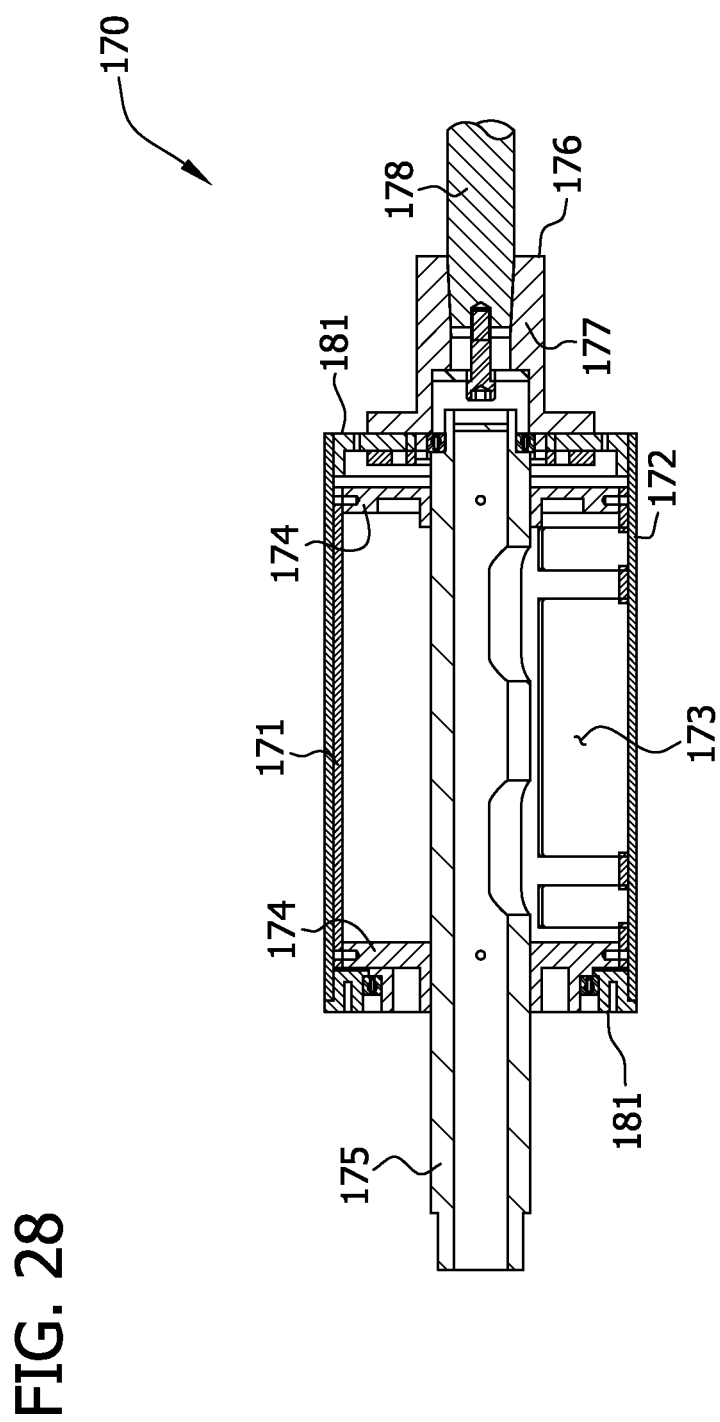
FIG. 28 is a vertical cross-section of the folding roll.

As illustrated in FIGS. 23-30, the folding roll 170 comprises an inner cylinder 171 and an outer cylinder 172 that is rotatable about the inner cylinder. As seen in FIGS. 23-27, the outer cylinder 172 comprises a raised puck 186 adapted to receive the portion of the training pant 500 from the oscillating member 150 and to transfer the portion to the receiving roll 110. The raised puck 186 includes a plurality of circular apertures 188 arranged generally in a rectangle (FIG. 24). It is understood, however, that the raised puck 186 can be flush with the remainder of the outer cylinder 172 (i.e., not raised). It is further understood that the apertures 188 in the puck 186 of the outer cylinder 172 can be arranged differently, that there could be more or fewer apertures than illustrated in the accompanying drawings, and that the apertures can have different shapes and sizes than those illustrated. The outer cylinder 172 is closed by a pair of end plates 181 (FIG. 28).

Figure 29:
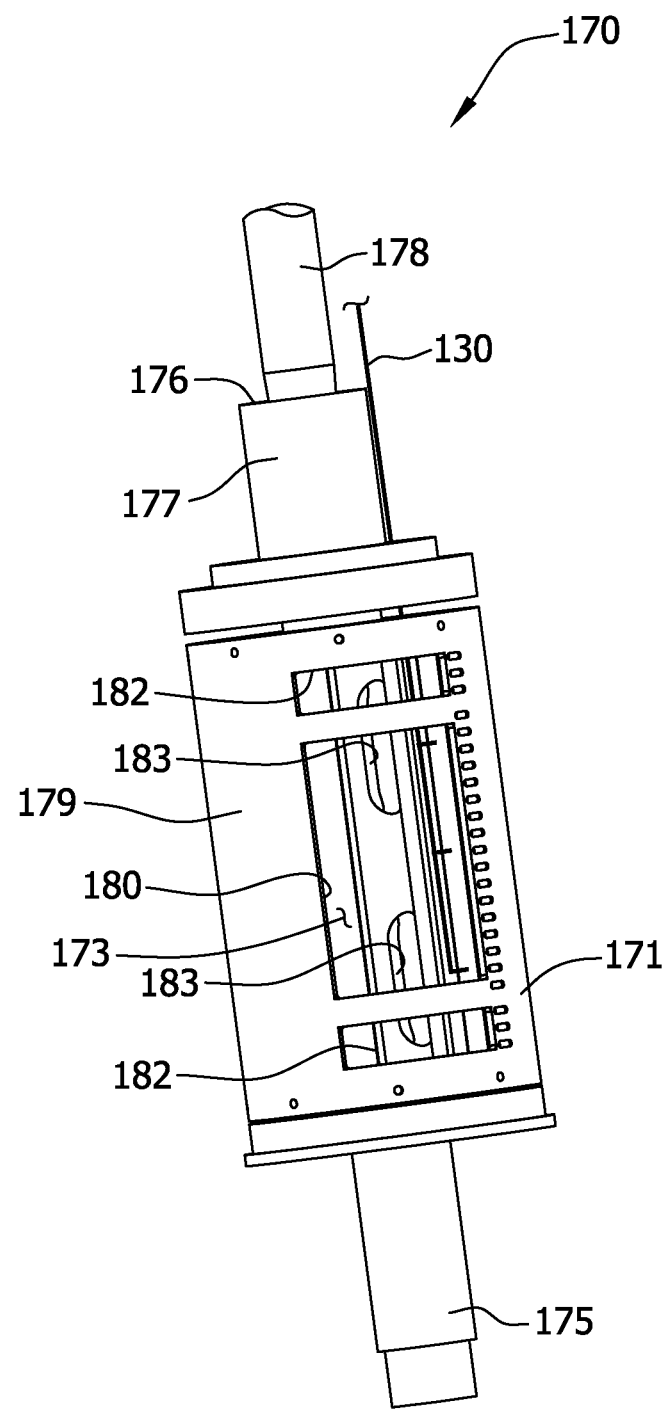
FIGS. 29 and 30 are perspectives of the folding roll with an outer cylinder of the folding roll removed.
Figure 30:
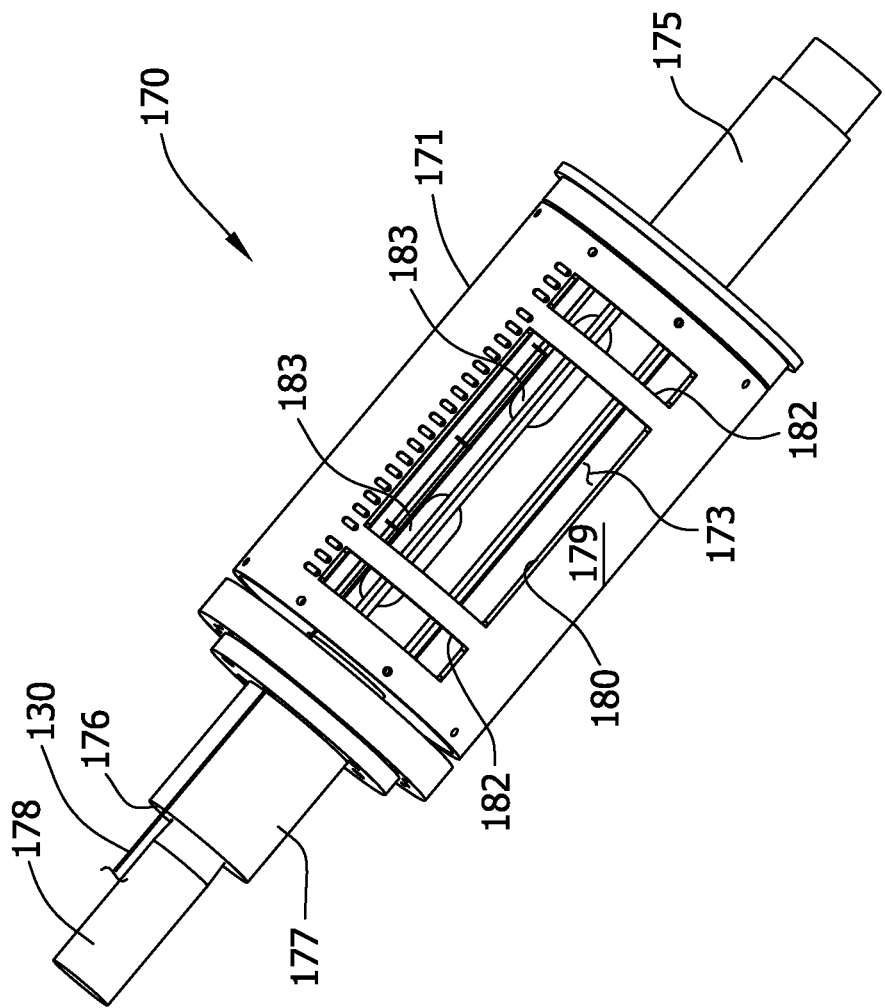
Figure 31:
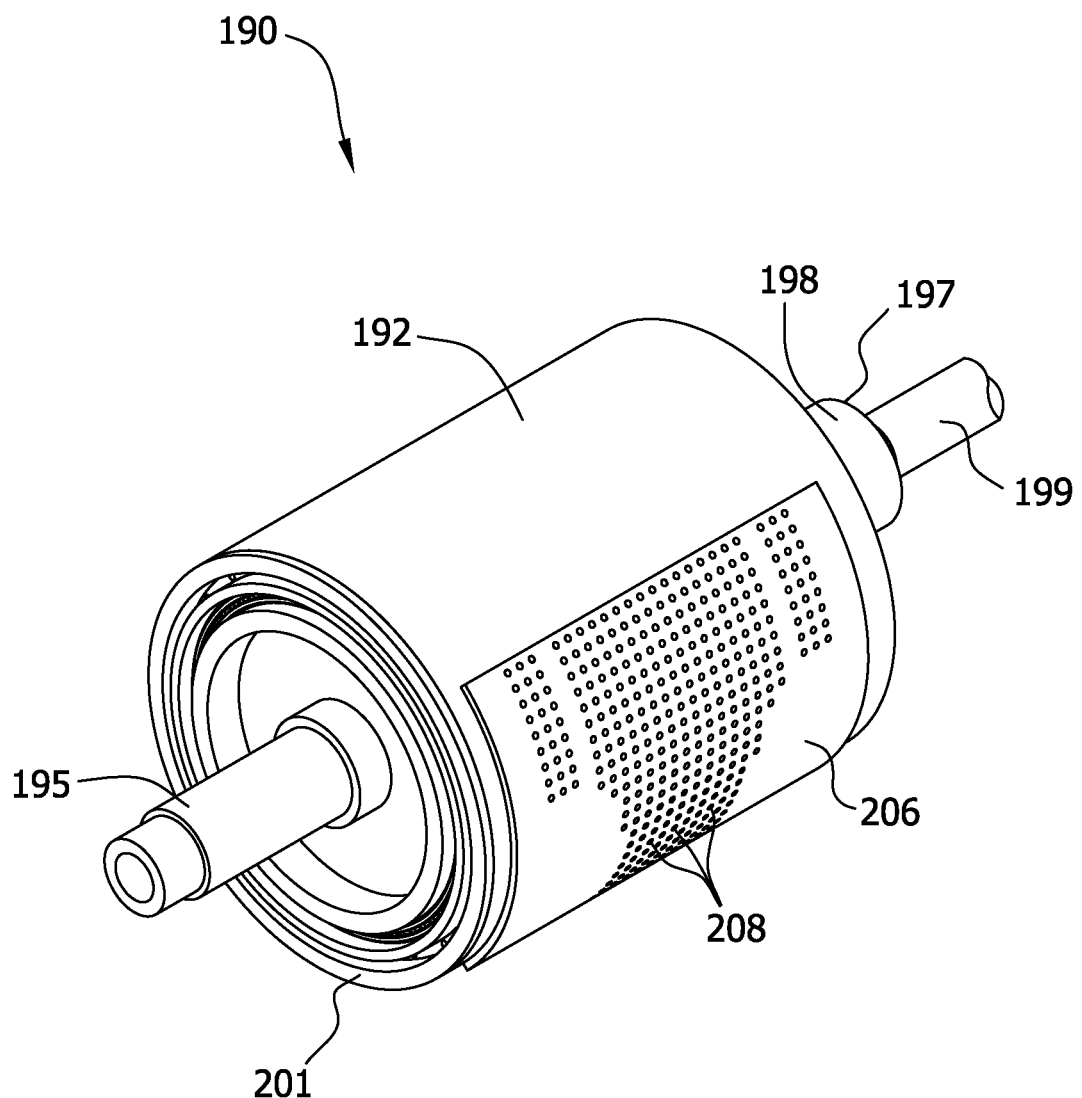
FIG. 31 is a perspective of the transferring roll of the folding apparatus.

In the illustrated embodiment, the inner cylinder 171 is stationary and defines an interior chamber 173 (FIGS. 28-30). As illustrated in FIGS. 29 and 30, the inner cylinder 171 comprises a wall 179 having a primary rectangular opening 180 and pair of secondary rectangular openings 182 flanking the primary opening. It is understood that the openings 180, 182 in the inner cylinder 171 can have other shapes and configurations than rectangular and that the second openings can be omitted. A pair of end plates 174 are disposed adjacent the ends of the inner cylinder 171 and closes the interior chamber 173 (FIG. 28). A conduit 175 extends into and is in fluid communication with the interior chamber 173 for allowing a suitable vacuum source (not shown) to apply a vacuum thereto. In the illustrated embodiment, the conduit 175 extends through the interior chamber 173 and has a pair of oval openings 183 that opens within the interior chamber (FIGS. 29 and 30). It is understood that the conduit 175 may extend only partially into the interior chamber and that the openings in the conduit can vary in shape, size and number.

A drive assembly 176 is operatively connected to the outer cylinder 172 for rotating the outer cylinder with respect to the inner cylinder 171. The drive assembly 176 includes a hub 177, a shaft 178 coupled to the hub, and a suitable drive mechanism (not shown) capable of rotating the shaft and hub.

Figure 32:
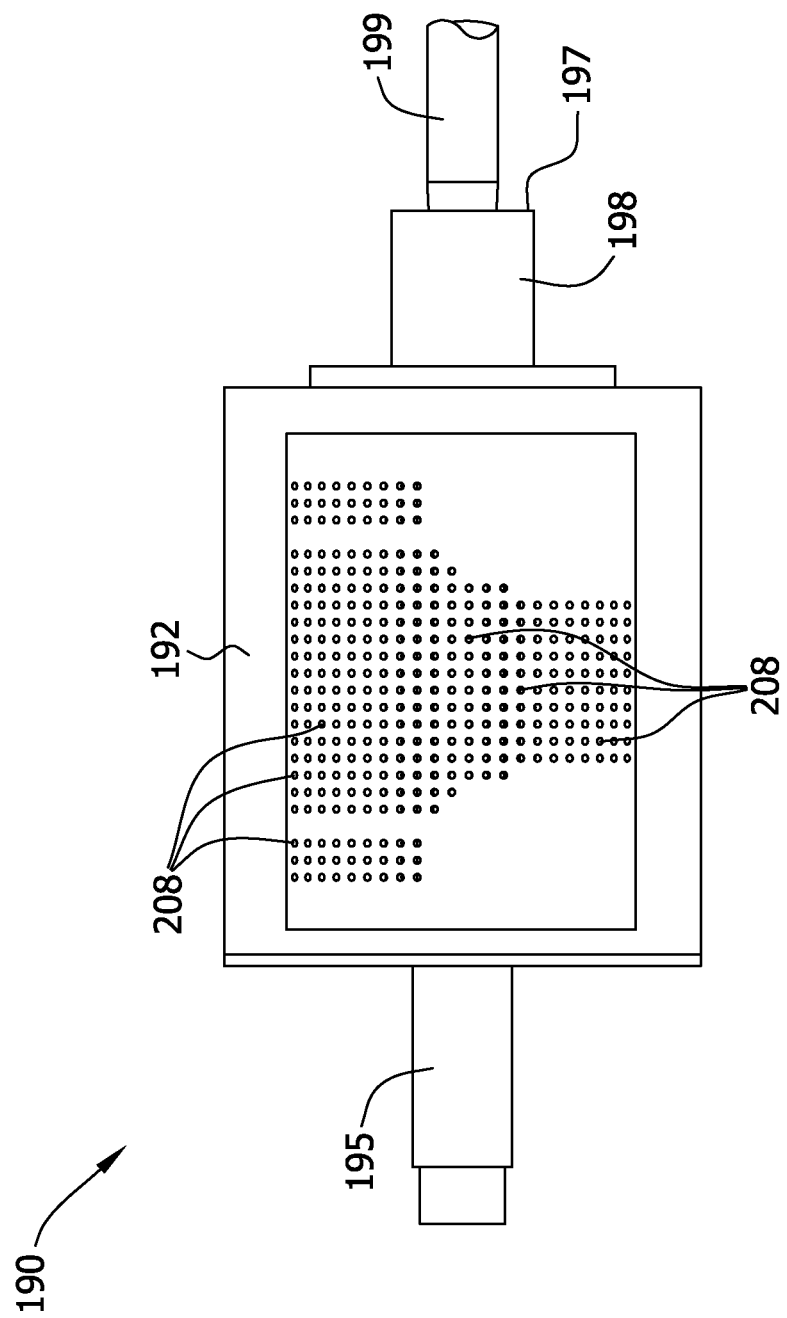
FIG. 32 is a right side view of the transferring roll as seen in FIG. 31.
Figure 33:
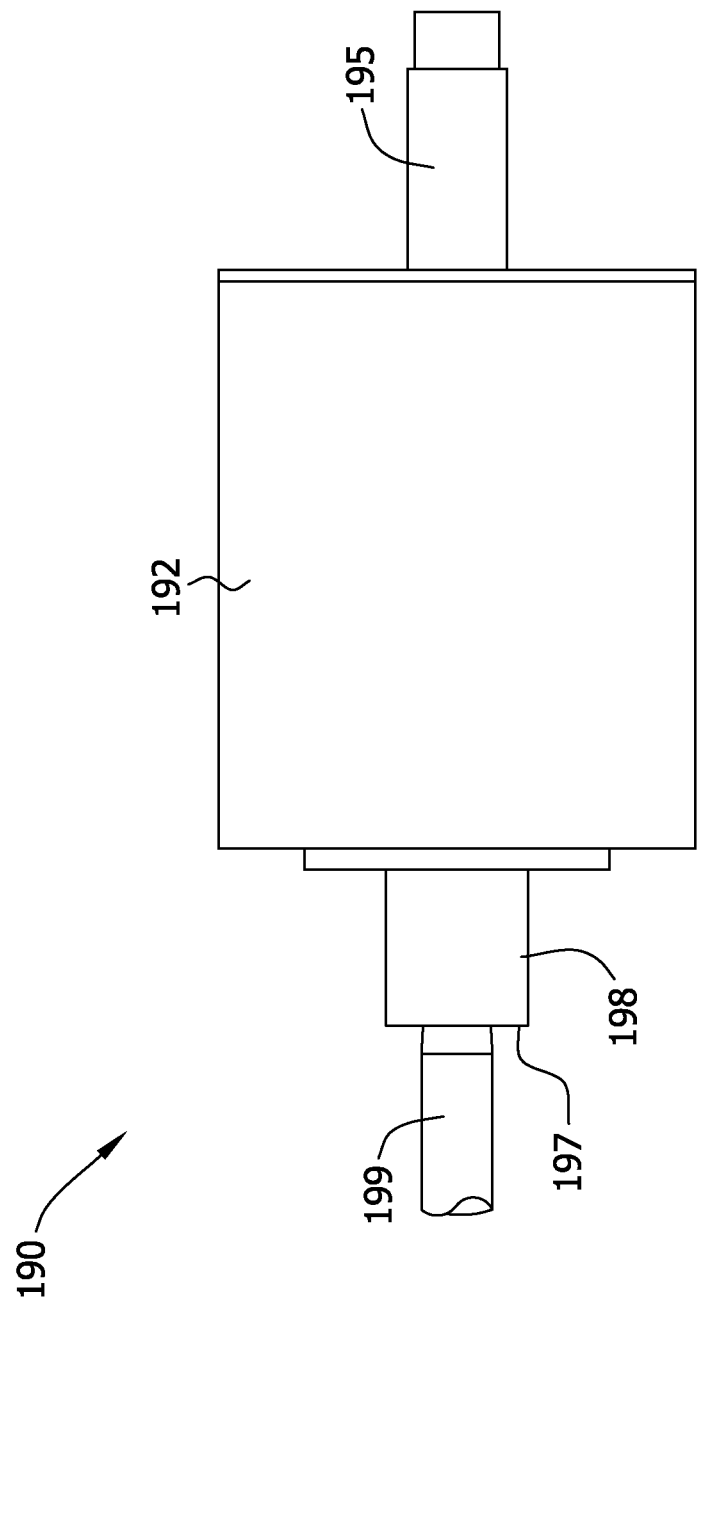
FIG. 33 is a left side view of the transferring roll.
Figure 34:
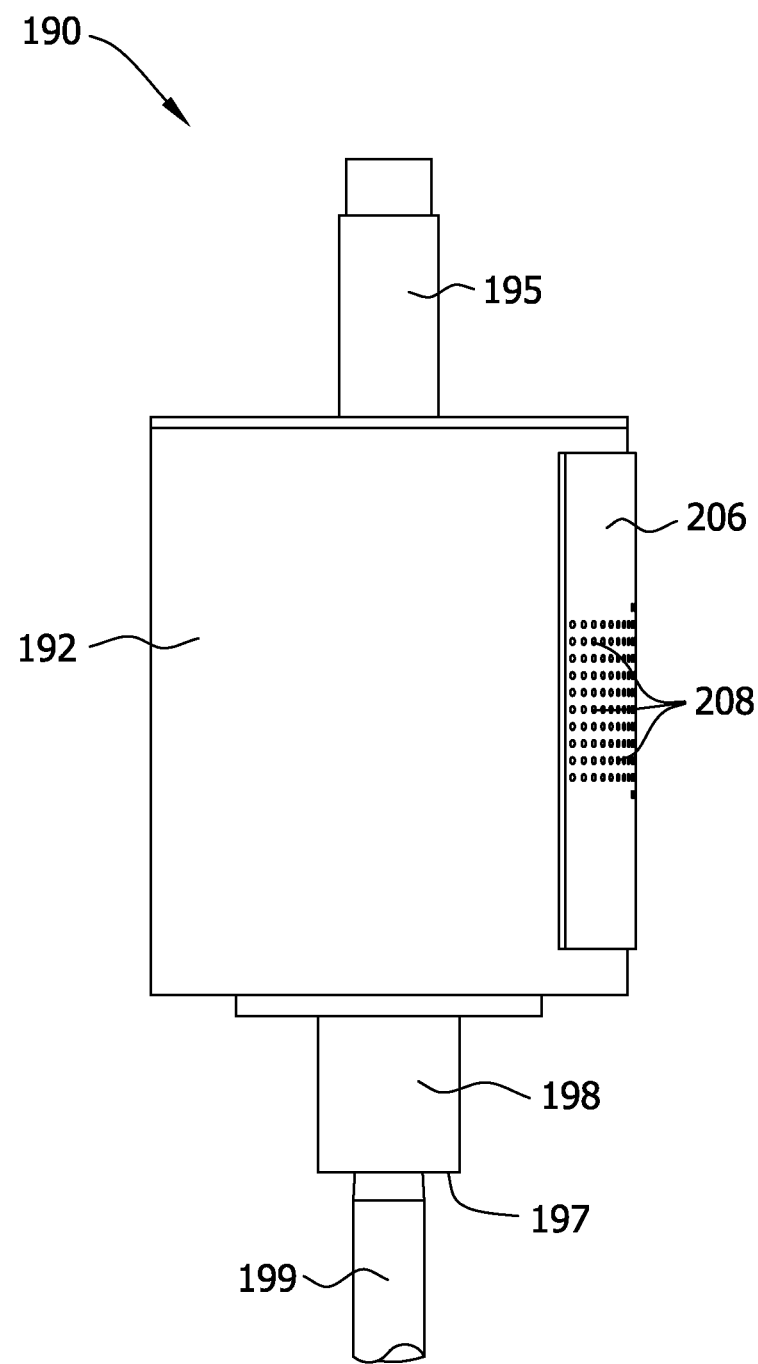
FIG. 34 is a bottom view of the transferring roll.
Figure 35:
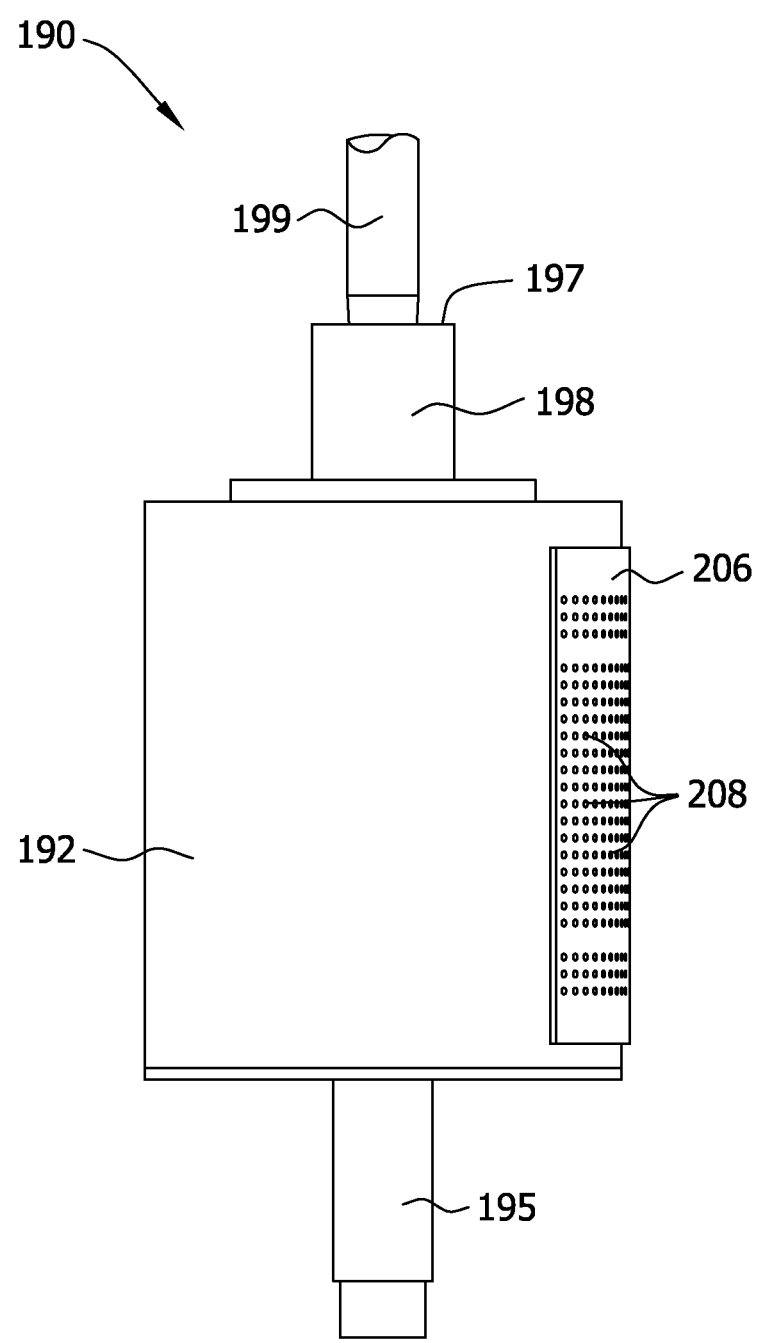
FIG. 35 is a top view of the transferring roll.
Figure 36:
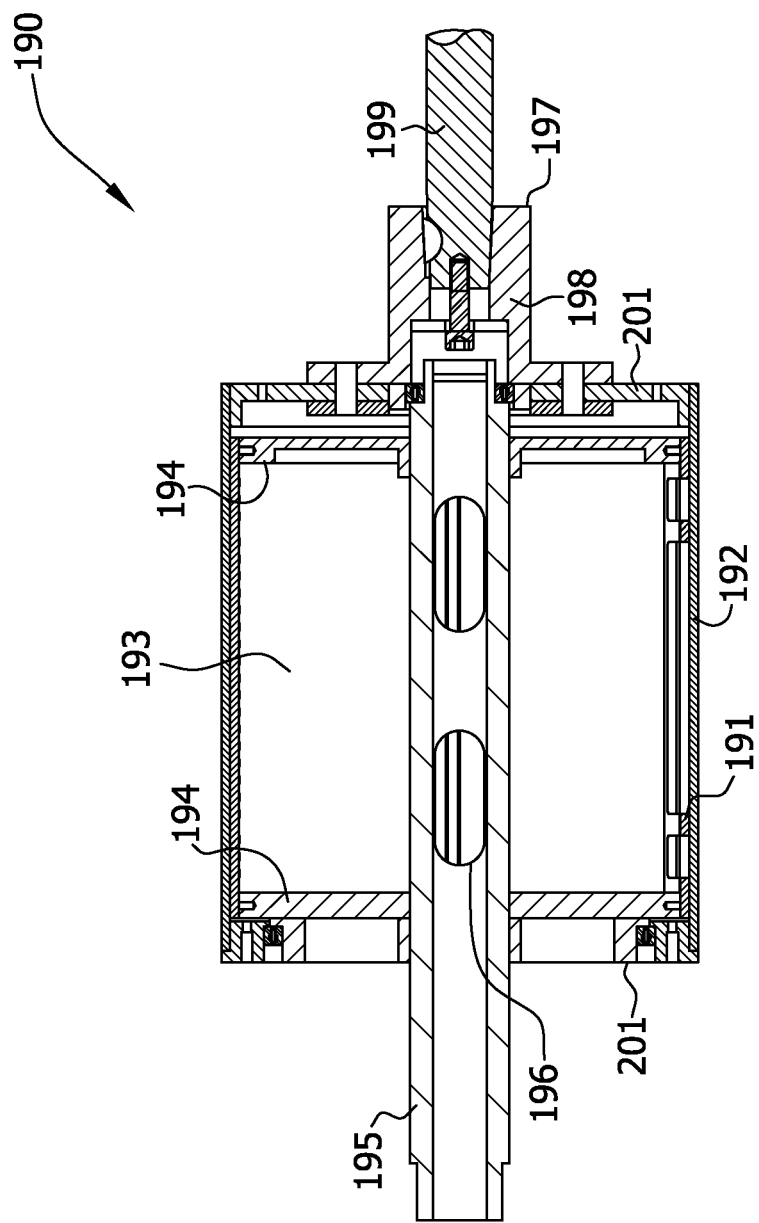
FIG. 36 is a vertical cross-section of the transferring roll.

As seen in FIGS. 31-38, the transferring roll 190 comprises an inner cylinder 191 and an outer cylinder 192 that is rotatable about the inner cylinder. With references to FIGS. 32, 34, and 35, the outer cylinder 192 comprises a raised engagement member 206 adapted to receive the training pant 500 in its folded configuration from the receiving roll 110. The raised engagement member 206 includes a plurality of circular apertures 208 arranged generally in the profile of the training pant 500 in its folded configuration (FIG. 32). It is understood, however, that the raised engagement member 206 can be flush with the remainder of the outer cylinder 192 (i.e., not raised). It is further understood that the apertures 208 in the engagement member 206 of the outer cylinder 192 can be arranged differently, that there could be more or fewer apertures than illustrated in the accompanying drawings, and that the apertures can have different shapes and sizes than those illustrated. The outer cylinder 192 is closed by a pair of end plates 201 (FIG. 36).

Figure 37:
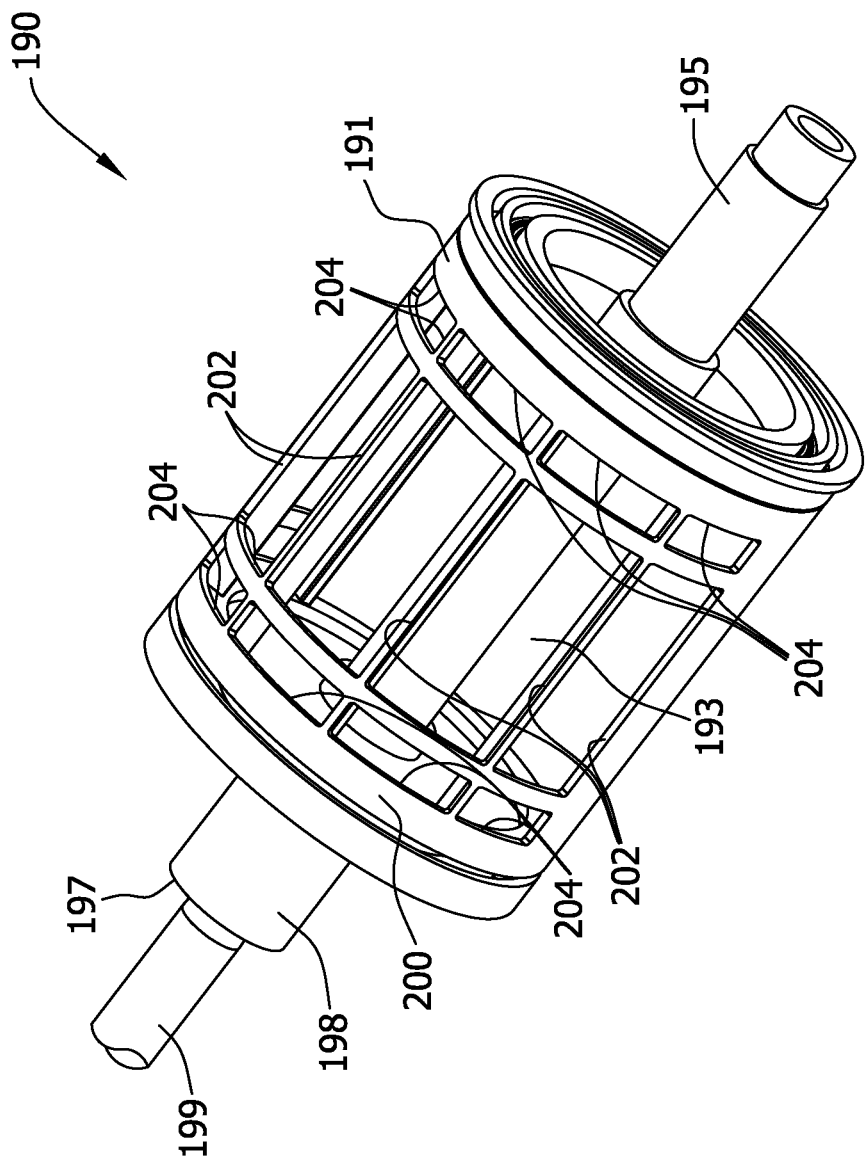
FIG. 37 is a perspective of the transferring roll with an outer cylinder of the transferring roll removed.
Figure 38:
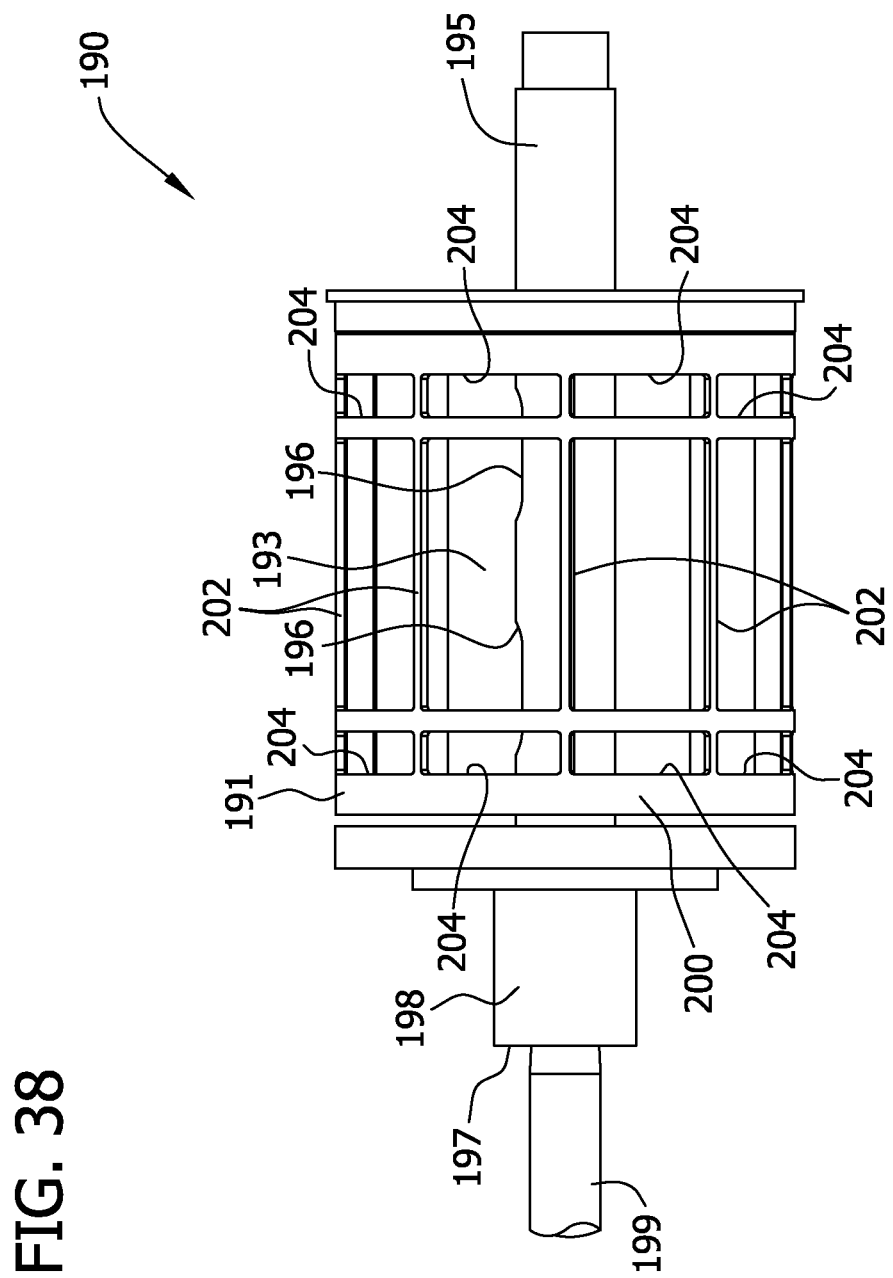
FIG. 38 is a top view of the transferring roll with the outer cylinder removed.

In the illustrated embodiment, the inner cylinder 191 is stationary and defines an interior chamber 193 (FIGS. 36-38). As seen in FIGS. 37 and 38, the inner cylinder 191 comprises a wall 200 having five primary rectangular openings 202 with each of the primary rectangular openings being flanked by a pair of secondary rectangular openings 204. A pair of end plates 194 are disposed adjacent the ends of the inner cylinder 191 and closes the interior chamber 193 (FIG. 38). A conduit 195 extends into and is in fluid communication with the interior chamber 193 for allowing a suitable vacuum source (not shown) to apply a vacuum thereto. In one suitable embodiment, the conduit 195 extends through the interior chamber 193 and has a pair of oval openings 196 that opens within the interior chamber (FIGS. 36 and 38). It is understood that the conduit 195 may extend only partially into the interior chamber 193 and that the openings 196 in the conduit can vary in shape, size and number.

A drive assembly 197 is operatively connected to the outer cylinder 192 for rotating the outer cylinder with respect to the inner cylinder 191. The drive assembly 197 includes a hub 198, a shaft 199 coupled to the hub, and a suitable drive mechanism (not shown) capable of rotating the shaft and the hub.

Each of the receiving roll 110, the oscillating member 150, the folding roll 170 and the transferring roll 190 are described herein as using vacuum to hold the training pant 500 to their respective outer cylinder. Thus, each one of the illustrated receiving roll 110, the oscillating member 150, the folding roll 170 and the transferring roll 190 can broadly be referred to as a vacuum roll. It is contemplated, however, that other suitable structure (e.g., adhesive, frictional members, nanofabricated hairs) capable of grasping, controlling, and releasing the training pant 500 can be used instead.

Figure 39:
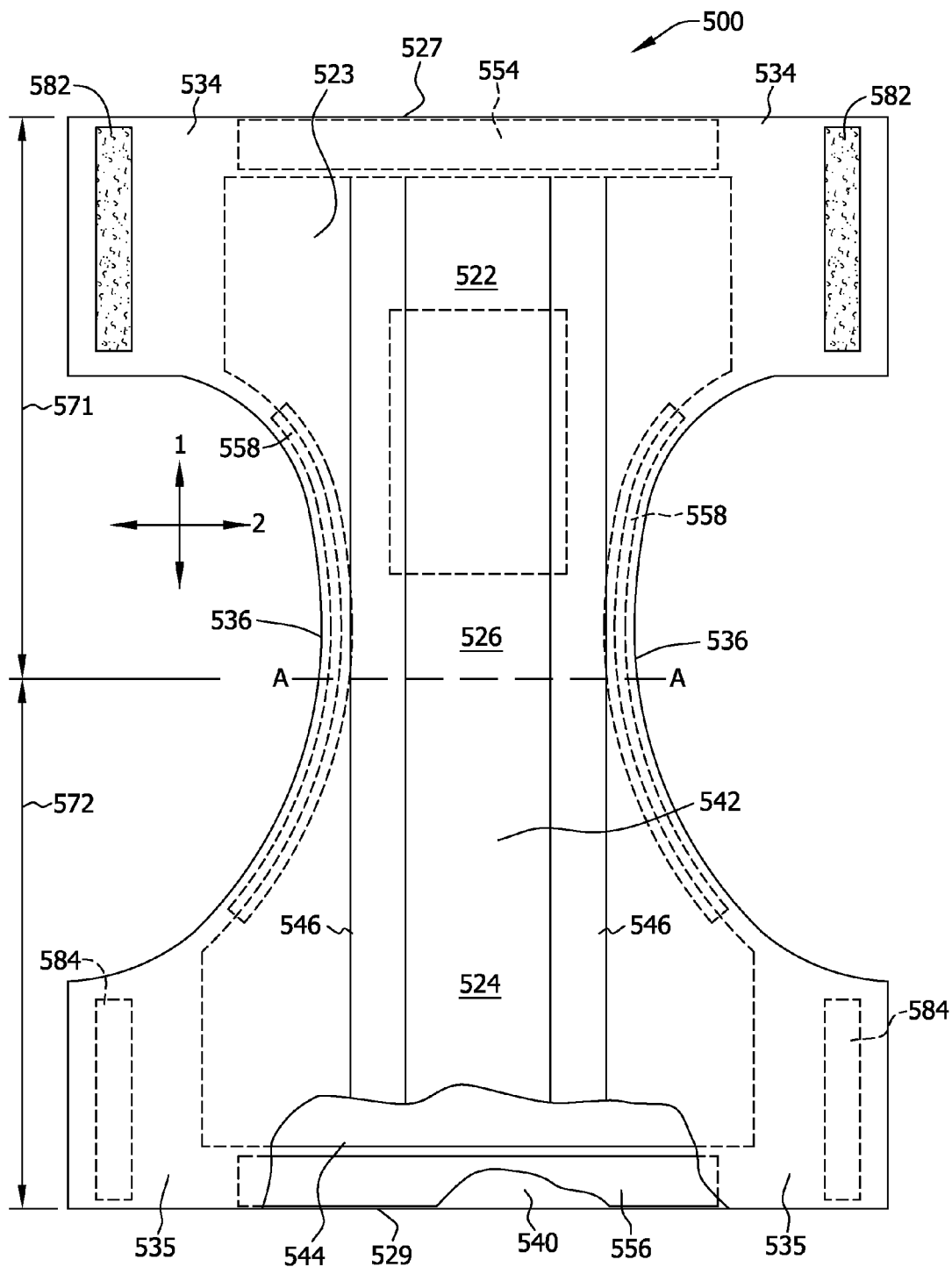
FIG. 39 is a top view of a training pant in a prefolded, laid-flat configuration with portions of the training pant being cut-away.
Figure 40:
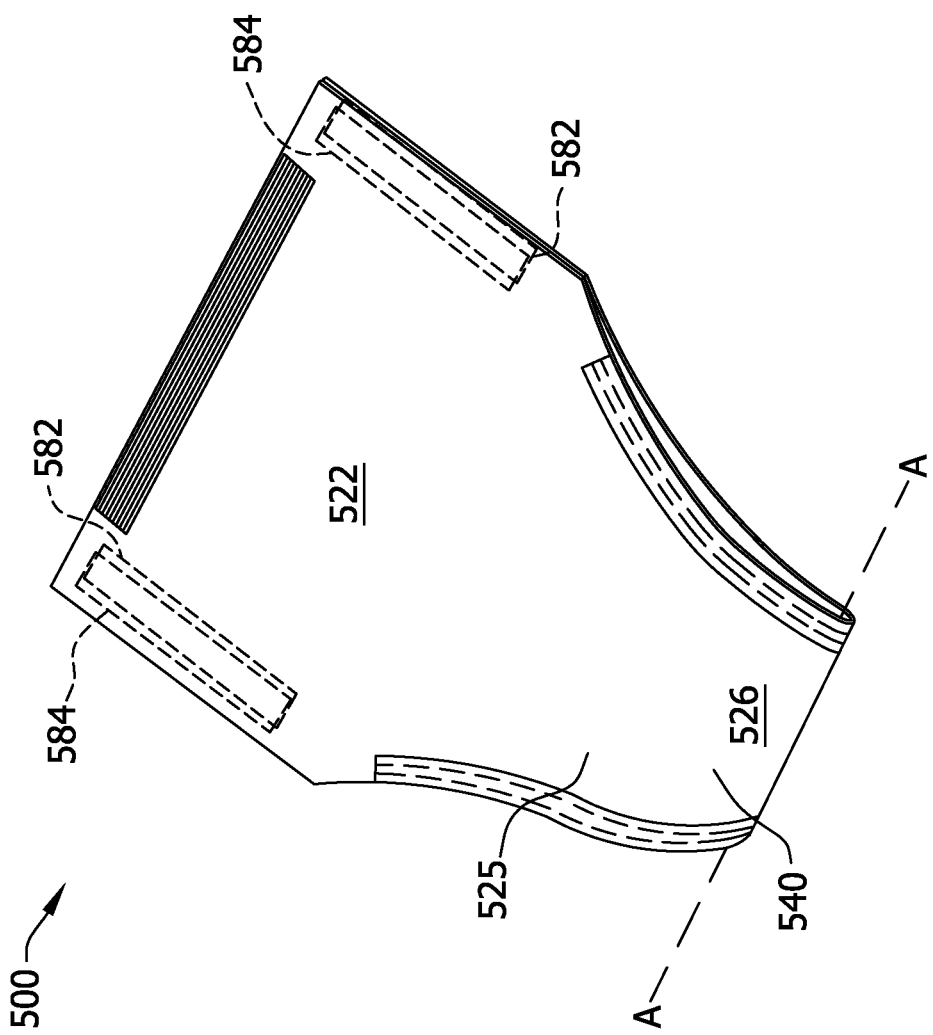
FIG. 40 is a top view of the training pant of FIG. 39 in a folded configuration.
Figure 41:
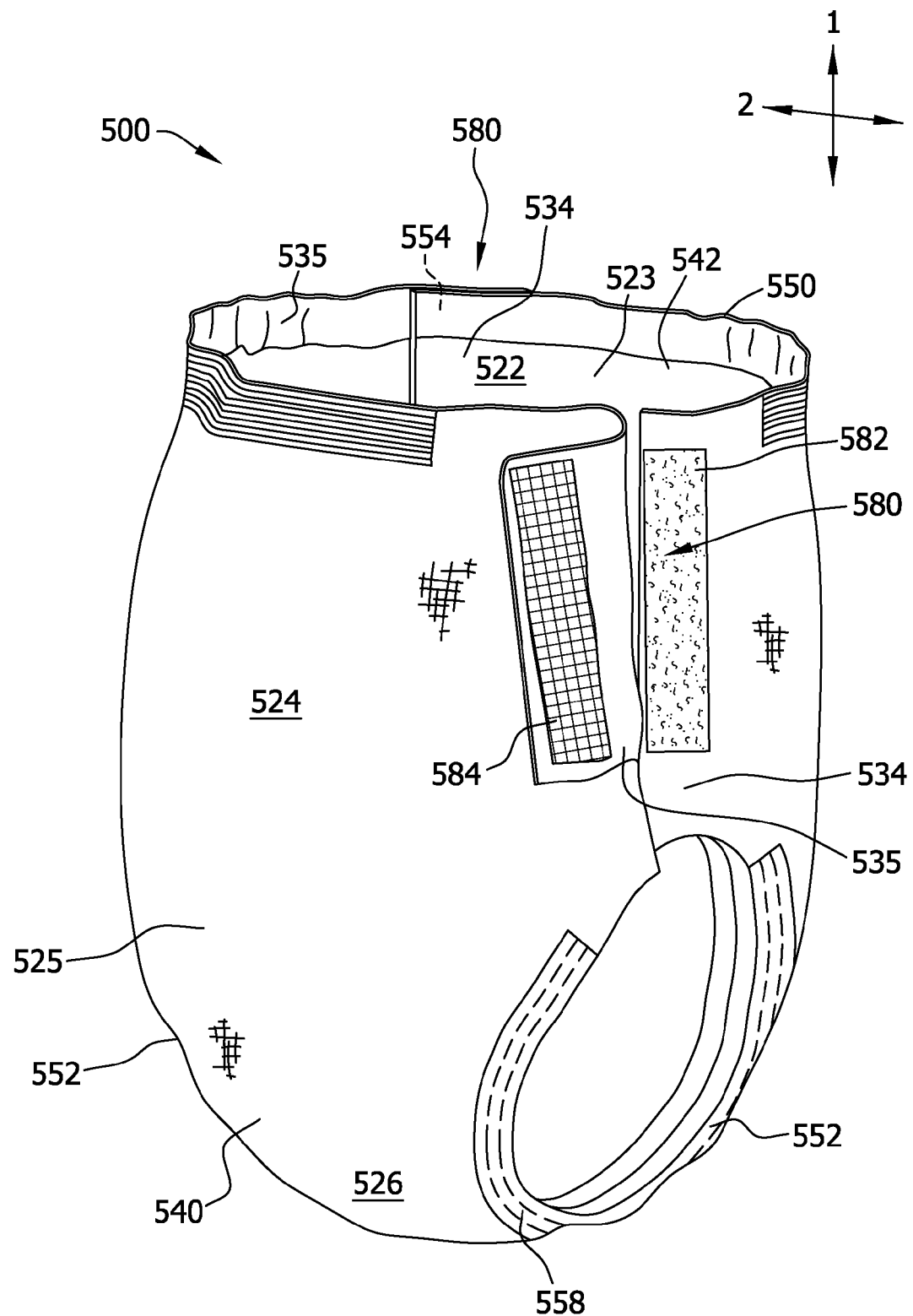
FIG. 41 is a perspective of the training pant in a partially fastened ready-to-use configuration.

As mentioned above, the manufacturing system 50 schematically illustrated in FIG. 1 and the folding apparatus 100 can be used to manufacture and fold training pants 500, which are well-known in the art. FIGS. 39-41 illustrate one embodiment of a known training pant 500 suitable for being manufactured and folded by the described manufacturing system 50 and the folding apparatus 100. The training pant 500 is illustrated in FIG. 39 in its pre-folded, laid-flat configuration. It should be understood that a "pre-folded configuration" is not limited to a training pant having no folds, but rather refers to a training pant entering the folding apparatus 100 (i.e., the training pant has not yet been folded specifically by the folding apparatus). Accordingly, the training pant 500 may or may not comprise additional folds or folded portions prior to entering the folding apparatus 100. FIG. 40 illustrates the training pant 500 in its folded configuration, i.e., after it has been folded by the folding apparatus 100. By "folded configuration" it is meant that the training pant 500 has been folded specifically by the folding apparatus 100. FIG. 41 illustrates the training pant 500 in a partially-fastened, ready-to-use configuration.

As seen in FIG. 39, the training pant 500 has a longitudinal direction 1, a transverse direction 2 that is perpendicular to the longitudinal direction, a leading edge 527, and a trailing edge 529. The training pant 500 defines a front region 522, a back region 524, and a crotch region 526 extending longitudinally between and interconnecting the front region and the back region. The training pant 500 also has an inner surface 523 (i.e., body-facing surface) adapted in use to be disposed toward the wearer, and an outer surface 525 (i.e., garment-facing surface) opposite the inner surface.

The illustrated training pant 500 also includes an outer cover 540, and a liner 542 joined to the outer cover, and an absorbent core 544 disposed between the outer cover and the liner. A pair of containment flaps 546 is secured to the liner 542 and/or the absorbent core 544 for inhibiting generally lateral flow of body exudates. The outer cover 540, the liner 542 and the absorbent core 544 can be made from many different materials known to those skilled in the art. The illustrated training pant 500 further includes a pair of transversely opposed front side panels 534, and a pair of transversely opposed back side panels 535. The side panels 534, 535 can be integrally formed with either the outer cover 540 or the liner 542, or may comprise separate elements.

As seen in FIG. 41, the front and back side panels 534, 535 of the training pant 500 can be selectively connected together by a fastening system 580 to define a three-dimensional configuration having a waist opening 550 and a pair of leg openings 552. The fastening system 580 comprises laterally opposite first fastening components 582 adapted for refastenable engagement to corresponding second fastening components 584. In one embodiment, each of the first fastening components 582 comprises a plurality of engaging elements adapted to repeatedly engage and disengage corresponding engaging elements of the second fastening components 584 to releasably secure the training pant 500 in its three-dimensional configuration.

The fastening components 582, 584 can comprise any refastenable fasteners suitable for absorbent articles, such as adhesive fasteners, cohesive fasteners, mechanical fasteners, or the like. In one particular embodiment, the fastening components 582, 584 comprise complementary mechanical fastening elements. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated embodiment, the first fastening components 582 comprise loop fasteners and the second fastening components 584 comprise complementary hook fasteners. Alternatively, the first fastening components 582 may comprise hook fasteners and the second fastening components 584 may comprise complementary loop fasteners. In another embodiment, the fastening components 582, 584 can comprise interlocking similar surface fasteners, or adhesive and cohesive fastening elements such as an adhesive fastener and an adhesive-receptive landing zone or the like. Although the training pant 500 illustrated in FIG. 41 show the back side panels 535 overlapping the front side panels 534 upon connection thereto, which is conventional, the training pant can also be configured so that the front side panels overlap the back side panels when connected.

The illustrated training pant 500 further includes a front waist elastic member 554, a rear waist elastic member 556, and leg elastic members 558, as are known to those skilled in the art. The front and rear waist elastic members 554, 556 can be joined to the outer cover 540 and/or liner 542 adjacent the leading edge 527 and the trailing edge 529, respectively, and can extend the full length of or part of the length of the edges. The leg elastic members 558 can be joined to the outer cover 540 and/or liner 542 along transversely opposing leg opening side edges 536 and positioned in the crotch region 526 of the training pant 500.

The elastic members 554, 556, 558 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example with the application of heat, such that elastic constrictive forces are imparted to the substrate. One non-limiting example of a suitable elastic material includes dry-spun coalesced multifilament spandex elastomeric threads sold under the trade name LYCRA, available from Invista, having a place of business located in Wichita, Kans., U.S.A.

FIG. 40 illustrates the training pant 500 in its folded configuration wherein it has been folded about a transverse fold axis A-A so that a first portion 571 of the training pant is in a superimposed relation with a second portion 572 of the training pant. The first and second portions 571, 572 of the training pant are illustrated in FIG. 39. In the illustrated embodiment, the inner surface 523 of the first portion 571 is in a facing relation with the inner surface of the second portion 572. In addition, the transverse fold axis A-A is shown in the approximate longitudinal center of the prefolded-training pant 500, and the leading edge 527 and the trailing edge 529 of the folded training pant are longitudinally aligned. It is understood that the transverse fold axis A-A can be positioned anywhere between the leading edge 527 and the trailing edge 529 as may be desired, which can result in a longitudinal offset of the leading edge and the trailing edge (particularly as it relates to other products). Moreover, the transverse fold axis A-A need not be perpendicular to the longitudinal direction 1, but rather may be skewed at an angle from the transverse direction 2, if desired. It can also be seen in the illustrated embodiment that the first fastening component 582 and the second fastening component 584 are accurately aligned with one another.

Figure 42:
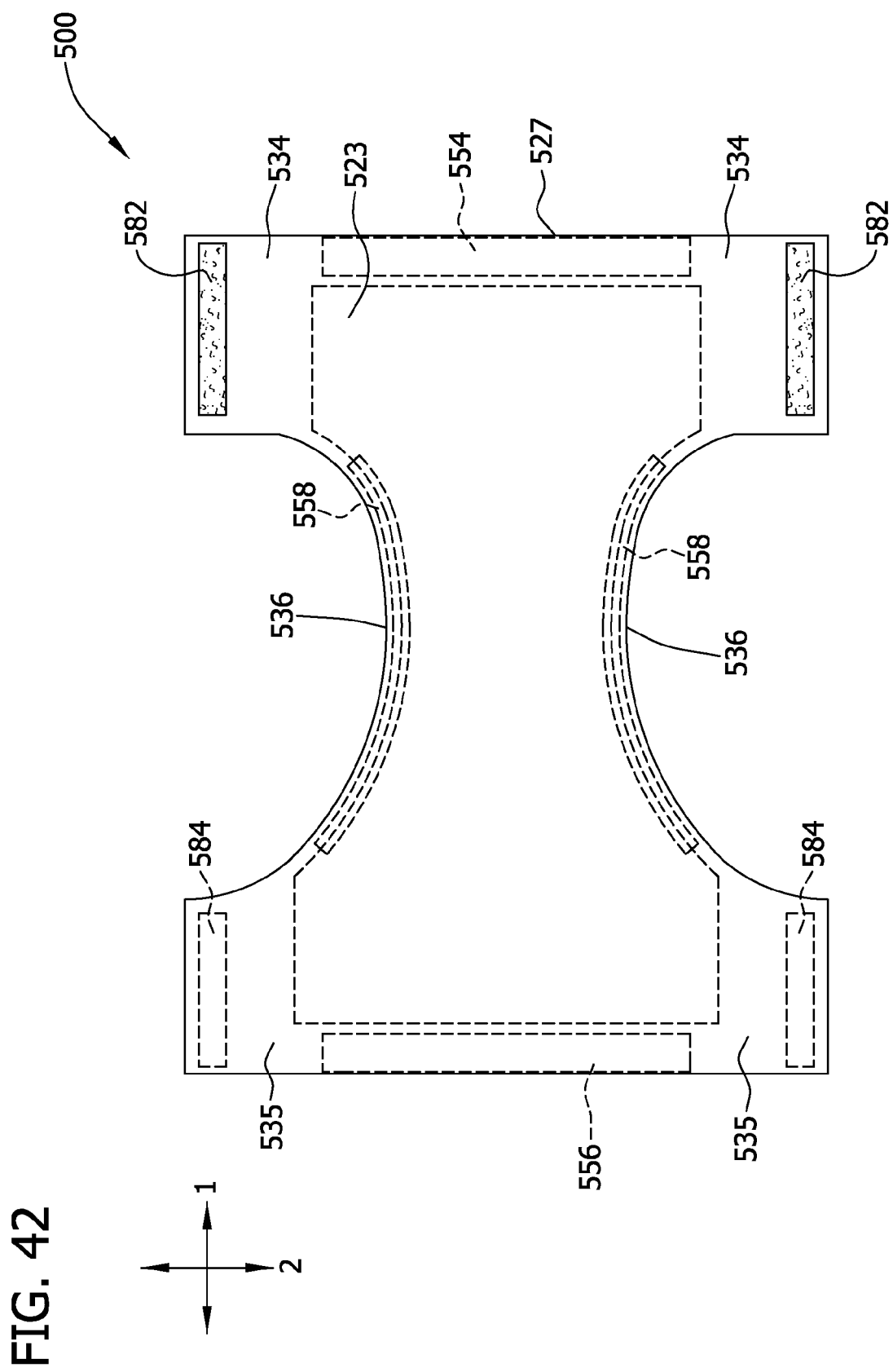
FIG. 42 is a top view of the training pant having front and back side panels.
Figure 43:
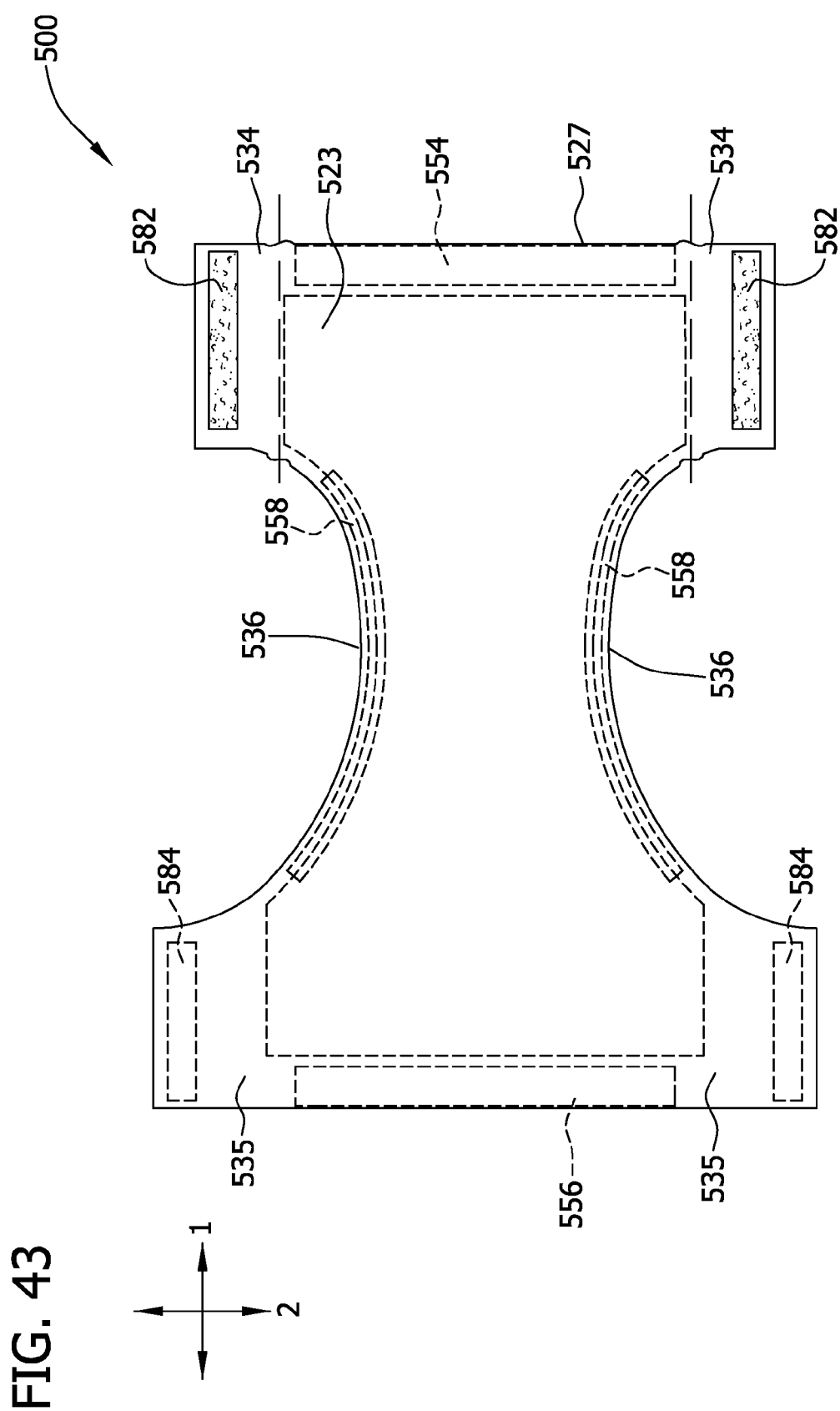
FIG. 43 is a top view similar to FIG. 42 but with the front side panels of the training pant being scrunched.

In this embodiment and as illustrated in FIG. 1, a discrete training pant 500 (one of the plurality of training pants passing through the manufacturing system 50) is delivered by the first conveying member 80 to one of the folding apparatus 100. The training pant 500 is delivered to the folding apparatus 100 with its front side panels 534 scrunched and each of its second fastening components 584 inverted (i.e., flipped approximately 180°). FIGS. 42 and 43 illustrate the training pant 500 with its front side panels 534 in their pre-scrunched and post-scrunched configurations, respectively. As seen in FIG. 43, each of the front side panels 534 is scrunched so that the first fastening components 582 are moved closer together as compared to the pre-scrunched configuration. It is contemplated that other portions of the front region 522 of the training pant 500 (i.e., portions other than the front side panels) can be scrunched to bring the first fastening components 582 closer together.

Figure 44:
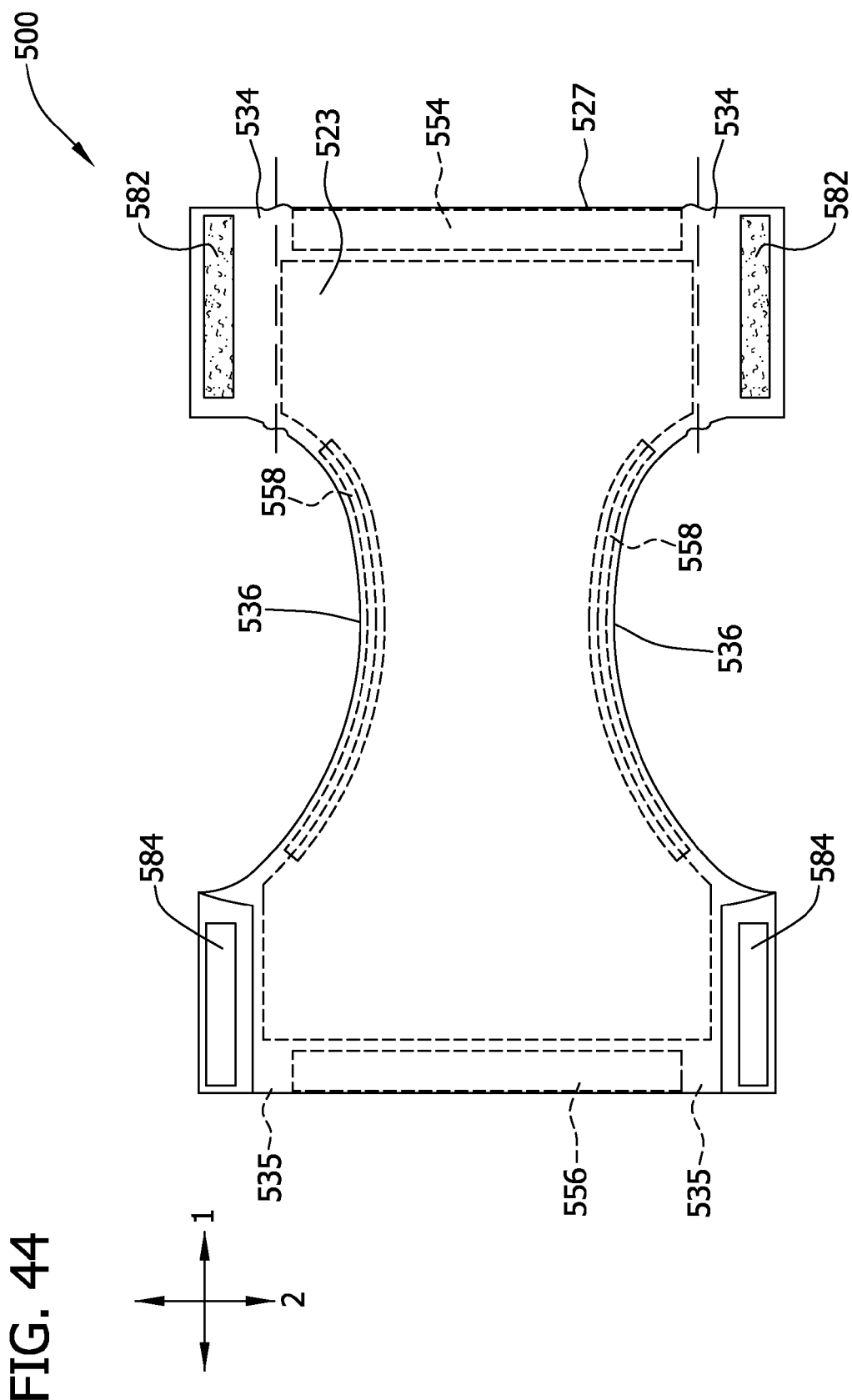
FIG. 44 is a top view similar to FIG. 43 but with portions of the back side panels being inverted.

The training pant 500 is illustrated in FIG. 44 with its second fastening components 584, which are located on respective back side panels 535, inverted and its front side panels 534 scrunched. As seen therein, both the first and second fastening components 582, 584 are now facing in the same direction. In addition, each of the first fastening components 582 is longitudinally aligned with a respective one of the second fastening components 584. As mentioned above, the training pant 500 is delivered to the folding apparatus 100 with its front side panels 534 scrunched and each of its second fastening components 584 inverted.

In the illustrated embodiment, half of the training pants 500 are delivered to each of the folding apparatus 100. Devices suitable for use as the first conveying member 80 are well-known in the art and include, but are not limited to, drums, rollers, belt conveyors, air conveyors, vacuum conveyors, chutes, and the like. For exemplary purposes, the first conveying member 80 is illustrated herein as a vacuum belt conveyor. In one suitable embodiment, the first conveying member 80 includes a conveying-assist device 82 (FIG. 1) to assist in keeping the training pants in a controlled position during advancement. Conveying-assist means are well-known in the art and, for example, include support belts, vacuum means, support rolls, secondary conveyor belts, guide plates, fluid-operated stabilizing apparatus, and the like.

Since both of the folding apparatus 100 are the same, the operation of only one of them will be described herein. The receiving roll 110 is aligned with respect to the first conveying member 80 so that the opening 125 in the opened segment 124 of the inner cylinder 111 is adjacent the first conveying member 80. As a result, the apertures 129 in the engagement member 127 of the outer cylinder 112 are subjected to a vacuum when they pass by the opening 125 and the vacuum source is applying vacuum to the interior chamber 113. The outer cylinder 112 of the illustrated receiving roll 110 is rotated in a counterclockwise direction (broadly, a first direction) by the drive assembly 117 at a constant surface speed, and suitably at the same speed that the training pant 500 is traveling on the first conveying member 80. The vacuum source is activated to apply a vacuum to the interior chamber 113 of the inner cylinder 111 via the conduit 115 and the openings 116 in the conduit. The training pant 500 is delivered to the receiving roll 110 by the first conveying member 80 with its outer cover 540 facing upward (i.e., away from the first conveying member) and its first and second fastening components 582, 584 facing downward (i.e., toward the first conveying member).

Figure 45:
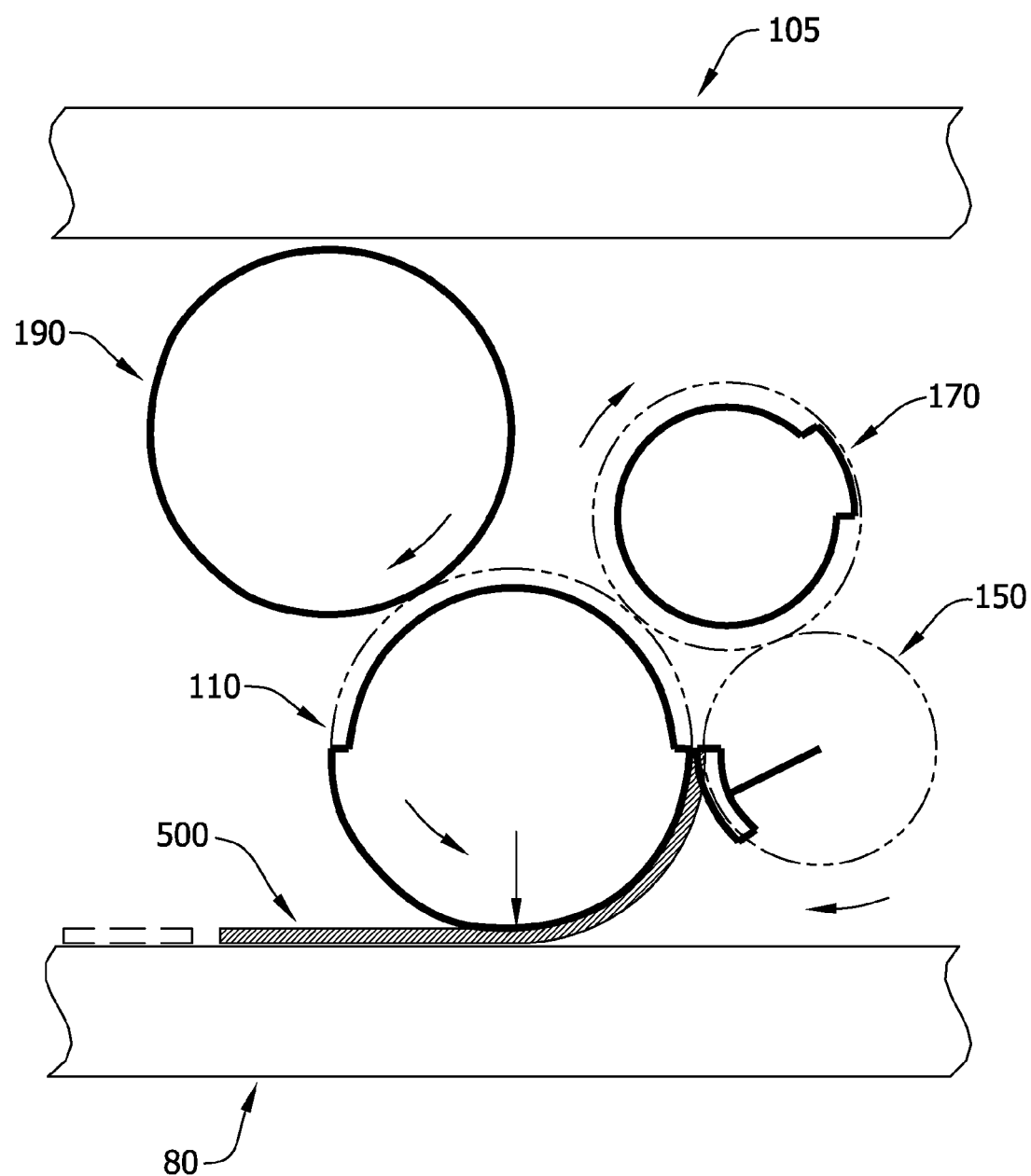
FIG. 45 is a schematic of the folding apparatus with the training pant entering the folding apparatus in its prefolded, laid-flat configuration and being held by the receiving roll.

When the leading edge 527 of the training pant 500 reaches the receiving roll 110, the outer cover 540 of the training pant is aligned with and grasped by the leading boundary of the first zone 133 of the engagement member 127 of the outer cylinder 112 of the receiving roll 110. As the receiving roll rotates away from the first conveying member 80, the leading edge 527 of the training pant 500 is lifted off of the first conveying member and transferred to the receiving roll (FIG. 45). As the remainder of the training pant 500 is delivered to the receiving roll 110 by the first conveying member 80, it is aligned with and grasped by the receiving roll in substantially the same manner as the leading edge 527.

The training pant 500 is delivered to the receiving roll 110 in such a manner that the training pant is generally aligned with the apertures 129 in the engagement member 127. As a result, the first portion 571 of the training pant 500 overlies the first zone 133 of the engagement member 127 and the second portion 572 of the training pant overlies the second zone 135. As a result, the entire training pant 500 is held by the receiving roll 110 as it is transferred from the first conveying member 80 thereto.

As the training pant 500 rotates with the outer cylinder 112 of the receiving roll 110, the leading edge 527 of the training pant is moved adjacent the oscillating member 150 as seen in FIG. 45. The inner cylinder 111 is configured such that the opened segment 124 extends generally from the tangent point of the receiving roll 110 with the first conveying member 80 to a first nip defined by the receiving roll and the oscillating member. The slotted segment 122 of the inner cylinder 111 of the receiving roll 110 extends generally from the first nip to a fourth nip defined by the receiving roll and the transfer roll. The apertures 129 in the first zone 133 do not align with the slots 123 in the slotted segment 122 of the inner cylinder 111, the vacuum within the interior chamber 113 of the inner cylinder 111 is blocked thereby releasing the leading edge 527 and subsequently the entire first portion 571 of the training pant 500 as it rotates beyond the first nip.

As the leading edge 527 of the training pant 500 approaches the first nip, the puck 164 of the oscillating member 150 moves adjacent the receiving roll at the first nip as shown in FIG. 45. The inner cylinder 151 of the oscillating member 150 is configured such that the narrower portion of slots 163 (the portion of the slots having the narrower width W2) extend generally from the first nip to a second nip defined by the oscillating member 150 and the folding roll 170.

As a result, the leading edge 527 of the training pant 500 approaches the puck 164 of the oscillating member 150 as the apertures 129 in the first zone 133 of the engagement member 127 of the outer cylinder 112 of the receiving roll 110 pass over the slotted segment 122 of the inner cylinder 111. Since the apertures 129 in the first zone 133 do not align with the slots 123 in the slotted segment 122, the vacuum within the interior chamber 113 of the inner cylinder 111 is blocked thereby releasing the leading edge 527 of the training pant 500 as it rotates. At approximately the same time or slightly before, the puck 164 of the oscillating member 150 contacts the liner 542 in the first portion 571 of the training pant 500 at a first nip defined by the puck of the oscillating member and the engagement member 127 of the receiving roll 110 (FIG. 45). At this point, the training pant 500 is subject to the vacuum of the oscillating member 150 through the apertures 169 in the puck 164 as a result of the apertures being aligned with the slots 163 in the inner cylinder 151. More specifically, each of the first fastening components 582 and the front waist elastic member 554 of the training pant 500 is grasped by the puck 164 because of the vacuum being applied thereto through the apertures 169 in the puck.

Moreover, the apertures 129 located in the first zone 133 of the engagement member 127 rotate into alignment with the oval apertures 126 located in the slotted segment 122 of the inner cylinder 111 of the receiving roll 110. Since the oval apertures 126 are in fluid communication with the pressurized elongate enclosure 128, pressurized air moves from the elongate enclosure through the oval apertures 126, through the apertures 129 in the engagement member 127 of the outer cylinder 112, and into contact with the first portion 571 of the training pant 500. The pressurized air assists in the transfer of the first portion 571 of the training pant 500 from the first zone 133 of the engagement member 127 of the outer cylinder 112 of the receiving roll to the puck 164 of the oscillating member 150.

Figure 46:
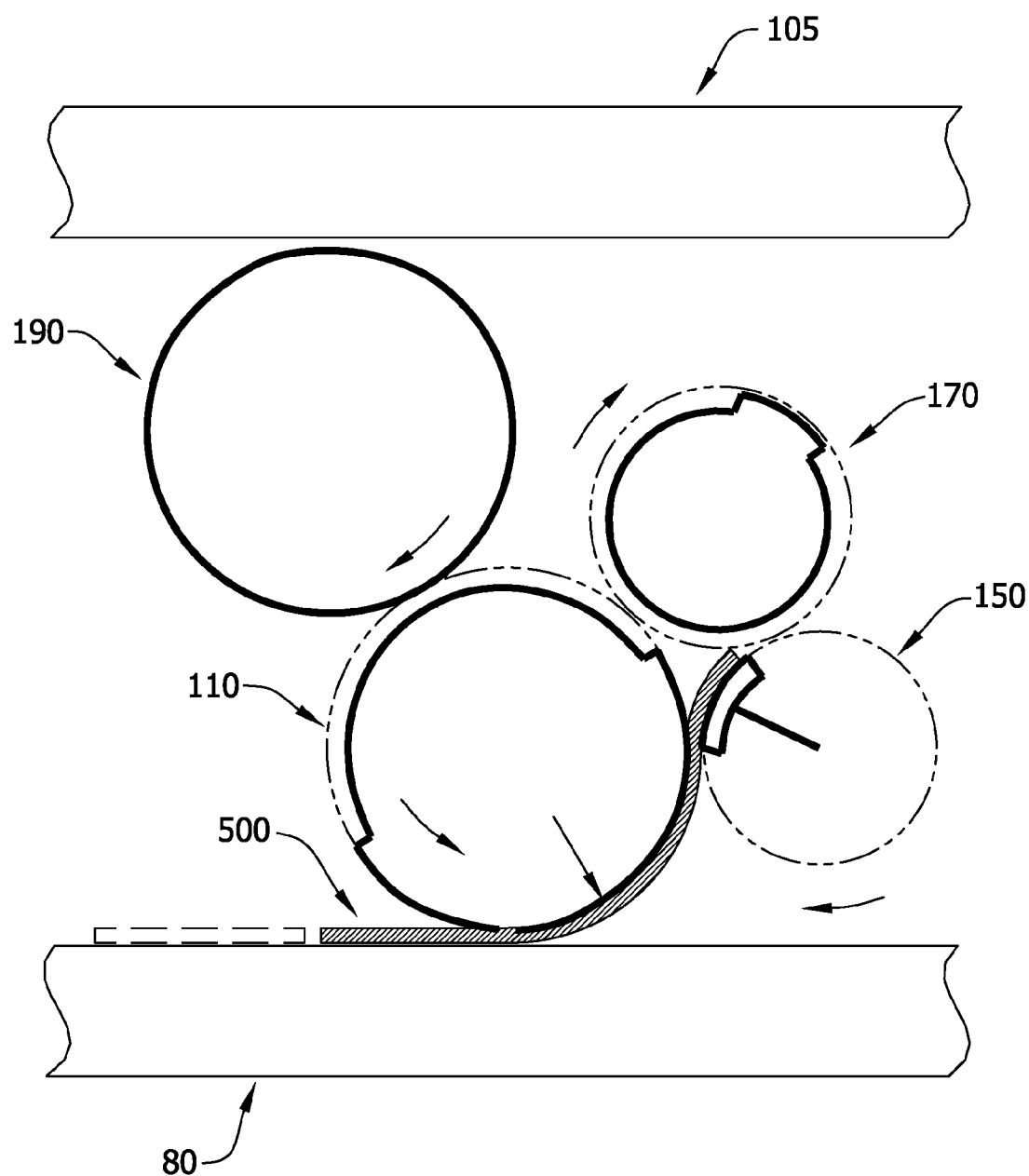
FIG. 46 is a schematic of the folding apparatus with the training pant having a first portion thereof being transferred from the receiving roll to the oscillating member and a second portion thereof held by the receiving roll.

The first portion 571 of the training pant 500 is transferred to the puck 164 of the outer cylinder 152 of the oscillating member 150 while the outer cylinder (and thereby the puck) is being rotated relative to the receiving roll 110 by the drive assembly 157 of the oscillating member. As seen in FIGS. 45 and 46, the outer cylinder 152 of the oscillating member 150 is moving in a clockwise direction (broadly, a second direction), which is opposite the rotation of the outer cylinder 112 of the receiving roll 110. In addition, the outer cylinder 152 of the oscillating member 150 is rotating at approximately the same surface speed as the outer cylinder 112 of the receiving roll 110 when the first portion 571 of the training pant 500 is transferred from the receiving roll 110 to the oscillating member 150.

The second portion 572 of the training pant 500 remains held to the receiving roll 110 through the rotation of the outer cylinder 112 past the slotted segment 122 of the inner cylinder 111 because the apertures 129 in the second zone 135 of the engagement member 127 are aligned with the slots 123 in the slotted segment. As a result, the vacuum continues to be applied to and thereby hold the second portion 572 of the training pant 500 to the engagement member 127 of the outer cylinder 112 of the receiving roll 110.

Once the leading edge 527 of the training pant 500 is transferred from the receiving roll 110 to the oscillating member 150 (or shortly thereafter), the outer cylinder 152 of the oscillating member begins to slow down. That is, the drive assembly 157 of the oscillating member 150, which is variable, reduces the surface speed at which the outer cylinder 152 of the oscillating member rotates relative to the receiving roll 110. In fact, once the outer cylinder 152 of the oscillating member 150 rotates a predetermined amount in the clockwise direction, the outer cylinder stops and rotates in the opposite direction (i.e., the counterclockwise direction). In the illustrated embodiment, the outer cylinder 152 of the oscillating member 150 moves in a generally pendular manner through about 180 degrees. In other words, the outer cylinder 152 of the oscillating member 150 rotates in a clockwise direction through about one-half rotation, stops, and then rotates back in a counterclockwise direction to its original position.

Figure 47:
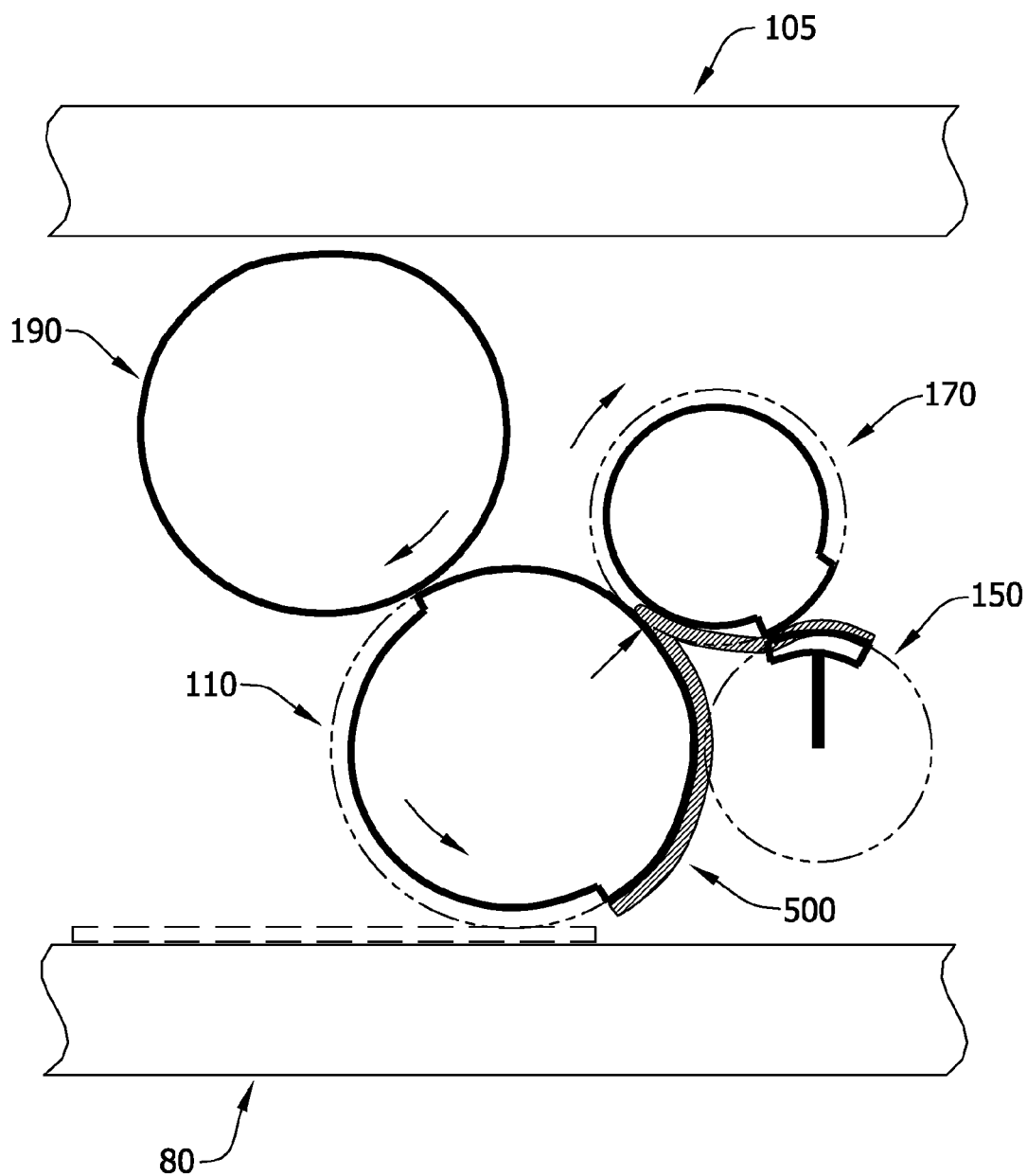
FIG. 47 is a schematic of the folding apparatus with the training pant beginning to fold and having the first portion thereof held by the oscillating member and the second portion thereof held by the receiving roll.

Because of the slowing, stopping, and change in rotational direction of the outer cylinder 152 of the oscillating member 150 relative to the outer cylinder 112 of the receiving roll 110, which is moving at a constant surface speed, the training pant 500 begin to fold (FIG. 47).

With the outer cylinder 152 of the oscillating member 150 stopped or beginning to rotate in the counterclockwise direction, the actuator 168 of the oscillating member 150 is actuated by applying the preset input current thereby causing the inner cylinder to translate relative to the outer cylinder 152 as illustrated in FIGS. 21 and 22. Since this occurs when the apertures 169 in the puck 164 of the oscillating member 150 are aligned with wider portions of the slots 163 in the slotted segment 162 (i.e., the portions of the slots 163 having the wider width W1), the first portion 571 of the training pant 500 remains securely held to the puck 164 by the vacuum. As seen in FIG. 21, the apertures 169 in the puck 164 remain in fluid communication with the vacuum being applied to the interior chamber 153 through the wider portions of the slots 163.

As the outer cylinder 152 of the oscillating member 150 rotates in a counterclockwise direction, the apertures 169 in the puck 164 move from the area of the slotted segment 162 with the wider portions of the slots 163 and over the area with the narrower portions. As a result of the apertures 169 in the puck 164 not being aligned with the narrow portions of the slots 163, the vacuum being applied to the interior chamber 153 is blocked by the inner cylinder and thereby inhibited from reaching the first portion 571 of the training pant 500 via the apertures 169 in the puck 164. In other words, the first portion 571 of the training pant 500 is released from the vacuum of the oscillating member 150.

As mentioned above, the outer cylinder 152 of the oscillating member 150 rotates in a clockwise direction through about one-half rotation, stops, and then rotates back in a counterclockwise direction to its original position. The actuator 168 of the illustrated embodiment is configured to be in its normal position when the outer cylinder 152 is rotating in the clockwise direction, and in its actuated position when the outer cylinder is rotating in its counterclockwise direction. As a result, the inner cylinder 151 is in the first position when the outer cylinder 152 is rotating clockwise and the second position when the outer cylinder is rotating in the counterclockwise direction. It is understood that the position of the inner cylinder 151 can be changed (i.e., the actuator 168 actuated or de-actuated) when the outer cylinder 152 is at a stopped position or while it is rotating.

With the outer cylinder 152 of the oscillating member 150 rotating in the counterclockwise direction, the first portion 571 of the training pant 500 is contacted by the puck 186 of the outer cylinder 172 of the folding roll 170 at a second nip defined by the oscillating member and the folding roll (FIG. 47). The outer cylinder 172 of the folding roll 170 is rotating at generally the same surface speed as the outer cylinder 152 of the oscillating member 150 but in the opposite direction (i.e., clockwise). The rotational surface speed of the outer cylinders 152, 172 of the oscillating member 150 and the folding roll 170 at this point in the folding process are slower than the rotational surface speed of the outer cylinder 112 of the receiving roll 110. As a result, the second portion 572 of the training pant 500 is moving faster than the first portion 571.

Figure 48:
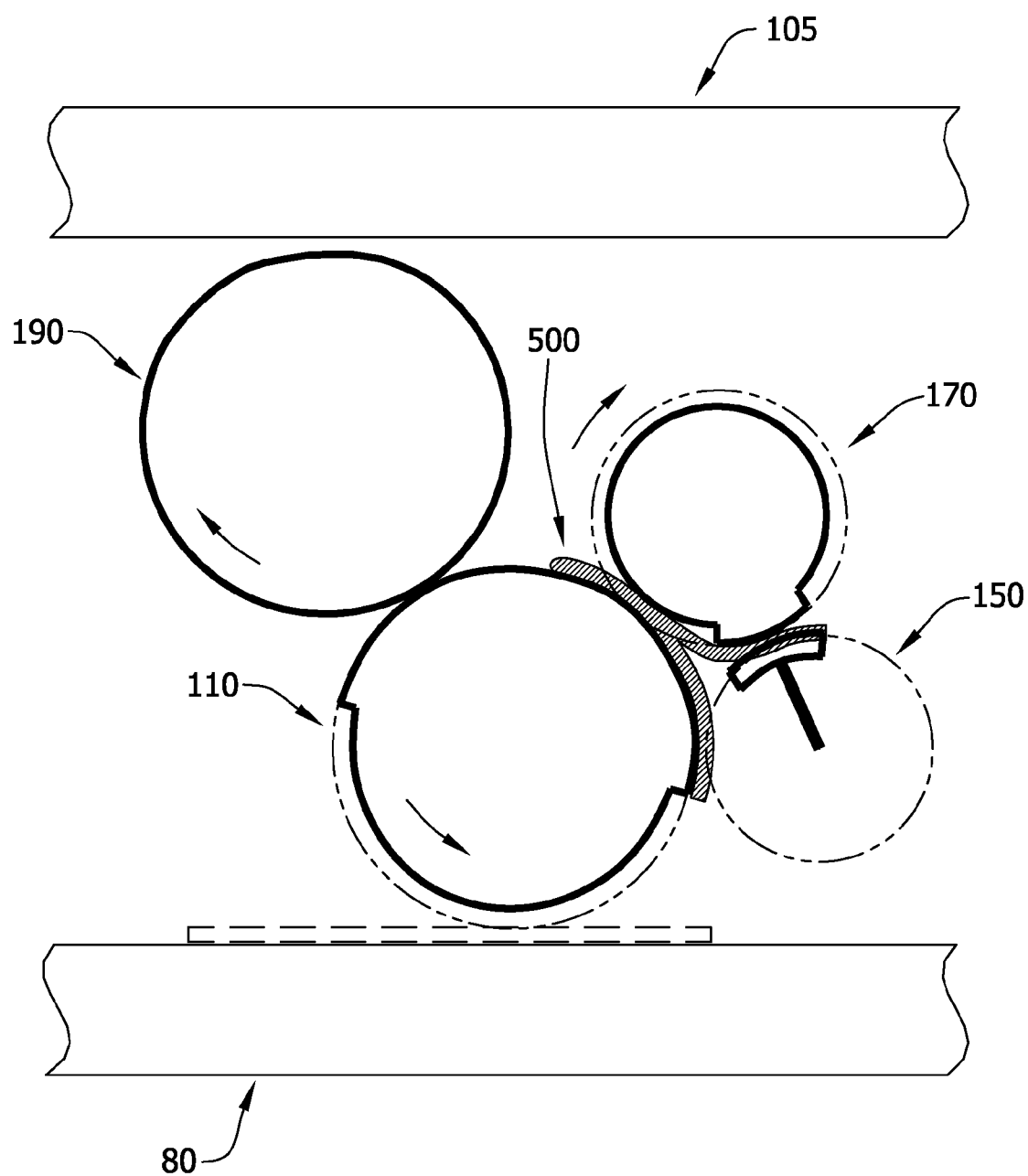
FIG. 48 is a schematic of the folding apparatus with the training pant having the first portion thereof being transferred from the oscillating member to the folding roll and the second portion thereof held by the receiving roll.

Because the vacuum being applied by the oscillating member 150 to the first fastening components 582 and front waist elastic member 554 of the training pant 500 is blocked by the inner cylinder 151, the first portion 571 of the training pant transfers from the puck 164 of the oscillating member to the puck 186 of the outer cylinder 172 of the folding roll 170 (FIG. 48). The primary and secondary openings 180, 182 in the inner cylinder 171 of the folding roll 170 are generally aligned with the apertures 188 in the puck 186 of the outer cylinder 172 of the folding roll thereby subjecting the first portion of the training pant 500 to the vacuum being applied to the interior chamber 173 of the inner cylinder. As a result, the first portion 571 of the training pant 500 transfers to the puck 186 of the outer cylinder 172 of the folding roll 170 at the second nip defined by the puck of the outer cylinder of the folding roll and the puck 164 of the outer cylinder 152 of the oscillating member 150 (FIG. 48).

Figure 49:
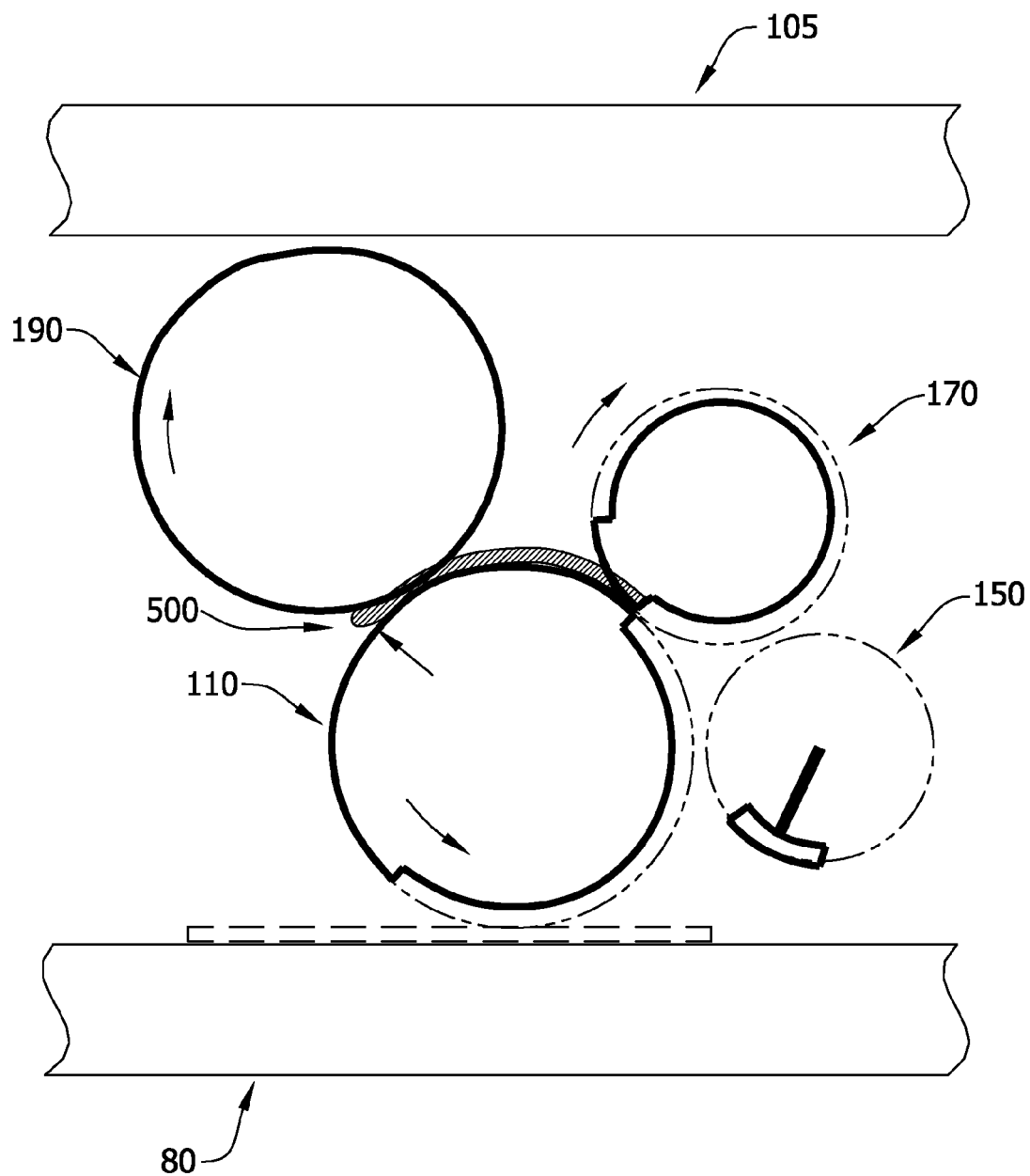
FIG. 49 is a schematic of the folding apparatus with the training pant having the first portion thereof held by the folding roll and the second portion thereof held by the receiving roll.

Once the first portion 571 of the training pant 500 is transferred from the oscillating member 150 to the folding roll 170, the rotational surface speed of the outer cylinder 172 of the folding roll 170 is increased by its drive assembly 176 to generally match the rotational surface speed of the outer cylinder 112 of the receiving roll 110. As illustrated in FIGS. 48 and 49, the outer cylinder 172 of the folding roll 170 is rotating a clockwise direction which is opposite from the counterclockwise direction of the outer cylinder 112 of the receiving roll 110. The first portion 571 of the training pant 500 is brought back into engagement with the engagement member 127 of the outer cylinder 112 of the receiving roll 110 at a third nip defined between the folding roll 170 and the receiving roll 110 such that the first portion 571 of the training pant is in overlying relationship with the second portion 572 (FIG. 49). In addition, each of the first fastening components 582 are engaged to a respective one of the second fastening components 584.

The primary and secondary openings 180, 182 in the inner cylinder 171 of folding roll 170 terminate adjacent the third nip. As a result, the vacuum holding the first portion 571 of the training pant 500 to the puck 186 of the folding roll 170 is blocked from contact therewith. As a result, the first portion 571 of the training pant 500 is transferred back to the receiving roll 110 and the training pants are arranged in its folded configuration. In addition, relative rotation of the folding roll 170 and receiving roll 110 applies both a compressive force and a shear force to the first and second fastening components 582, 584 thereby securely engaging the first and second fastening components together.

Figure 50:
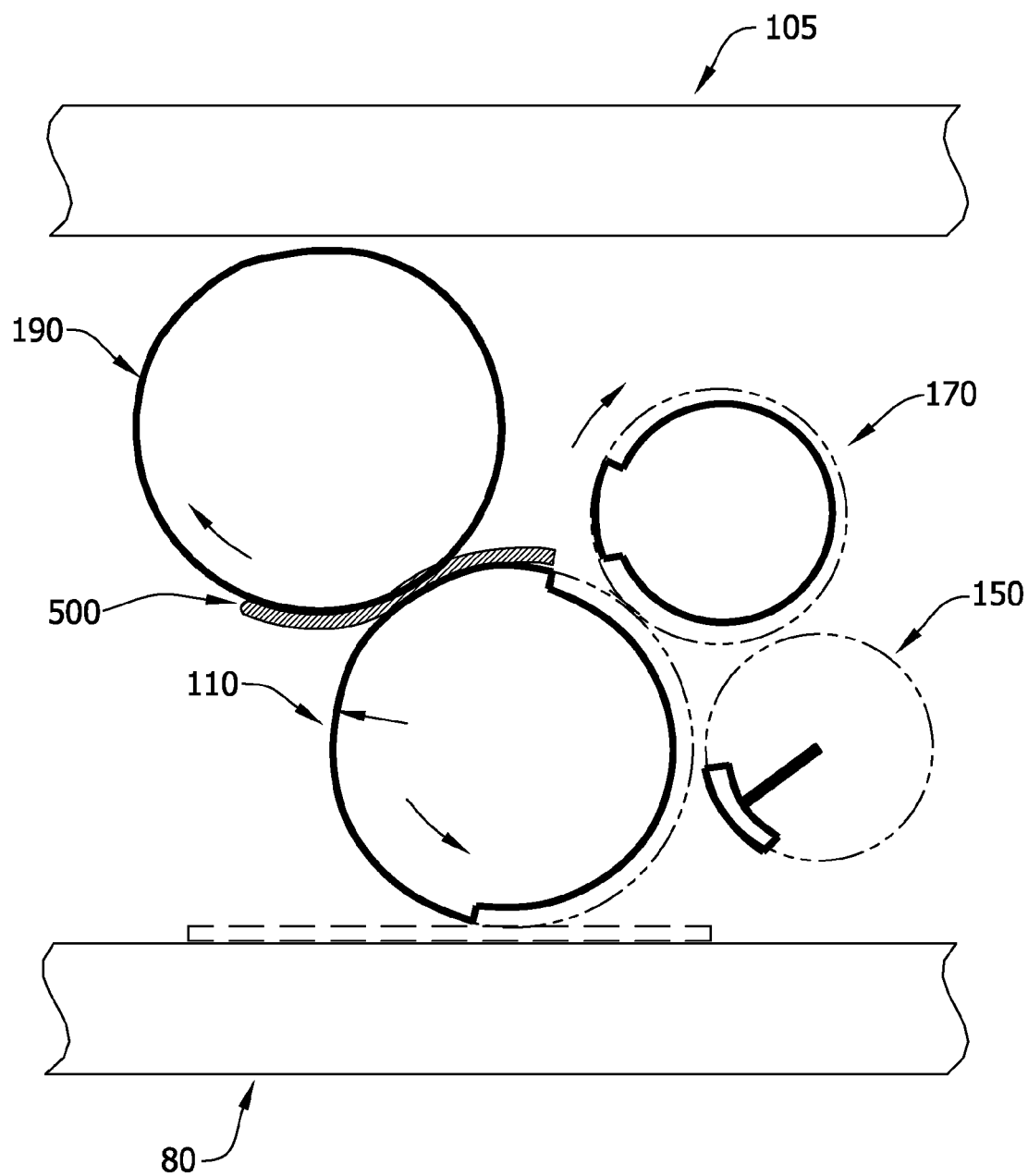
FIG. 50 is a schematic of the folding apparatus with the training pant being in its folded configuration and being transferred from the receiving roll to the transferring roll.

The training pant 500, which is in its folded configuration and has its first and second fastening components 582, 584 engaged, is then transferred from the receiving roll 110 to the transferring roll 190 at a fourth nip defined between the receiving roll and the transferring roll (FIGS. 49 and 50). The outer cylinder 112 of the receiving roll 110 is continuing to rotate in the counterclockwise direction at a constant surface speed. The outer cylinder 192 of the transferring roll 190 is rotating at approximately the same surface speed as the outer cylinder 112 of the receiving roll 110 but clockwise.

The transition from the slotted segment 122 to the solid segment 121 of the inner cylinder 111 of the receiving roll 110 is generally aligned with the fourth nip defined between the receiving roll and the transferring roll 190. As a result, the apertures 129 in the engagement member 127 are blocked from the vacuum by the solid segment 121 of the inner cylinder 111 and thereby inhibits the vacuum from being applied to the training pant 500. That is, the training pant 500 is free from the vacuum of the receiving roll 110 at this location.

The leading edges of the primary and secondary openings 202, 204 in the inner cylinder 191 of the transferring roll 190 are generally aligned with the fourth nip defined by the receiving roll 110 and the transferring roll. Thus, as the apertures 208 pass by the forth nip, the vacuum applied to the interior chamber 193 of the inner cylinder 191 of the transferring roll 190 is in fluid communication with the apertures in the puck of the outer cylinder 192 of the transferring roll. As a result, the outer cylinder 192 of the transferring roll 190 grasps the training pant 500 and thereby transfers the training pant 500 from the receiving roll 110 to the transferring roll. The training pant 500, which is in its folded configuration, is generally aligned with the profile (i.e., arrangement) of apertures 208 in the puck 206 of the outer cylinder 192. Accordingly, the entire training pant 500 including the fastening components 582, 584, which are securely engaged, is held in alignment by the transferring roll 190.

With reference again to FIG. 1, the transferring roll 190 carries the training pant 500 to and transfers the training pant to the second conveying member 105, which carries the training pant to additional components of the manufacturing system 50. In the illustrated embodiment, the second conveying member 105 is a vacuum belt conveyor. Other devices suitable for use as the second conveying member 105 are well-known in the art and include, but are not limited to, drums, rollers, air conveyors, vacuum conveyors, chutes, and the like.

In one suitable embodiment, training pants 500 can be manufactured at high line speeds (i.e., rates of 400 products per minute (ppm) or greater, such as 400 ppm to 4000 ppm, or 600 ppm to 3000 ppm, or 900 ppm to 1500 ppm). In the embodiment illustrated in FIG. 1, for example, training pants 500 can be manufactured at a rate of approximately 1000 ppm. Each of the illustrated folding apparatus 100 is capable of folding training pants at a rate of approximately 500 ppm. Thus, in another suitable embodiment having only one folding apparatus, the training pants 500 can be manufactured at high line speeds (i.e., 500 ppm). It is understood, that the line speeds of the illustrated manufacturing system 50 can be increased beyond 1000 ppm by adding additional folding apparatus 100.

As mentioned above, the outer cylinders 112, 192 of the receiving roll 110 and the transferring roll 190 rotate at a constant speed whereas the outer cylinders 152, 172 of the oscillating member 150 and the folding roll 170 move/rotate at variable speeds throughout the operation of the folding apparatus 100.

Figure 51:
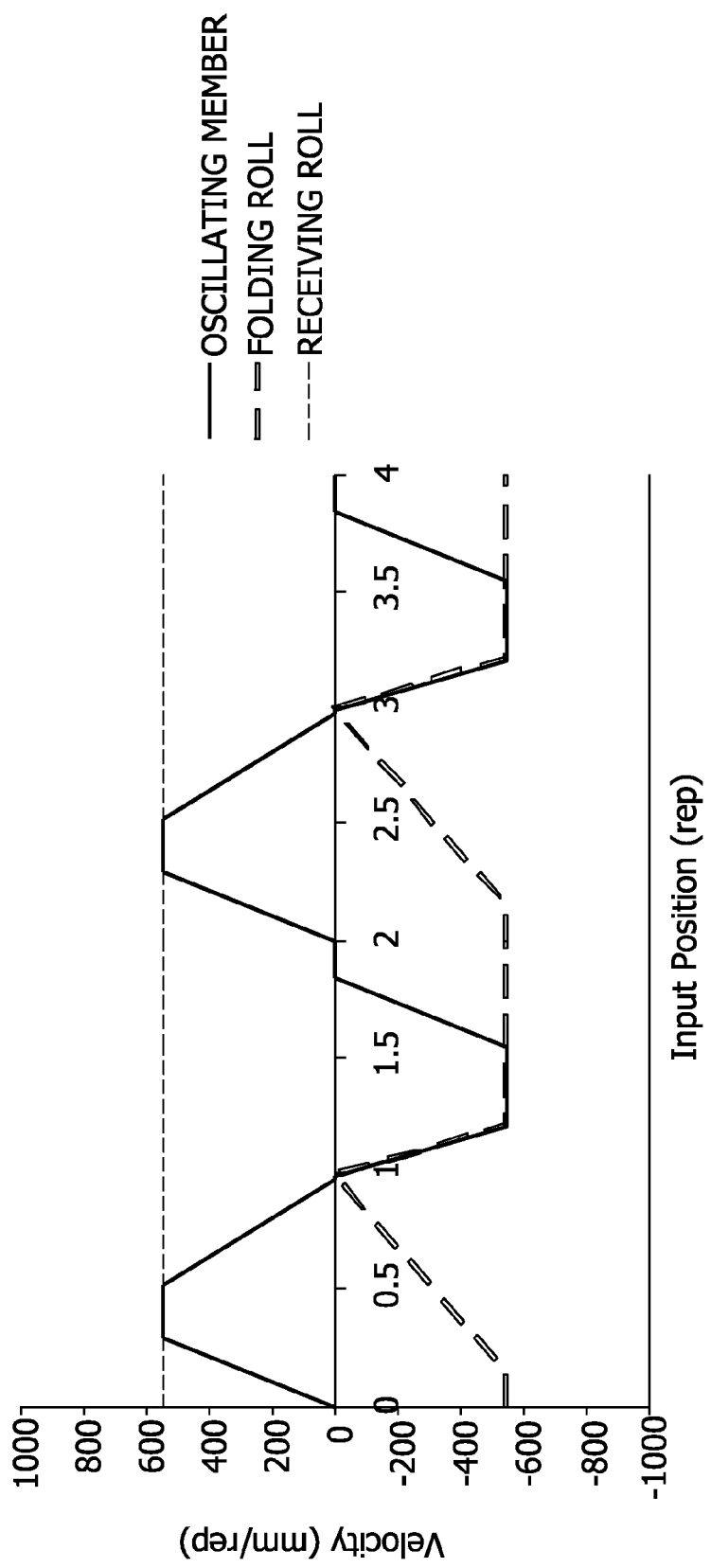
FIG. 51 is a graph illustrating one suitable embodiment of the velocity profiles for the receiving roll, the oscillating member, and the folding roll.
Figure 52A:
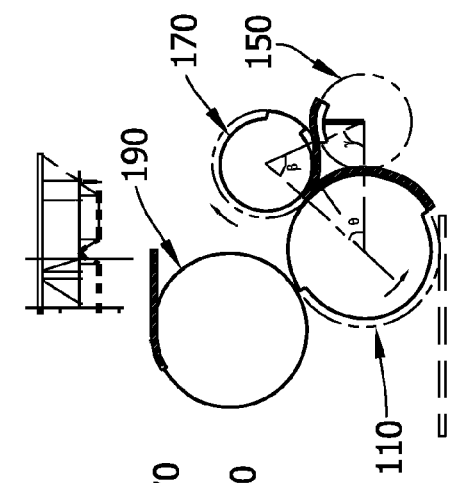
FIGS. 52(*a*)-(*f*) graphically and schematically illustrate the velocity profile of FIG. 51 at six different locations along the profile.
Figure 52B:
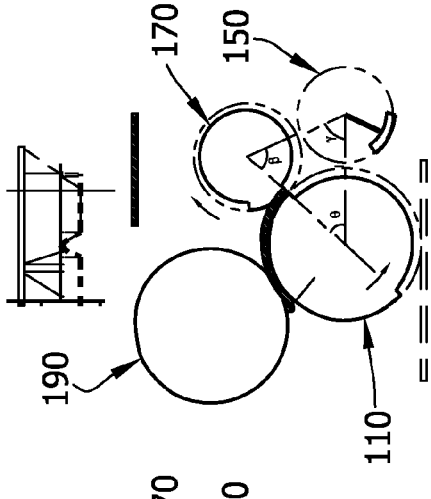
Figure 52C:
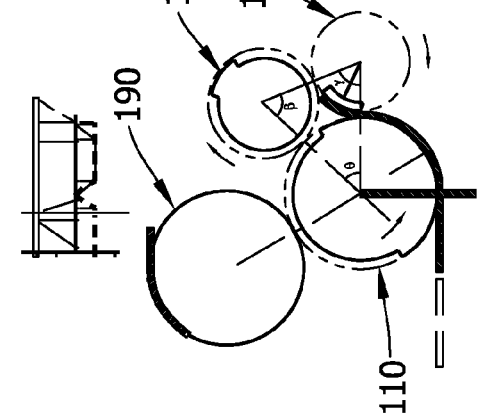
Figure 52D:
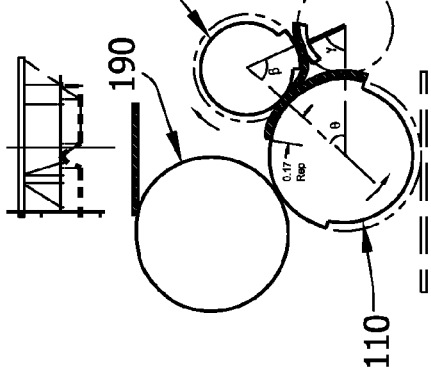
Figure 52E:
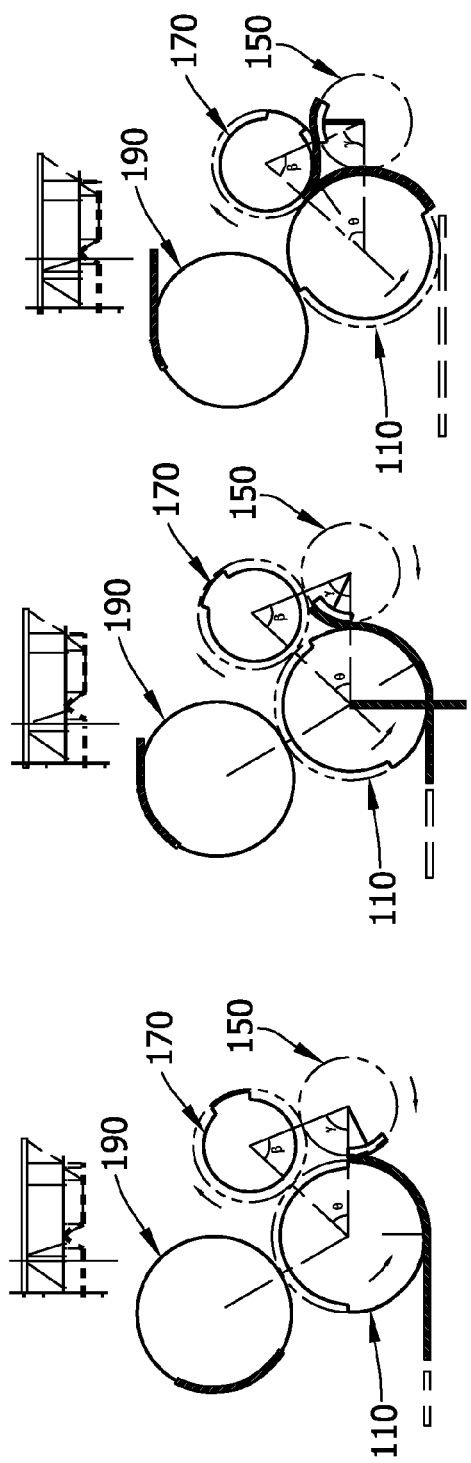
Figure 52F:
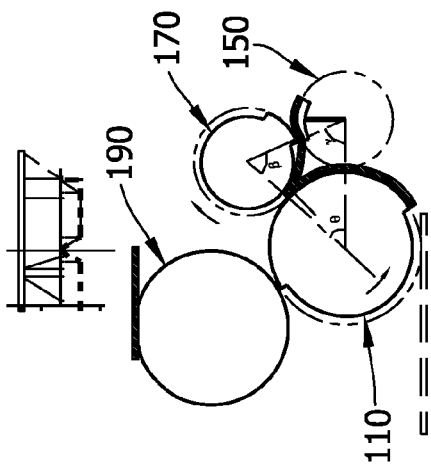

FIG. 51 is a graph illustrating one suitable embodiment of the relative velocity profiles between the receiving roll 110, the oscillating member 150, and the folding roll 170. FIGS. 52(a)-(f) graphically and schematically illustrate the velocity profile of FIG. 51 at six different locations along the profile. As seen in FIG. 51, the velocity profile for the receiving roll 110 is constant and in the first direction. The velocity profile for the oscillating member 150 begins at a stopped position and accelerates to match the velocity of the receiving roll 110. Once the velocity of the receiving roll 110 and oscillating member 150 are approximately the same, the first portion 571 of the training pant 500 is transferred from the receiving roll to the oscillating member.

After the first portion 571 of the training pant 500 is received by the oscillating member 150, the oscillating member decelerates and comes to a stopped position. After a brief stop, the oscillating member accelerates in the opposite direction at approximately the same rate as the folding roll 170 during which the first portion 571 of the training pant 500 is transferred from the oscillating member to the folding roll. After the first portion 571 is transferred from the oscillating member 150, the oscillating member decelerates to a stopped position and repeats its velocity profile.

As seen in FIG. 51, the velocity profile of the folding roll 170 begins with the folding roll rotating at a constant speed and then decelerates to a stopped position. From the stopped position, the folding roll 170 and oscillating member 150 accelerate at generally the same rate during which time the first portion 571 of the training pant 500 is transferred from the oscillating roll to the folding roll. The folding roll 170 continues to accelerate with the first portion 571 of the training pant 500 held thereto until the folding roll reaches a constant speed. The constant speed of the folding roll is generally the same as but in the opposite direction to that of the receiving roll 110. After the folding roll reaches a constant speed, the first portion 571 is transferred from the folding roll 170 to the receiving roll 110. The folding roll 170 then repeats its velocity profile.

The velocity profile of transferring roll 190, which is not illustrated in FIG. 51, is substantially the same as velocity profile for the receiving roll 110 but in the opposite direction. It is understood, however, that the velocity profiles of the transferring roll 190 and receiving roll 110 can differ.

Figure 53:
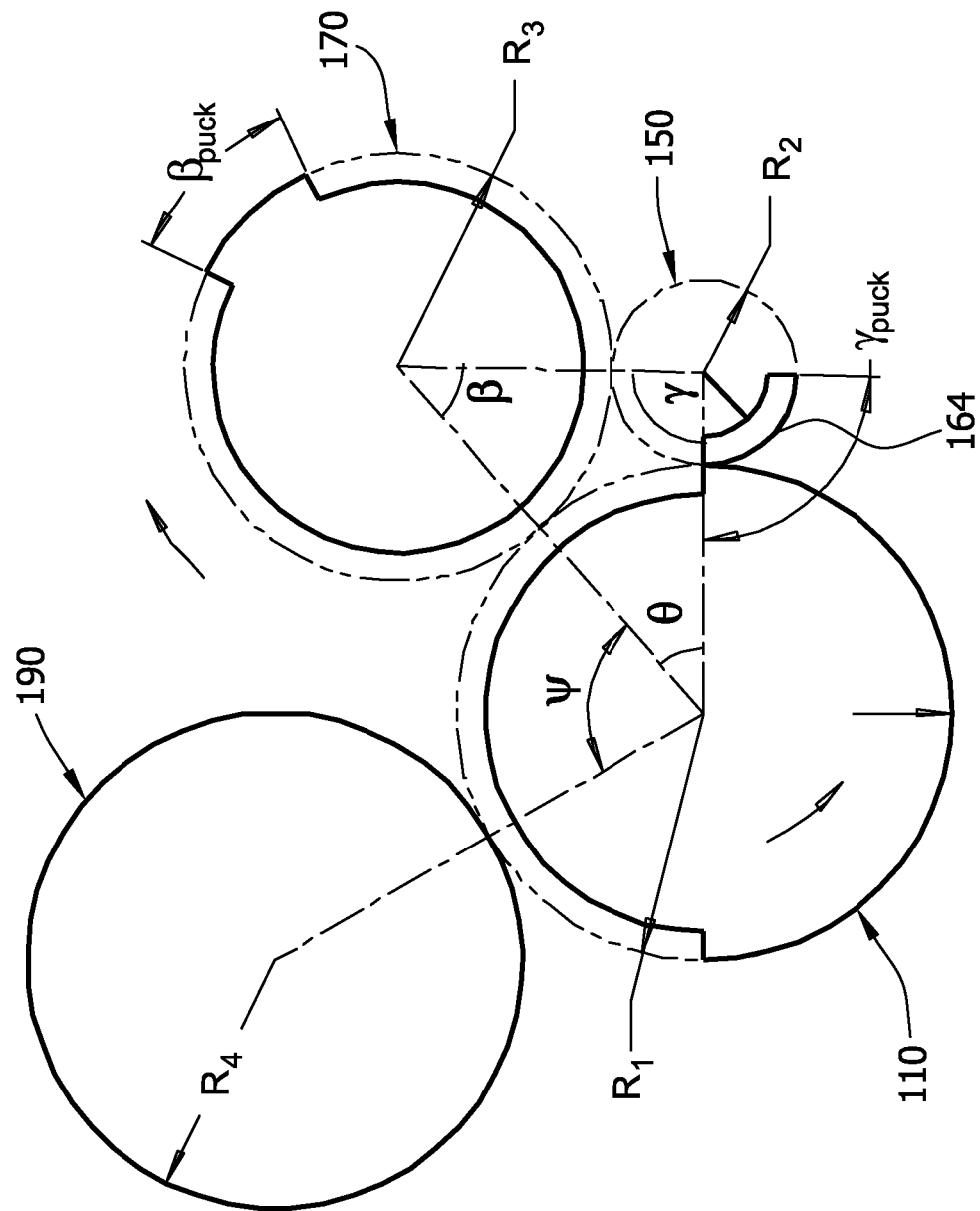
FIGS. 53 and 54 schematically illustrate suitable relative positions of the receiving roll, the oscillating member, the folding roll, and the transferring roll.
Figure 54:
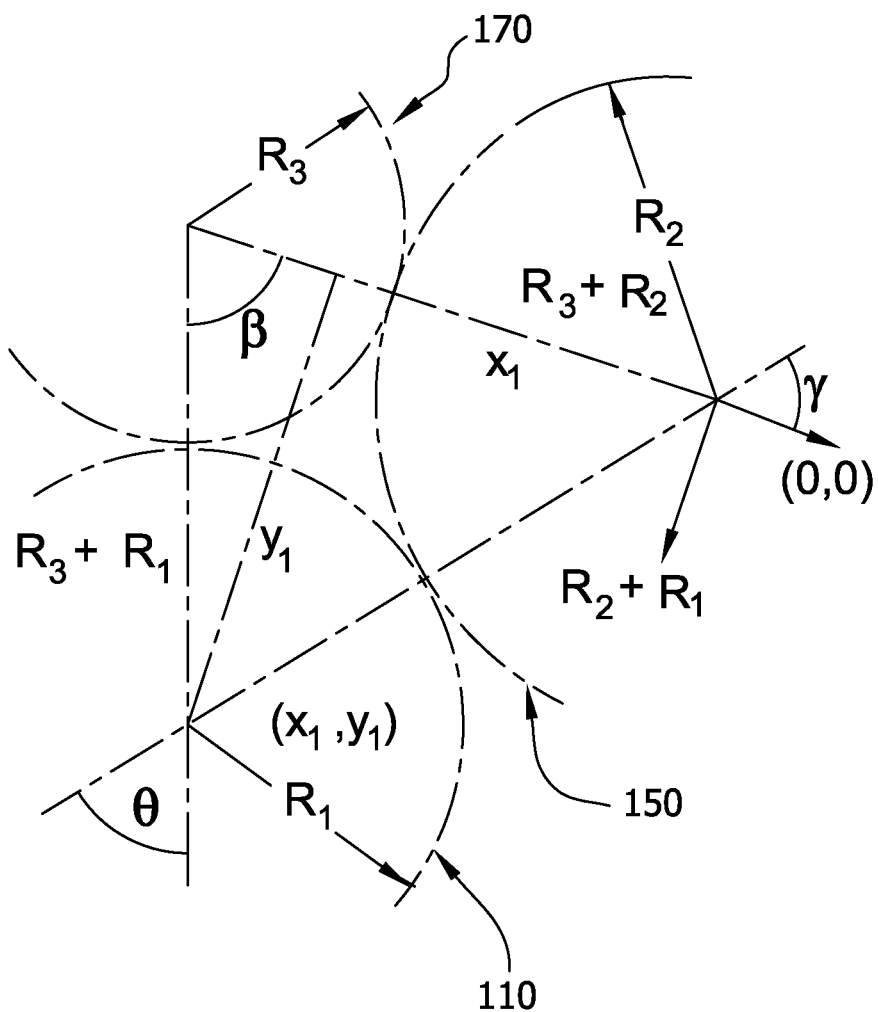

One suitable configuration of the apparatus 100 is illustrated in FIGS. 53 and 54. More specifically, FIGS. 53 and 54 illustrate one suitable configuration for the relative positioning between the receiving roll 110, the oscillating member 150, and the folding roll 170. As seen therein, the radii of the receiving roll 110, the oscillating member 150, and the folding roll 170 are labeled $R_1$, $R_2$ and $R_3$, respectively. It is contemplated that the system can have other suitable configurations than those illustrated herein.

Given the radii $R_1$, $R_2$ and $R_3$ of the receiving roll 110, the oscillating member 150, and the folding roll 170, angles $\alpha$, $\beta$, $\gamma$ between centers of the receiving roll, the oscillating member, and the folding roll can be calculated using the following equations.

Equation of a line passing through the center of the oscillating member 150, having slope $m_\gamma$:

$$y = m_\gamma(x-0)+0 \tag{1}$$

Equation of a line passing through the center of the folding roll 170 having slope $m_\beta$:

$$y = m_\beta(x+R_2+R_3)+0 \tag{2}$$

Equation of a circle at the origin passing through the center of the receiving roll 110:

$$(R_1+R_2)^2 = x^2 + y^2 \tag{3}$$

Equation of a circle with center at folding roll 170 passing through center of the receiving roll 110:

$$(R_1+R_3)^2 = (x+R_2+R_3)^2 + y^2 \tag{4}$$

Eliminate $y^2$ from (4) using (3), solving for x yields $x_1$, the x-coordinate of the conveyor center:

$$(R_1+R_3)^2 = (x+R_2+R_3)^2 + (R_1+R_2)^2 - x^2 \tag{5}$$

$$(R_1+R_3)^2 = x^2 + 2(R_2+R_2)x + (R_2+R_3)^2 + (R_1+R_2)^2 - x^2 \tag{6}$$

$$x_1 = \frac{R_1(R_2-R_3) + R_2(R_2+R_3)}{(R_2+R_3)} \tag{7}$$

$$y_1 = \sqrt{(R_1+R_2)^2 - X_1^2} \tag{8}$$

$$\beta = \text{Arctan}\left(\frac{y_1}{x_1+R_2+R_3}\right) \tag{9}$$

$$\gamma = \text{Arctan}\left(\frac{y_1}{x_1}\right) + (90° - \beta) \tag{10}$$

$$\theta = 180 - \gamma - \beta \tag{11}$$

Figure 55:
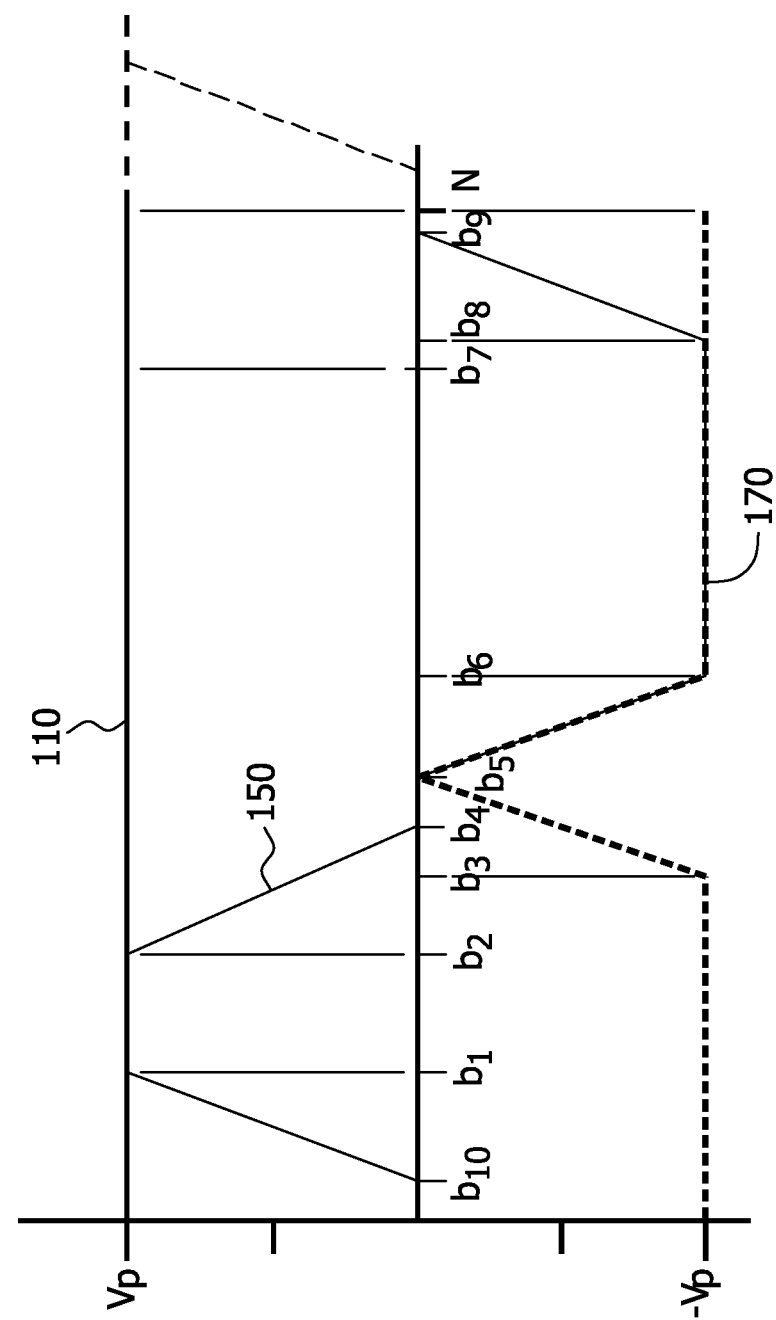
FIG. 55 graphically illustrates eleven constraints of the folding system of FIG. 1.

The motion profiles for the receiving roll 110, the oscillating member 150, and the folding roll 170 can be calculated using the following equations. In the illustrated system 50, there are ten transition points, which are indicated in FIG. 55 at $b_1$-$b_{11}$.

Folding roll 170 Circumference: Folding roll 170 makes one revolution every N products:

$$b3 - b6 = \frac{4\pi R_3}{V_p} - 2N \tag{12}$$

Match Ends Of Folded Product: Leading end of product reaches tangency point (TP), at same time as trailing end:

$$b_5 + b_6 - 2b_7 = \frac{-2R_3(\beta + \beta_{puck})}{V_p} \tag{13}$$

Product Mid-Point And Folding Roll Speed: Mid-point of product on receiving roll 110 is past TP, $b_{6f}$ repeats at time folding roll 170 reaches conveyor speed at $b_6$:

$$-b_1 + b_6 = \frac{(L_p + 2R_1\theta)}{2V_p} + b_{6f} \tag{14}$$

Receiving roll 110 Sweep Angle: Receiving roll 110 sweeps through $\theta°$ plus arc length of $L_p$:

$$-b_1 + b_7 = \frac{(L_p + R_1\theta)}{V_p} \tag{15}$$

Equal Puck Sweeps: Puck sweep CW equals puck sweep CCW:

$$-b_1 + b_2 + b_4 + b_5 + b_6 - b_8 - b_9 - b_{10} = 0 \tag{16}$$

Arbitrary Puck Slope Constraint: Final puck slope matches initial puck slope:

$$b_1 + b_8 - b_9 - b_{10} = 0 \tag{17}$$

Puck Reaches Conveyor Velocity: Freely choose $b_1$:

$$b_1 = z \tag{21}$$

Puck Forward Sweep: Puck sweeps through included angle $\gamma$ plus arc equal to puck length:

$$-2b_1 + b_2 + b_4 = \frac{2R_2(\gamma + \gamma_{puck})}{V_p} \tag{18}$$

Puck Matches Receiving Roll: Puck dwells with receiving roll 110 for arc equal puck length:

$$-b_1 + b_2 + b_4 = \frac{R_2 \gamma_{puck}}{V_p} \tag{19}$$

Puck Begins Accelerating: Freely choose $b_{10}$:

$$b_{10} = y \tag{20}$$

Putting the equations of constraint into matrix form we have:

$$A = \begin{bmatrix} 0 & 0 & 1 & 0 & 0 & -1 & 0 & 0 & 0 & 0 \\ 0 & 0 & 0 & 0 & 1 & 1 & -2 & 0 & 0 & 0 \\ -1 & 0 & 0 & 0 & 0 & 1 & 0 & 0 & 0 & 0 \\ 1 & 0 & 0 & 0 & 0 & 0 & -1 & 0 & 0 & 0 \\ -1 & 1 & 0 & 1 & 1 & 1 & 0 & -1 & -1 & -1 \\ 1 & 0 & 0 & 0 & 0 & 0 & 0 & 1 & -1 & -1 \\ 1 & 0 & 0 & 0 & 0 & 0 & 0 & 0 & 0 & 0 \\ -2 & 1 & 0 & 1 & 0 & 0 & 0 & 0 & 0 & 0 \\ -1 & 1 & 0 & 0 & 0 & 0 & 0 & 0 & 0 & 0 \\ 0 & 0 & 0 & 0 & 0 & 0 & 0 & 0 & 0 & 0 \end{bmatrix}$$

$$B = \begin{bmatrix} b_1 \\ b_2 \\ b_3 \\ b_4 \\ b_5 \\ b_6 \\ b_7 \\ b_8 \\ b_9 \\ b_{10} \end{bmatrix}$$

$$C = \begin{bmatrix} 4\pi R_3/V_p - 2N \\ -2R_3(\beta + \beta_{puck})/V_p \\ (L_p + 2R_1\theta)/V_p + b_{6f} \\ -(L_p + R_1\theta)/V_p \\ 0 \\ 0 \\ z \\ 2R_2(\gamma + \gamma_{Puck})/V_p \\ R_2 \gamma_{Puck}/V_p \\ y \end{bmatrix}$$

The solution for the bi's in the above set of equations can be found using either Gaussian elimination or matrix inversion. The solution using matrix inversion is of the form:

$$B = A^{-1} \cdot C$$

Consider a folder with the following parameters:
Q=1000 prod/min
Vp=546.1 mm/rep
Lpuck=116.2 mm
R_1=173.829 mm
R_2=98.784 mm
R_3=127.838 mm
N=2 folders
z=0.3
Y=0
b_6f=0.15
The above parameters yield the following center angles:
γ=73.70°
β=60.16°
θ=46.14°
Puck and Folding Roll Puck Angles:
$\beta_{Puck}$=52.09°
$\gamma_{puck}$=67.41°
The timing solution in the above system is as follows:
$b_1$=0.3
$b_2$=0.512811236
$b_3$=0.148030752
$b_4$=0.978191662
$b_5$=0.989163963
$b_6$=1.206339397
$b_7$=1.556339397
$b_8$=1.54325313
$b_9$=1.84325313
$b_{10}$=0

TABLE 2

Roll And Puck Dimensions Versus Product Size

| Size | 3.5 | 3 | 2 | |
|---|---|---|---|---|
| Vp = | 546.10 | 520.70 | 469.90 | mm/rep |
| Lpuck = | 116.22 | 165.74 | 100.00 | mm |
| R_1 = | 173.83 | 213.86 | 149.57 | mm |
| R_2 = | 98.78 | 213.86 | 85.00 | mm |
| R_3 = | 127.84 | 213.86 | 110.00 | mm |

Other apparatus suitable for holding, controlling, transferring, folding, winding and/or otherwise handling flexible materials and articles (including training pants) are described in U.S. patent application Ser. No. 12/971,999 entitled FOLDING APPARATUS AND METHOD OF FOLDING A PRODUCT; U.S. patent application Ser. No. 12/972,037 entitled FOLDING APPARATUS HAVING ROLLS WITH VARIABLE SURFACE SPEEDS AND A METHOD OF FOLDING A PRODUCT; and U.S. patent application Ser. No. 12/972,082 entitled VACUUM ROLL AND METHOD OF USE. Each of these applications is incorporated her1-3, 5, 6, 10-14, and 17ein by reference in their entireties.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. An apparatus for folding a product having a first portion and a second portion, the apparatus comprising:
    a receiving roll having a first direction of rotation, the receiving roll being adapted to selectively hold the first and second portions of the product thereto;
    a folding roll having a second direction of rotation that is opposite from the first direction of rotation, the folding roll being adapted to selectively hold the first portion of the product thereto; and
    an oscillating member adapted to transfer the first portion of the product from the receiving roll to the folding roll, the oscillating member comprising an inner cylinder, an outer cylinder that is rotatable about the inner cylinder, and a puck disposed on the outer cylinder, the outer cylinder being configured to move in both the first direction and the second direction.

2. The apparatus as set forth in claim 1 wherein the receiving roll and oscillating member define a first nip, the oscillating member being adapted to receive the first portion of the product from the receiving roll at the first nip.

3. The apparatus as set forth in claim 2 wherein the folding roll and oscillating member define a second nip, the oscillating member being adapted to transfer the first portion of the product to the folding roll at the second nip.

4. The apparatus as set forth in claim 3 wherein the receiving roll and folding roll define a third nip, the folding roll being adapted to transfer the first portion of the product from the folding roll to the receiving roll at the third nip.

5. The apparatus as set forth in claim 1 wherein the receiving roll is adapted to apply a vacuum to the product for selectively holding the product thereto.

6. The apparatus as set forth in claim 1 wherein the receiving roll is configured to rotate in the first direction at a constant speed.

7. The apparatus as set forth in claim 6 wherein the folding roll is configured to rotate in the second direction at a variable speed.

8. The apparatus as set forth in claim 1 wherein the outer cylinder has a plurality of apertures therein.

9. The apparatus as set forth in claim 8 wherein the product comprises a pair of fastening components located in the first portion thereof, the plurality of apertures in the outer cylinder being arranged to generally align with the fastening components of the product when the product is in contact with the oscillating member.

10. The apparatus as set forth in claim 1 further comprising a transferring roll adapted to receive the product from the receiving roll.

11. An apparatus for folding products having a first portion, a second portion, and a transverse fold axis, the apparatus comprising:
    a receiving roll configured to hold the first portion and the second portion of the product thereto and to release the first portion while continuing to hold the second portion of the product, the receiving roll being configured to rotate in a first direction;
    an oscillating member positioned adjacent the receiving roll, the oscillating member comprising an inner cylinder, an outer cylinder that is rotatable about the inner cylinder, and a puck disposed on the outer cylinder, the outer cylinder being capable of movement in the first direction and in a second direction, the oscillating member being configured to receive the first portion of the product from the receiving roll while the outer cylinder is moving in the second direction; and a folding roll positioned adjacent to the receiving roll and the oscillating member, the folding roll being rotatable in the second direction and configured to receive the first portion of the product from the oscillating member while the outer cylinder is moving in the first direction and to transfer the first portion of the product to the receiving roll such that the product is folded generally along the transverse fold axis and the first portion is generally overlying the second portion.

12. The apparatus as set forth in claim 11 wherein the receiving roll and oscillating member define a first nip, the oscillating member being adapted to receive the first portion of the product from the receiving roll at the first nip.

13. The apparatus as set forth in claim 12 wherein the folding roll and oscillating member define a second nip, the oscillating member being adapted to transfer the first portion of the product to the folding roll at the second nip.

14. The apparatus as set forth in claim 13 wherein the receiving roll and folding roll define a third nip, the folding roll being adapted to transfer the first portion of the product from the folding roll to the receiving roll at the third nip.

15. The apparatus as set forth in claim 11 wherein each of the receiving roll, the oscillating member, and the folding roll is adapted to apply a vacuum to the product for selectively holding at least a portion of the product thereto.

16. The apparatus as set forth in claim 11 wherein the receiving roll is configured to rotate in the first direction at a constant speed.

17. The apparatus as set forth in claim 16 wherein the folding roll is configured to rotate in the second direction at a variable speed.

18. The apparatus as set forth in claim 11 further comprising a transferring roll adapted to receive the product from the receiving roll.

* * * * *

UNITED STATES PATENT AND TRADEMARK OFFICE
CERTIFICATE OF CORRECTION

PATENT NO. : 9,132,982 B2
APPLICATION NO. : 12/972012
DATED : September 15, 2015
INVENTOR(S) : Joseph Daniel Coenen et al.

It is certified that error appears in the above-identified patent and that said Letters Patent is hereby corrected as shown below:

IN THE SPECIFICATION

In Column 4, Line 45, delete "system and" and insert therefor -- system 50 and --.

In Column 17, Line 14, Equation 6, delete "$2(R_2 + R_2)x$" and insert therefor -- $2(R_2 + R_3)x$ --.

Signed and Sealed this
Eighth Day of March, 2016

Michelle K. Lee
*Director of the United States Patent and Trademark Office*